United States Patent
Baum et al.

(10) Patent No.: US 10,669,317 B2
(45) Date of Patent: Jun. 2, 2020

(54) CHIMERIC INSECTICIDAL PROTEINS TOXIC OR INHIBITORY TO LEPIDOPTERAN PESTS

(71) Applicant: Monsanto Technology LLC, St. Louis, MO (US)

(72) Inventors: James A. Baum, Webster Groves, MO (US); Thomas A. Cerruti, Newton, MA (US); Crystal L. Dart, Norton, MA (US); Leigh H. English, Chesterfield, MO (US); Stanislaw Flasinski, Chesterfield, MO (US); Xiaoran Fu, Belmont, MA (US); Victor M. Guzov, Cambridge, MA (US); Arlene R. Howe, Chesterfield, MO (US); Jay P. Morgenstern, Boston, MA (US); James K. Roberts, Chesterfield, MO (US); Sara A. Salvador, Wildwood, MO (US); Jinling Wang, Belmont, MA (US)

(73) Assignee: Monsanto Technology LLC, St. Louis, MO (US)

( * ) Notice: Subject to any disclaimer, the term of this patent is extended or adjusted under 35 U.S.C. 154(b) by 221 days.

(21) Appl. No.: 15/849,012

(22) Filed: Dec. 20, 2017

(65) Prior Publication Data

US 2018/0127774 A1  May 10, 2018

Related U.S. Application Data

(63) Continuation of application No. 14/884,469, filed on Oct. 15, 2015, now Pat. No. 10,233,217.

(60) Provisional application No. 62/064,989, filed on Oct. 16, 2014.

(51) Int. Cl.
  *C07K 14/325* (2006.01)
  *C12N 15/82* (2006.01)
  *A01N 63/10* (2020.01)
  *C12N 15/62* (2006.01)

(52) U.S. Cl.
  CPC ............ *C07K 14/325* (2013.01); *A01N 63/10* (2020.01); *C12N 15/8286* (2013.01); *C07K 2319/00* (2013.01); *C12N 15/62* (2013.01); *Y02A 40/162* (2018.01)

(58) Field of Classification Search
  None
  See application file for complete search history.

(56) References Cited

U.S. PATENT DOCUMENTS

| | | | |
|---|---|---|---|
| 5,188,642 A | 2/1993 | Shah et al. | |
| 5,312,910 A | 5/1994 | Kishore et al. | |
| 5,500,365 A | 3/1996 | Fischhoff et al. | |
| 5,510,471 A | 4/1996 | Lebrun et al. | |
| 5,627,061 A | 5/1997 | Barry et al. | |
| 5,633,435 A | 5/1997 | Barry et al. | |
| 5,633,448 A | 5/1997 | Lebrun et al. | |
| 5,728,925 A | 3/1998 | Herrera-Estrella et al. | |
| 5,880,275 A | 3/1999 | Fischhoff et al. | |
| 6,017,534 A | 1/2000 | Marlvar et al. | |
| 6,033,874 A | 3/2000 | Baum et al. | |
| 6,204,246 B1 | 3/2001 | Bosch et al. | |
| 6,218,188 B1* | 4/2001 | Cardineau | C07K 14/325 435/468 |
| 6,501,009 B1 | 12/2002 | Romano | |
| 6,713,063 B1 | 3/2004 | Malvar et al. | |
| 6,962,705 B2 | 11/2005 | Malvar et al. | |
| 7,064,249 B2 | 6/2006 | Corbin et al. | |
| 7,070,982 B2 | 7/2006 | Malvar et al. | |
| 7,193,133 B2 | 3/2007 | Lassner et al. | |
| 7,510,878 B2 | 3/2009 | Abad et al. | |
| 7,772,465 B2 | 8/2010 | Abad et al. | |
| 7,812,129 B1 | 10/2010 | Abad et al. | |
| 8,304,604 B2* | 11/2012 | Lira | C07K 14/325 800/279 |
| 8,344,207 B2 | 1/2013 | Bogdanova et al. | |
| 8,609,936 B2 | 12/2013 | Baum et al. | |
| 2001/0026940 A1 | 10/2001 | Cardineau et al. | |
| 2003/0119158 A1* | 6/2003 | Malvar | C07K 14/325 435/184 |
| 2006/0021087 A1 | 1/2006 | Baum et al. | |
| 2006/0112447 A1 | 5/2006 | Bogdanova et al. | |
| 2008/0172762 A1 | 7/2008 | Cerf et al. | |
| 2008/0256667 A1 | 10/2008 | Dersch et al. | |
| 2008/0280361 A1 | 11/2008 | Calabotta et al. | |
| 2008/0282432 A1 | 11/2008 | Duncan et al. | |
| 2009/0138985 A1 | 5/2009 | Martinell et al. | |

(Continued)

FOREIGN PATENT DOCUMENTS

EP    0189707 A2    8/1986
EP    0508909 A1    10/1992

(Continued)

OTHER PUBLICATIONS

Fourgoux-Nicol et al, Plant Mol. Biol. (1999) 40: 857-872.*
Pardo Lopez et al, Peptides (2009) 30:589-595.*
Aronson et al, FEMS Microbiol. Lett. (2001) 195:1-8.*
Herrero et al., Biochem. J. (2004) 384:507-513.*
Abdul-Rauf et al, Curr. Microbiol. (1999) 39, 94-98.*
Bravo et al., "Evolution of *Bacillus thuringiencis* Cry toxins insecticidal activity," *Microbial Biotechnology*, 6:17-26 (2012).
Gen Bank Database, Apr. 25, 1994, Accession No. AAA 22344.1.

(Continued)

*Primary Examiner* — Mykola V. Kovalenko
(74) *Attorney, Agent, or Firm* — Timothy Ball; David R. Marsh; Arnold & Porter Kaye Scholer LLP

(57) ABSTRACT

Nucleotide sequences are disclosed that encode novel chimeric insecticidal proteins exhibiting Lepidopteran inhibitory activity. Particular embodiments provide compositions and transformed plants, plant parts, and seeds containing the recombinant nucleic acid molecules encoding one or more of the chimeric insecticidal proteins.

19 Claims, No Drawings

Specification includes a Sequence Listing.

(56) References Cited

U.S. PATENT DOCUMENTS

| | | |
|---|---|---|
| 2009/0142837 A1 | 6/2009 | Adams, Jr. et al. |
| 2009/0313721 A1 | 12/2009 | Abad et al. |
| 2010/0004176 A1 | 1/2010 | Sampson et al. |
| 2010/0017914 A1 | 1/2010 | Hart et al. |
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 6/2010 | Abad et al. |
| 2010/0197592 A1 | 8/2010 | Heinrichs |
| 2010/0269221 A1 | 10/2010 | Abad et al. |
| 2010/0317569 A1 | 12/2010 | Lira et al. |
| 2010/0319092 A1 | 12/2010 | Lira et al. |
| 2010/0319093 A1 | 12/2010 | Lira et al. |
| 2011/0030096 A1 | 2/2011 | Lira et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2012/0317681 A1 | 12/2012 | Meade et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson |
| 2014/0196175 A1 | 7/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |

FOREIGN PATENT DOCUMENTS

| | | |
|---|---|---|
| EP | 0218571 B1 | 2/1993 |
| EP | 0924299 A1 | 6/1999 |
| JP | 2009-505679 A | 2/2009 |
| JP | 2013-514769 A | 5/2013 |
| WO | WO 90/10076 | 9/1990 |
| WO | WO 99/24581 A2 | 5/1999 |
| WO | WO 01/14562 A1 | 3/2001 |
| WO | WO 01/19859 A2 | 3/2001 |
| WO | WO 02/14517 A1 | 2/2002 |
| WO | WO 2004/020636 A1 | 3/2004 |
| WO | WO2007027777 A1 | 3/2007 |
| WO | WO 2011/075588 A1 | 6/2011 |
| WO | WO2011075588 A1 | 6/2011 |
| WO | WO 2014/008054 A2 | 1/2014 |
| WO | WO 2014/055881 A1 | 4/2014 |

OTHER PUBLICATIONS

GenBank Database, Aug. 24, 1998, Accession No. AAC 32850.1.
GenBank Database, Apr. 18, 2005, Accession No. CAA 31951.1.
GenBank Database, Dec. 31, 2013, Accession No. AEH 31431.1.
GenBank Database, Apr. 26, 1993, Accession No. AAA 22561.1.
Gen Bank Database, Apr. 26, 1993, Accession No. AAA 22331.1.
GenBank Database, Nov. 18, 2005, Accession No. ABB 766664.1.
Maagd R. A. et al., "*Bacillus thuringiencis* Delta-Endotoxin Cry1C Domain III Can Function as a Specificity Determinant for *Spodoptera exigua* in Different, but Not All, Cry1-Cry1C Hybrids," *Applied and Environmental Microbiology*, 66(4):1559-1563 (2000).
Office Action in corresponding Application No. JP 2017-0520352, dated Feb. 5, 2019.
Abdul-Rauf et al., "Mutations of Loop 2 and Loop 3 Residues in Domain II of *Bacillus thuringiensis* Cry1 C δ-Endotoxin Affect Insecticidal Specificity and Initial Binding to *Spodoptera littoralis* and *Aedes aegypti* Midgut Membranes," *Current Microbiology*, 39:94-98 (1999).
Aronson et al., "Why *Bacillus thuringiensis* insecticidal toxins are so effective: unique features of their mode of action," *FEMS Microbiology Letters*, 195:1-8 (2001).
Baig et al., "cry Genes profiling and the toxicity of isolates of *Bacillus thuringiensis* from soil samples against American bollworm, *Helicoverpa armigera*," *Journal of Applied Microbiology*, 109:1967-1978 (2010).
Bravo et al., "Mode of action of *Bacillus thuringiensis* Cry and Cyt toxins and their potential for insect control," *Toxins*, 49:423-435 (2007).
Database UniProt, Database accession No. D9U3MO (2010).
De Maagd et al., "*Bacillus thuringiensis* delta-endotoxin Cry1C domain III Can Function as a Specificity Determinant for *Spodoptera exigua* in Different, but Not All, Cry1-Cry1C Hybrids," *Applied and Environmental Microbiology*, 66(4):1559-1563 (2000).
Della-Cioppa et al., "Translocation of the precursor of 5-enolpyruvylshikimate-3-phosphate synthase into chloroplasts of higher plants in vitro," *Proc. Natl. Acad. Sci. USA*, 83:6873-6877, (1986).
Forgoux-Nicol et al., "Isolation of repeseed genes expressed early and specifically during development of the male gametophyte," *Plant Molecular Biology*, 40:857-872 (1999).
Herrero et al., "Mutations in the *Bacillus thuringiensis* Cry1Ca toxin demonstrate the role of domains II and III in specificity towards *Spodoptera exigua* larvae," *Biochem J.*, 384:507-513 (2004).
International Search Report dated Jun. 6, 2016, in International Patent Application No. PCT US2015/055800.
IUPAC-IUB Joint Commission on Biochemical Nomenclature, "Nomenclature and Symbolism for Amino Acids and Peptides," *Eur. J. Biochem.* 138:9-37(1984).
Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet*, 210:437-442 (1987).
Knight et al., "A Strategy for Shuffling Numerous *Bacillus thuringiensis* Crystal Protein Domains," *Journal of Economic Entomology*, 97:1805-1813 (2004).
James, "Global Status of Commercialized Biotech/GM Crops: 2012," *ISAAA*, Brief No. 44 (2012).
Lucena et al., "Molecular Approaches to Improve the Insecticidal Activity of Bacillus thuringiensis Cry toxins," *Toxins*, 6(8):2393-2423 (2014).
Pardo-Lopez et al., "Strategies to improve the insecticidal activity of Cry toxins from *Bacillus thuringiensis*," *Peptides*, 30:589-595 (2009).
Pardo-Lopez et al., "*Bacillus thuringiensis* insecticidal three-domain Cry toxins: mode of action, insect resistance and consequences for crop protection," *FEMS Microbiology Reviews*, 37:3-22 (2013).
Thompson et al., "CLUSTAL W: improving the sensitivity of progressive multiple sequence alignment through sequence weighting, position-specific gap penalties and weight matrix choice," *Nucleic Acids Research*, 22:4673-4680 (1994).
Perlak of al., Insect Resistant Cotton Plants, *FEMS Microbiology Reviews*, 37:3-22 (2013).
Hernandez-Rodriguez et al., "Shared Midgut Binding Sites for Cry1A.105, Cry1Aa, Cry1Ab, Cry1Ac and Cry1Fa Proteins from Bacillus thuringiensis in Two Important Corn Pests, Ostrinia nubilalis and Spodoptera frugiperda", *PLOS One*, 8(7): e68164:1-9 (2013).

* cited by examiner

SEQUENCE LISTING

```
<160> NUMBER OF SEQ ID NOS: 53

<210> SEQ ID NO 1
<211> LENGTH: 3570
<212> TYPE: DNA
<213> ORGANISM: Artificial
<220> FEATURE:
<223> OTHER INFORMATION: Recombinant nucleotide sequence used for
      expression in a bacterial cell encoding TIC1100.

<400> SEQUENCE: 1
atggagatag tgaataatca gaatcaatgc gtgccttata attgtttgaa taatcccgaa      60
atcgaaatat tagaaggcgg aagaatatca gttggtaata ccccaattga tatttctctt     120
tcgcttactc agtttctttt gagtgaattt gtcccaggtg cggggtttgt attaggatta     180
attgatttaa tatggggatt tgtaggtcct tcccaatggg acgcatttct tgctcaagtg     240
gaacagttaa ttaaccaaag aatagcagaa gctgtaagaa atacagcaat tcaggaatta     300
gagggaatgg cacgggttta tagaacctat gctactgctt ttgctgagtg ggaaaaagct     360
cctgatgacc cagagctaag agaagcacta cgtacacaat ttacagcaac tgagacttat     420
ataagtggaa gaatatccgt tttaaaaatt caaactttg aagtacagct gttatcagtg     480
tttgcccaag ctgcaaattt acatttatct ttattaagag acgttgtgtt ttttgggcaa     540
agatggggtt tttcaacgac aaccgtaaat aattactaca atgatttaac agaagggatt     600
agtacctata cagattatgc tgtacgctgg tacaatacgg gattagaacg tgtatgggga     660
ccggattcta gagattgggt aaggtataat caatttagaa gagaattaac actaactgta     720
```

-continued

```
ttagatatcg ttgctctgtt cccgaattat gatagtagaa gatatccaat tcgaacagtt    780
tcccaattaa caagagaaat ttatacaaac ccagtattag aaaattttga tggtagtttt    840
cgaggctcgg ctcagggcat agaaagaagt attaggagtc cacatttgat ggatatactt    900
aacagtataa ccatctatac ggatgctcat agggggttatt attattggtc agggcatcaa    960
ataatggctt ctcctgtcgg ttttttcgggg ccagaattca cgtttccgct atatggaacc   1020
atgggaaatg cagctccaca acaacgtatt gttgctcaac taggtcaggg cgtgtataga   1080
acattatcgt ccactttata tagaagacct tttaatatag ggataaataa tcaacaacta   1140
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attaatcaaa tacctttagt gaaaggattt   1440
agagtttggg ggggcacctc tgtcattaca ggaccaggat ttacaggagg ggatatcctt   1500
cgaagaaata cctttggtga ttttgtatct ctacaagtca atattaattc accaattacc   1560
caaagatacc gtttaagatt tcgttacgct tccagtaggg atgcacgagt tatagtatta   1620
acaggagcgg catccacagg agtgggaggc caagttagtg taaatatgcc tcttcagaaa   1680
actatggaaa taggggagaa cttaacatct agaacattta gatataccga ttttagtaat   1740
cctttttcat ttagagctaa tccagatata attgggataa gtgaacaacc tctatttggt   1800
gcaggttcta ttagtagcgg tgaactttat atagataaaa ttgaaattat tctagcagat   1860
gcaacatttg aagcagaatc tgatttagaa agagcgcaga aggcggtgaa tgcgctgttt   1920
acgtctacaa accaactagg gctaaaaaca aatgtaacgg attatcatat tgatcaagtg   1980
tccaatttag ttacgtattt atcggatgaa ttttgtctgg atgaaaagcg agaattgtcc   2040
gagaaagtca aacatgcgaa gcgactcagt gatgaacgca atttactcca agattcaaat   2100
ttcaaagaca ttaataggca accagaacgt gggtggggcg gaagtacagg gattaccatc   2160
caaggagggg atgacgtatt taaagaaaat tacgtcacac tatcaggtac ctttgatgag   2220
tgctatccaa catatttgta tcaaaaaatc gatgaatcaa aattaaaagc ctttacccgt   2280
tatcaattaa gagggtatat cgaagatagt caagacttag aaatctattt aattcgctac   2340
aatgcaaaac atgaaacagt aaatgtgcca ggtacgggtt ccttatggcc gctttcagcc   2400
caaagtccaa tcggaaagtg tggagagccg aatcgatgcg cgccacacct tgaatggaat   2460
cctgacttag attgttcgtg tagggatgga gaaaagtgtg cccatcattc gcatcatttc   2520
tccttagaca ttgatgtagg atgtacagac ttaaatgagg acctaggtgt atgggtgatc   2580
tttaagatta agacgcaaga tgggcacgca agactaggga atctagagtt tctcgaagag   2640
aaaccattag taggagaagc gctagctcgt gtgaaaagag cggagaaaaa atggagagac   2700
aaacgtgaaa aattggaatg ggaaacaaat atcgtttata aagaggcaaa agaatctgta   2760
gatgctttat ttgtaaactc tcaatatgat caattacaag cggatacgaa tattgccatg   2820
attcatgcgg cagataaacg tgttcatagc attcgagaag cttatctgcc tgagctgtct   2880
gtgattccgg gtgtcaatgc ggctattttt gaagaattag aagggcgtat tttcactgca   2940
ttctccctat atgatgcgag aaatgtcatt aaaaatggtg attttaataa tggcttatcc   3000
tgctggaacg tgaaagggca gtagatgta gaagaacaaa acaaccaacg ttcggtcctt   3060
gttgttccgg aatgggaagc agaagtgtca caagaagttc gtgtctgtcc gggtcgtggc   3120
```

```
tatatccttc gtgtcacagc gtacaaggag ggatatggag aaggttgcgt aaccattcat    3180
gagatcgaga acaatacaga cgaactgaag tttagcaact gcgtagaaga ggaaatctat    3240
ccaaataaca cggtaacgtg taatgattat actgtaaatc aagaagaata cggaggtgcg    3300
tacacttctc gtaatcgagg atataacgaa gctccttccg taccagctga ttatgcgtca    3360
gtctatgaag aaaaatcgta tacagatgga cgaagagaga atccttgtga atttaacaga    3420
gggtataggg attacacgcc actaccagtt ggttatgtga caaaagaatt agaatacttc    3480
ccagaaaccg ataaggtatg gattgagatt ggagaaacgg aaggaacatt tatcgtggac    3540
agcgtggaat tactccttat ggaggaatga                                     3570
```

<210> SEQ ID NO 2
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 2

```
atggagattg tgaacaacca gaaccagtgc gttccttaca actgcttgaa caaccctgag      60
attgagattc ttgagggtgg tagaatttct gttggcaaca ctcctattga catctctttg     120
agtttgactc aattccttgtt gagtgagttc gttcctggtg ctggtttcgt cttgggtttg    180
attgatttga tttggggttt cgttggtcct agtcaatggg atgctttctt ggctcaagtt     240
gagcaattga ttaaccagag gatcgctgag gctgtgagga acactgctat tcaagagttg     300
gagggtatgg ctagagttta cagaacttac gctactgctt tcgctgagtg ggagaaggct     360
cctgatgacc tgagttgag ggaggctttg agaactcaat tcactgctac tgagacttac     420
atcagtggta gaatcagtgt cttgaagatt caaactttcg aggttcaatt gctttctgtg     480
ttcgctcaag ctgcaaactt gcacttgtct ttgcttagag atgttgtgtt ctttggtcaa     540
agatggggtt ctccactac taccgtgaac aattactaca acgatttgac tgagggtatt     600
tctacttaca ctgattacgc tgttagatgg tacaacactg gttgagagag agtttggggt    660
ccagattcca gagattgggt cagatacaac cagttcagaa gggagttgac tttgactgtc     720
ttggacattg ttgctctctt ccctaactac gatagtcgtc gttacccctat agaactgtt    780 tctcaactta ctagggaaat ctacactaac cctgttcttg agaacttcga tggtagtttc     840
cgtggtagtg ctcaagggat tgagcgttct attcgttctc ctcatcttat ggacattctt    900
aactctatta ctatctacac tgatgctcat cgtggttact attactggtc tggtcatcaa    960 attatgcta gtcctgttgg tttcagtggt cctgagttca ctttccctct ttacggtact    1020
atgggcaacg ctgcacctca acagaggatc gttgctcaac ttggtcaagg tgtttacagg   1080
actctttctt caacccttta caggcgtcct ttcaacattg ggatcaacaa ccagcagctt   1140
tctgttcttg atggaaccga gttcgcttac ggaacctctt caaaccttcc tagtgctgtt   1200
tacaggaagt ctggaaccgt tgacagtctt gatgagattc caccgcagaa caataacgtt   1260
ccacccaggc aaggcttcag tcataggctt tctcatgttt ctatgttccg ctctggattc   1320
agcaactctt cagtttctat tatcagggct ccaatgttct cgtggattca taggtctgcc   1380
gagttcaaca acattatcgc ttccgatagc attaaccaga ttccacttgt taagggattc   1440
cgtgtttggg gaggcacctc tgttattacc ggaccaggct tcaccggagg cgacattctt   1500
cgtcgtaaca ccttcggaga tttcgttcca cttcaagtga acattaactc accaatcacc   1560
```

```
cagcgctaca ggcttcgctt ccgctacgca tcatccaggg atgcaagggt gatcgtgctt    1620
accggagcag cctcaaccgg agtgggaggc caagtgagcg tgaacatgcc acttcagaag    1680
acgatggaga tcggcgagaa ccttacctca agaaccttc gttacaccga tttcagcaac    1740
ccattcagct ttcgtgcaaa cccagacatc atagggatct cagagcagcc actgtttgga    1800
gctggatcaa tctcatccgg agagctttac atcgacaaga tcgagatcat actcgcagat    1860
gcaaccttcg aggctgagag cgatctggag cgtgcacaga aggcagtgaa cgcactcttt    1920
acctctacca accagctcgg actcaagacc aacgtgaccg attaccacat cgaccaagtg    1980
agcaacctcg tgacctacct ctcagatgag ttctgcttgg atgagaaacg cgaactcagc    2040
gagaaggtga agcacgcaaa gcgtctctca gatgagcgta acctcctcca ggatagcaat    2100
ttcaaggaca tcaatcgtca gccagagcgt ggatggggag gctcaaccgg aatcaccatc    2160
cagggaggcg atgatgtgtt taaggagaat tacgtgacac tctccggaac attcgatgag    2220
tgctacccaa catacctcta tcagaagatc gacgagtcca agctcaaggc gttcacccgt    2280
tatcagctcc gtggctacat cgaggatagt caagacctgg aaatctacct catccgctac    2340
aatgcaaagc acgagacagt gaatgtgcca ggaacaggct ccctctggcc actctccgca    2400
cagtctccaa tcggcaagtg cggcgagcca atcgctgcg cgccacacct ggagtggaat    2460
cccgacctgg actgctcctg ccgcgacggc gagaagtgcg cccaccactc ccaccacttt    2520
agcctggaca tcgacgtggg ctgtacagac ctgaatgagg atctgggcgt gtgggtgatc    2580
tttaagatca agacacagga cggccacgcc cgcctgggca atctggagtt tctggaggag    2640
aagcctctgg tgggcgaagc cctggcccgc gtgaagcgcg ccgagaagaa atggcgcgac    2700
aaacgcgaga aactggaatg ggaaacaaac atcgtgtaca agaagccaa agaatccgtg    2760 gacgccctat ttgtgaactc ccagtatgac cagctacagg ccgacacaaa catcgcgatg    2820
atccacgctg cggacaagcg cgtgcactcc atacgcgaag cctatctacc cgaactatcc    2880 gtgataccg gcgtcaatgc cgcgatcttt gaagaattgg aaggccgcat cttcacagcc    2940
tttagcctct atgacgcccg aaatgtcatc aagaatggcg actttaacaa tgggctatcc    3000
tgttggaatg tcaaagggca cgtggacgtc gaagagcaga acaatcagcg atccgtctta    3060
gtcgtacccg aatgggaagc cgaagtctcc caggaagtcc gagtctgtcc tggtagaggt    3120
tacatcttga gagtgactgc ttacaaggag ggttacggtg agggatgcgt gactattcac    3180
gagattgaga caacactga tgagttgaag ttcagtaact gcgtggagga ggaaatctac    3240
cccaacaaca ctgtgacttg taacgattac accgtgaacc aggaggaata cggaggcgct    3300
tacacctcca gaaaccgtgg atacaatgag gctccctcgg tccccgctga ttatgcctcc    3360
gtctatgagg agaagtccta caccgatgga aggcgcgaga tccctgcga gttcaatcgc    3420 ggctatcgag actacactcc gctacccgtt ggctatgtca caaaggaact ggaatacttc    3480
ccggaaacag acaaagtctg gatcgaaatc ggcgaaacag aagggacgtt catagtcgat    3540
agcgtagaac ttctccttat ggaagaatga                                   3570
```

<210> SEQ ID NO 3
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 3

-continued

```
atggagattg tgaacaacca gaaccagtgc gttccttaca actgcttgaa caaccctgag      60
attgagattc ttgagggtgg tagaatttct gttggcaaca ctcctattga catctctttg     120
agtttgactc aattcttgtt gagtgagttc gttcctggtg ctggttcgt cttgggtttg      180 attgatttga tttggggttt cgttggtcct agtcaatggg atgctttctt ggctcaagtt     240
gagcaattga ttaaccagag gatcgctgag gctgtgagga cactgctat tcaagagttg      300 gagggtatgg ctagagttta cagaacttac gctactgctt tcgctgagtg ggagaaggct     360
cctgatgacc ctgagttgag ggaggctttg agaactcaat tcactgctac tgagacttac     420
atcagtggta gaatcagtgt cttgaagatt caaactttcg aggttcaatt gctttctgtg     480
ttcgctcaag ctgcaaactt gcacttgtct ttgcttagag atgttgtgtt ctttggtcaa     540
agatggggtt tctccactac taccgtgaac aattactaca acgatttgac tgagggtatt     600
tctacttaca ctgattacgc tgttagatgg tacaacactg gtttggagag agtttggggt     660
ccagattcca gagattgggt cagatacaac cagttcagaa gggagttgac tttgactgtc     720
ttggacattg ttgctctctt ccctaactac gatagtcgtc gttaccctat tagaactgtt     780
tctcaactta ctagggaaat ctacactaac cctgttcttg agaacttcga tggtagtttc     840
cgtggtagtg ctcaagggat tgagcgttct attcgttctc ctcatcttat ggacattctt     900
aactctatta ctatctacac tgatgctcat cgtggttact attactggtc tggtcatcaa     960
attatggcta gtcctgttgg tttcagtggt cctgagttca cttccctct tacggtact     1020 atgggcaacg ctgcacctca acagaggatc gttgctcaac ttggtcaagg tgtttacagg    1080
actctttctt caacccttta caggcgtcct ttcaacattg ggatcaacaa ccagcagctt    1140
tctgttcttg atggaaccga gttcgctac ggaacctctt caaaccttcc tagtgctgtt    1200
tacaggaagt ctggaaccgt tgacagtctt gatgagattc caccgcagaa caataacgtt   1260
ccacccaggc aaggcttcag tcataggctt tctcatgttt ctatgttccg ctctggattc   1320
agcaactctt cagtttctat tatcagggct ccaatgttct cgtggattca taggtctgcc   1380
gagttcaaca acattatcgc ttccgatagc attaaccaga ttccacttgt taagggattc    1440
cgtgtttggg gaggcacctc tgttattacc ggaccaggct tcaccggagg cgacattctt    1500
cgtcgtaaca ccttcggaga tttcgtttca cttcaagtga acattaactc accaatcacc    1560
cagcgctaca ggcttcgctt ccgctacgca tcatccaggg atgcaagggt gatcgtgctt    1620
accggagcag cctcaaccgg agtgggaggc caagtgagcg tgaacatgcc acttcagaag    1680
acgatggaga tcgcgagaa ccttacctca agaaccttc gttacaccga tttcagcaac    1740
ccattcagct ttcgtgcaaa cccagacatc atagggatct cagagcagcc actgtttgga    1800
gctggatcaa tctcatccgg agagctttac atcgacaaga tcgagatcat actcgcagat    1860
gcaaccttcg aggctgagag cgatctggag cgtgcacaga aggcagtgaa cgcactcttt    1920
acctctacca accagctcgg actcaagacc aacgtgaccg attaccacat cgaccaagtg    1980
agcaacctcg tgacctacct ctcagatgag ttctgcttgg atgagaaacg cgaactcagc    2040
gagaaggtga agcacgcaaa gcgtctctca gatgagcgta acctcctcca ggatagcaat    2100
ttcaaggaca tcaatcgtca gccagagcgt ggatggggag gctcaaccgg aatcaccatc    2160
cagggaggcg atgatgtgtt taaggagaat tacgtgacac tctccggaac attcgatgag    2220
tgctacccaa catacctcta tcagaagatc gacgagtcca agctcaaggc gttcacccgt    2280
tatcagctcc gtggctacat cgaggatagt caagacctgg aaatctacct catccgctac    2340
```

-continued

```
aatgcaaagc acgagacagt gaatgtacca ggaacaggct ccctctggcc actctccgca    2400
cagtctccaa tcggcaagtg cggcgagcca atcgctgcg cgccacacct ggagtggaat    2460
cccgacctgg actgctcctg ccgcgacggc gagaagtgcg cccaccactc ccaccacttt    2520
agcctggaca tcgacgtggg ctgtacagac ctgaatgagg atctgggcgt gtgggtgatc    2580
tttaagatca agacacagga cggccacgcc cgcctgggca atctggagtt ctgtggaggag    2640 aagcctctgg tgggcgaagc cctggcccgc gtgaagcgcg ccgagaagaa atggcgcgac    2700
aaacgcgaga aactggaatg gaaacaaac atcgtgtaca agaagccaa agaatccgtg    2760 gacgccctat ttgtgaactc ccagtatgac cagctacagg ccgacacaaa catcgcgatg    2820
atccacgctg cggacaagcg cgtgcactcc atacgcgaag cctatctacc cgaactatcc    2880
gtgataccgg cgtcaatgc cgcgatcttt gaagaattgg aaggccgcat cttcacagcc    2940
tttagcctct atgacgcccg aaatgtcatc aagaatggcg actttaacaa tgggctatcc    3000
tgttggaatg tcaaagggca cgtggacgtc gaagagcaga acaatcagcg atccgtctta    3060
gtcgtacccg aatgggaagc cgaagtctcc caggaagtcc gagtctgtcc tggtagaggt    3120
tacatcttga gagtgactgc ttacaaggag ggttacggtg agggatgcgt gactattcac    3180
gagattgaga acaacactga tgagttgaag ttcagtaact gcgtggagga ggaaatctac    3240
cccaacaaca ctgtgacttg taacgattac accgtgaacc aggaggaata cggaggcgct    3300
tacacctcca gaaaccgtgg atacaatgag gctccctcgg tccccgctga ttatgcctcc    3360
gtctatgagg agaagtccta caccgatgga aggcgcgaga atccctgcga gttcaatcgc    3420
ggctatcgag actacactcc gctacccgtt ggctatgtca caaggaact ggaatacttc    3480 ccggaaacag acaaagtctg gatcgaaatc ggcgaaacag aagggacgtt catagtcgat    3540
agcgtagaac ttctccttat ggaagaatga                                    3570
```

<210> SEQ ID NO 4
<211> LENGTH: 1189
<212> TYPE: PRT
<213> ORGANISM: Artificial
<220> FEATURE:
<223> OTHER INFORMATION: Amino acid sequence of the chimeric protein
     TIC1100.

<400> SEQUENCE: 4

```
Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140
```

```
Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
            500                 505                 510

Val Asn Ile Asn Ser Pro Ile Thr Gln Arg Tyr Arg Leu Arg Phe Arg
        515                 520                 525

Tyr Ala Ser Ser Arg Asp Ala Arg Val Ile Val Leu Thr Gly Ala Ala
    530                 535                 540

Ser Thr Gly Val Gly Gly Gln Val Ser Val Asn Met Pro Leu Gln Lys
545                 550                 555                 560
```

```
Thr Met Glu Ile Gly Glu Asn Leu Thr Ser Arg Thr Phe Arg Tyr Thr
                565             570                 575
Asp Phe Ser Asn Pro Phe Ser Phe Arg Ala Asn Pro Asp Ile Ile Gly
                580             585                 590
Ile Ser Glu Gln Pro Leu Phe Gly Ala Gly Ser Ile Ser Ser Gly Glu
                595             600                 605
Leu Tyr Ile Asp Lys Ile Glu Ile Ile Leu Ala Asp Ala Thr Phe Glu
                610             615                 620
Ala Glu Ser Asp Leu Glu Arg Ala Gln Lys Ala Val Asn Ala Leu Phe
625                 630                 635                 640
Thr Ser Thr Asn Gln Leu Gly Leu Lys Thr Asn Val Thr Asp Tyr His
                645             650                 655
Ile Asp Gln Val Ser Asn Leu Val Thr Tyr Leu Ser Asp Glu Phe Cys
                660             665                 670
Leu Asp Glu Lys Arg Glu Leu Ser Glu Lys Val Lys His Ala Lys Arg
                675             680                 685
Leu Ser Asp Glu Arg Asn Leu Leu Gln Asp Ser Asn Phe Lys Asp Ile
                690             695                 700
Asn Arg Gln Pro Glu Arg Gly Trp Gly Gly Ser Thr Gly Ile Thr Ile
705                 710                 715                 720
Gln Gly Gly Asp Asp Val Phe Lys Glu Asn Tyr Val Thr Leu Ser Gly
                725             730                 735
Thr Phe Asp Glu Cys Tyr Pro Thr Tyr Leu Tyr Gln Lys Ile Asp Glu
                740             745                 750
Ser Lys Leu Lys Ala Phe Thr Arg Tyr Gln Leu Arg Gly Tyr Ile Glu
                755             760                 765
Asp Ser Gln Asp Leu Glu Ile Tyr Leu Ile Arg Tyr Asn Ala Lys His
                770             775                 780
Glu Thr Val Asn Val Pro Gly Thr Gly Ser Leu Trp Pro Leu Ser Ala
785                 790                 795                 800
Gln Ser Pro Ile Gly Lys Cys Gly Glu Pro Asn Arg Cys Ala Pro His
                805             810                 815
Leu Glu Trp Asn Pro Asp Leu Asp Cys Ser Cys Arg Asp Gly Glu Lys
                820             825                 830
Cys Ala His His Ser His His Phe Ser Leu Asp Ile Asp Val Gly Cys
                835             840                 845
Thr Asp Leu Asn Glu Asp Leu Gly Val Trp Val Ile Phe Lys Ile Lys
                850             855                 860
Thr Gln Asp Gly His Ala Arg Leu Gly Asn Leu Glu Phe Leu Glu Glu
865                 870                 875                 880
Lys Pro Leu Val Gly Glu Ala Leu Ala Arg Val Lys Arg Ala Glu Lys
                885             890                 895
Lys Trp Arg Asp Lys Arg Glu Lys Leu Glu Trp Glu Thr Asn Ile Val
                900             905                 910
Tyr Lys Glu Ala Lys Glu Ser Val Asp Ala Leu Phe Val Asn Ser Gln
                915             920                 925
Tyr Asp Gln Leu Gln Ala Asp Thr Asn Ile Ala Met Ile His Ala Ala
                930             935                 940
Asp Lys Arg Val His Ser Ile Arg Glu Ala Tyr Leu Pro Glu Leu Ser
945                 950                 955                 960
Val Ile Pro Gly Val Asn Ala Ala Ile Phe Glu Glu Leu Glu Gly Arg
                965             970                 975
Ile Phe Thr Ala Phe Ser Leu Tyr Asp Ala Arg Asn Val Ile Lys Asn
```

Gly Asp Phe Asn Asn Gly Leu Ser Cys Trp Asn Val Lys Gly His Val
              980                 985                 990
                995                 1000                1005

Asp Val Glu Glu Gln Asn Asn Gln Arg Ser Val Leu Val Val Pro
    1010                1015                1020

Glu Trp Glu Ala Glu Val Ser Gln Glu Val Arg Val Cys Pro Gly
    1025                1030                1035

Arg Gly Tyr Ile Leu Arg Val Thr Ala Tyr Lys Glu Gly Tyr Gly
    1040                1045                1050

Glu Gly Cys Val Thr Ile His Glu Ile Glu Asn Asn Thr Asp Glu
    1055                1060                1065

Leu Lys Phe Ser Asn Cys Val Glu Glu Ile Tyr Pro Asn Asn
    1070                1075                1080

Thr Val Thr Cys Asn Asp Tyr Thr Val Asn Gln Glu Glu Tyr Gly
    1085                1090                1095

Gly Ala Tyr Thr Ser Arg Asn Arg Gly Tyr Asn Glu Ala Pro Ser
    1100                1105                1110

Val Pro Ala Asp Tyr Ala Ser Val Tyr Glu Glu Lys Ser Tyr Thr
    1115                1120                1125

Asp Gly Arg Arg Glu Asn Pro Cys Glu Phe Asn Arg Gly Tyr Arg
    1130                1135                1140

Asp Tyr Thr Pro Leu Pro Val Gly Tyr Val Thr Lys Glu Leu Glu
    1145                1150                1155

Tyr Phe Pro Glu Thr Asp Lys Val Trp Ile Glu Ile Gly Glu Thr
    1160                1165                1170

Glu Gly Thr Phe Ile Val Asp Ser Val Glu Leu Leu Leu Met Glu
    1175                1180                1185

Glu

<210> SEQ ID NO 5
<211> LENGTH: 3672
<212> TYPE: DNA
<213> ORGANISM: Artificial
<220> FEATURE:
<223> OTHER INFORMATION: Recombinant nucleotide sequence used for
      expression in a bacterial cell encoding TIC860.

<400> SEQUENCE: 5
atgacttcaa ataggaaaaa tgagaatgaa attataaatg ctttatcgat tccaacggta      60
tcgaatcctt ccacgcaaat gaatctatca ccagatgctc gtattgaaga tagcttgtgt     120
gtagccgagg tgaacaatat tgatccattt gttagcgcat caacagtcca aacgggtata     180
aacatagctg gtagaatatt gggcgtatta ggtgtgccgt ttgctggaca actagctagt     240
ttttatagtt ttcttgttgg ggaattatgg cctagtggca gagatccatg ggaaattttc     300
ctggaacatg tagaacaact tataagacaa caagtaacag aaaatactag gaatacggct     360
attgctcgat tagaaggtct aggaagaggc tatagatctt accagcaggc tcttgaaact     420
tggttagata ccgaaatga tgcaagatca agaagcatta ttcttgagcg ctatgttgct     480
ttagaacttg acattactac tgctataccg cttttcagaa tacgaaatga agaagttcca     540
ttattaatgg tatatgctca agctgcaaat ttacacctat tattattgag agacgcatcc     600 cttttttggta gtgaatgggg gatggcatct tccgatgtta accaatatta ccaagaacaa     660
atcagatata cagaggaata ttctaaccat tgcgtacaat ggtataatac agggctaaat     720
aacttaagag ggacaaatgc tgaaagttgg ttgcggtata tcaattccg tagagaccta     780

```
acgttagggg tattagattt agtagccota ttcccaagct atgatactcg cacttatcca    840
atcaatacga gtgctcagtt aacaagagaa atttatacag atccaattgg gagaacaaat    900
gcaccttcag gatttgcaag tacgaattgg tttaataata atgcaccatc gttttctgcc    960
atagaggctg ccattttcag gcctccgcat ctacttgatt ttccagaaca acttacaatt   1020
tacagtgcat caagccgttg gagtagcact caacatatga attattgggt gggacatagg   1080
cttaacttcc gcccaatagg agggacatta aatcctcaa cacaaggact tactaataat    1140
acttcaatta atcctgtaac attacagttt acgtctcgag acgtttatag aacagaatca   1200
aatgcaggga caaatatact atttactact cctgtgaatg gagtaccttg gctagatttt   1260
aattttataa accctcagaa tatttatgaa agaggcgcca ctacctacag tcaaccgtat   1320
cagggagttg ggattcaatt atttgattca gaaactgaat taccaccaga aacaacagaa   1380
cgaccaaatt atgaatcata tagtcataga ttatctcata taggactaat cataggaaac   1440
actttgagag caccagtcta ttcttggacg catcgtagtg cagatcgtac gaatacgatt   1500
ggaccaaata gaattaatca aatacctta gtgaaaggat ttagagtttg ggggggcacc    1560
tctgtcatta caggaccagg atttacagga ggggatatcc ttcgaagaaa tacctttggt   1620
gattttgtat ctctacaagt caatattaat tcaccaatta cccaaagata ccgtttaaga   1680
tttcgttacg cttccagtag ggatgcacga gttatagtat taacaggagc ggcatccaca   1740
ggagtgggag gccaagttag tgtaaatatg cctcttcaga aaactatgga aataggggag   1800
aacttaacat ctagaacatt tagatatacc gattttagta atccttttc atttagagct    1860
aatccagata taattgggat aagtgaacaa cctctatttg gtgcaggttc tattagtagc   1920
ggtgaacttt atatagataa aattgaaatt attctagcag atgcaacatt tgaagcagaa   1980
tctgatttag aaagagcgca gaaggcggtg aatgcgctgt ttacgtctac aaaccaacta   2040
gggctaaaaa caaatgtaac ggattatcat attgatcaag tgtccaattt agttacgtat   2100
ttatcggatg aattttgtct ggatgaaaag cgagaattgt ccgagaaagt caaacatgcg   2160
aagcgactca gtgatgaacg caatttactc caagattcaa atttcaaaga cattaatagg   2220
caaccagaac gtgggtgggg cggaagtaca gggattacca tccaaggagg ggatgacgta   2280
tttaaagaaa attacgtcac actatcaggt acctttgatg agtgctatcc aacatatttg   2340
tatcaaaaaa tcgatgaatc aaaattaaaa gcctttaccc gttatcaatt aagagggtat   2400
atcgaagata gtcaagactt agaaatctat ttaattcgct acaatgcaaa acatgaaaca   2460
gtaaatgtgc caggtacggg ttccttatgg ccgctttcag cccaaagtcc aatcggaaag   2520
tgtggagagc cgaatcgatg cgcgccacac cttgaatgga atcctgactt agattgttcg   2580
tgtagggatg gagaaaagtg tgcccatcat tcgcatcatt tctccttaga cattgatgta   2640
ggatgtacag acttaaatga ggacctaggt gtatgggtga tctttaagat taagacgcaa   2700
gatgggcacg caagactagg gaatctagag tttctcgaag agaaaccatt agtaggagaa   2760
gcgctagctc gtgtgaaaag agcggagaaa aaatggagag acaaacgtga aaaattggaa   2820
tgggaaacaa atatcgttta taaagaggca aaagaatctg tagatgcttt atttgtaaac   2880
tctcaatatg atcaattaca agcggatacg aatattgcca tgattcatgc ggcagataaa   2940
cgtgttcata gcattcgaga agcttatctg cctgagctgt ctgtgattcc gggtgtcaat   3000
gcggctattt ttgaagaatt agaagggcgt attttcactg cattctccct atatgatgcg   3060
agaaatgtca ttaaaaatgg tgattttaat aatggcttat cctgctggaa cgtgaaaggg   3120
```

```
catgtagatg tagaagaaca aaacaaccaa cgttcggtcc ttgttgttcc ggaatgggaa    3180
gcagaagtgt cacaagaagt tcgtgtctgt ccgggtcgtg gctatatcct tcgtgtcaca    3240
gcgtacaagg agggatatgg agaaggttgc gtaaccattc atgagatcga gaacaataca    3300
gacgaactga agtttagcaa ctgcgtagaa gaggaaatct atccaaataa cacggtaacg    3360
tgtaatgatt atactgtaaa tcaagaagaa tacggaggtg cgtacacttc tcgtaatcga    3420
ggatataacg aagctccttc cgtaccagct gattatgcgt cagtctatga agaaaaatcg    3480
tatacagatg gacgaagaga gaatccttgt gaatttaaca gagggtatag ggattacacg    3540
ccactaccag ttggttatgt gacaaaagaa ttagaatact tcccagaaac cgataaggta    3600
tggattgaga ttggagaaac ggaaggaaca tttatcgtgg acagcgtgga attactcctt    3660
atggaggaat ag                                                        3672

<210> SEQ ID NO 6
<211> LENGTH: 3672
<212> TYPE: DNA
<213> ORGANISM: Artificial
<220> FEATURE:
<223> OTHER INFORMATION: Synthetic nucleotide sequence designed for
      expression in a plant cell encoding TIC860.

<400> SEQUENCE: 6
atgaccagca accggaagaa cgagaacgag atcatcaacg ccctgagcat cccgaccgtg      60
agcaacccta gcacccagat gaacctgagc cctgacgctc gcatcgagga ctccctctgc     120
gtggctgagg tgaacaacat cgaccgttc gtgtccgcct ccaccgtgca gaccggcatc      180
aacatcgcgg gccgcatcct cggcgtgctc ggcgtgccct tgcgggcca gctcgcctcc     240 ttctactcct cctcgtggg agagctgtgg ccctccggcc gcgacccgtg ggagatcttc      300
ctggagcacg tggagcagct catccgccag caagtcaccg agaacacccg caacaccgcc     360
atcgcccgcc tggagggcct gggccgtggc taccgctcct accagcaagc cctggagacc     420
tggctcgaca accgcaacga cgcccgctcc cgctccatca tcctggagcg ctacgtcgcc     480
ctggaactgg acatcaccac tgccatccca ctcttccgca tcaggaacga ggaggtgcct     540
ctgctgatgg tgtacgccca ggctgcgaac ctgcacctgc tgctgctgcg cgacgcaagc     600 ctgttggct ccgagtgggg tatggcaagc tccgacgtca accagtacta ccaggagcag      660
atccgctaca ccgaggagta cagcaaccac tgcgtccagt ggtacaacac cggtctgaac     720
aatctcagag ggaccaacgc tgagagctgg ctgcgctaca accagttccg gcgggatctg     780 acccctaggtg tcctggatct ggtcgctctg ttcccgagct acgataccag gacgtaccct     840
atcaacacct tgctcagct taccagggag atctacactg atcctatcgg taggactaac     900
gctcctagtg gtttcgccag cactaactgg ttcaacaaca cgcgcctag tttctctgcc      960 atcgaggcgg cgatcttccg gcctcctcac ctcctcgact tcccggagca gcttactatc    1020
tactctgcgt cttcgcggtg gtcttcgact cagcacatga actactgggt tggtcaccgg    1080
cttaacttcc gcccgattgg aggaactctt aacaccagta cgcaaggtct tacgaacaac    1140
acttccatca acccgttac gttgcagttc acgtctcggg acgtttaccg gacggagtcg    1200
aatgctggga cgaacatcct gttcacgaca ccggtgaatg tgttccgtg gcacgttc       1260 aacttcatca acccgcagaa catctacgag cgtggagcaa cgacatactc gcaaccatac    1320
caaggcgttg gcatccaact gtttgactcg gagacggaac tgccaccaga gacgacagaa    1380
cgtccgaatt acgagtcata ctcacacaga ctatcacaca ttggactcat tatcggaaac    1440
```

```
acactgagag caccagtgta ctcatggaca catcggtcag cagatcgtac gaacaccatc    1500
ggacccaatc ggatcaacca gatcccgctc gtgaagggct tccgcgtgtg gggcggcacc    1560
tccgtcatca ccggtccggg cttcaccggc ggcgacatcc tccgccgcaa caccttcggc    1620
gacttcgtgt cactccaagt gaacatcaac agcccgatca cccagcgcta tcgcctccgc    1680
ttccgctacg cctcctcccg cgacgctaga gtgatcgtgc tcaccggagc ggcgtccaca    1740
ggcgtaggcg gccaagtgtc tgtgaacatg ccgctccaga agactatgga gattggtgag    1800
aacctcacct ctcgcacctt ccgctacacc gacttctcca atccgttctc cttcagagcc    1860
aacccagaca tcatcggcat ctccgagcag cctctctttg gcgctggctc catctcctcc    1920
ggcgagctgt acatcgacaa gattgagatc atccttgccg acgccacctt cgaagctgag    1980
tccgatctcg agcgcgccca gaaggccgtg aacgccctct tcactagcac taaccagctc    2040
ggcctcaaga ctaacgtgac cgactaccac attgaccaag tgagcaacct agtgacctac    2100
cttagcgacg agttctgcct tgacgagaag cgtgagctga gcgagaaggt gaagcacgcc    2160
aagcgcctct ccgacgagcg caacctcctc caggactcca acttcaagga catcaaccgc    2220
cagcccgagc gcggctgggg cggtagcacc ggcatcacca tccagggcgg tgacgatgtg    2280
ttcaaggaga actacgtgac cctctccggc accttcgacg agtgctaccc gacctaccct    2340
taccagaaga tcgacgagtc caagctcaag gcgttcaccc gctaccagct tcgcggctac    2400
atcgaggact cccaggatct ggagatctac ctcatccgct acaacgccaa gcacgagacc    2460
gtgaacgtgc ccggcaccgg ctccctctgg ccgctctccg cccagagccc tatcggcaag    2520
tgcggcgagc ccaaccgctg cgcgcctcac ctggagtgga accctgacct cgactgctcc    2580
tgccgcgacg gcgagaagtg cgcccaccat agccaccact tctctctcga catcgacgtg    2640
ggctgcaccg acctcaacga ggatctgggc gtgtgggtga tcttcaagat caagacccag    2700
gacggccacg ccaggctggg caacctggag ttcctggagg agaagcctct ggtgggtgag    2760
gccctggcca gggtcaagag ggctgagaag aaatggaggg acaagaggga gaagctggag    2820
tgggagacca acatcgtgta caaggaggct aaggagtccg tggacgctct gttcgtcaac    2880
tctcagtacg atcagctcca ggctgacacc aacatcgcta tgatccacgc tgcggataag    2940
agggtccact ctatcaggga ggcttacctg cctgagcttt ctgtcatccc tggtgtcaac    3000
gcggcaatct tcgaggaact tgagggccgc atcttcactg cgttctcgct ttacgatgcg    3060
cggaacgtca ttaagaacgg tgacttcaac aatggtcttt cgtgctggaa cgtcaagggt    3120
catgtcgatg tcgaggaaca gaacaaccag cggtcggtcc ttgtcgttcc cgagtgggag    3180
gccgaggtct cgcaagaggt ccgggtctgc cctgggcgcg ggtacattct tcgtgtcact    3240
gcgtacaagg agggctacgg cgagggctgc gttactattc atgagattga gaacaatacg    3300
gatgagctta agtttagtaa ctgtgttgag gaggagatct acccgaacaa tacggttacg    3360
tgcaatgatt acacggtgaa ccaggaggaa tacggcggag catacacctc acgtaataga    3420
gggtacaatg aggcaccgtc agttccggca gattatgcct cagtttatga ggagaagtcc    3480
tacacggatg gaagacgcga gaatccatgt gagtttaata gaggataccg agactacaca    3540
ccactcccag ttggatacgt tacaaaggag ttggaatact tcccagaaac agataaagtt    3600
tggatagaga tcggagaaac agaaggaacc ttcatcgtgg acagtgtaga actgctgctg    3660
atggaagaat ga                                                       3672

<210> SEQ ID NO 7
<211> LENGTH: 1223
```

```
<212> TYPE: PRT
<213> ORGANISM: Artificial
<220> FEATURE:
<223> OTHER INFORMATION: Amino acid sequence of the chimeric protein
      TIC860.

<400> SEQUENCE: 7

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
                20                  25                  30

Ala Arg Ile Glu Asp Ser Leu Cys Val Ala Glu Val Asn Asn Ile Asp
            35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asn Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Trp Gly Met
            195                 200                 205

Ala Ser Ser Asp Val Asn Gln Tyr Tyr Gln Glu Gln Ile Arg Tyr Thr
210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Thr Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Thr Gln His
                340                 345                 350

Met Asn Tyr Trp Val Gly His Arg Leu Asn Phe Arg Pro Ile Gly Gly
            355                 360                 365

Thr Leu Asn Thr Ser Thr Gln Gly Leu Thr Asn Asn Thr Ser Ile Asn
370                 375                 380
```

```
Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
            405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
            435                 440                 445

Asp Ser Glu Thr Glu Leu Pro Pro Glu Thr Thr Glu Arg Pro Asn Tyr
        450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Asn Gln Ile Pro Leu Val Lys
                500                 505                 510

Gly Phe Arg Val Trp Gly Gly Thr Ser Val Ile Thr Gly Pro Gly Phe
            515                 520                 525

Thr Gly Gly Asp Ile Leu Arg Arg Asn Thr Phe Gly Asp Phe Val Ser
530                 535                 540

Leu Gln Val Asn Ile Asn Ser Pro Ile Thr Gln Arg Tyr Arg Leu Arg
545                 550                 555                 560

Phe Arg Tyr Ala Ser Ser Arg Asp Ala Arg Val Ile Val Leu Thr Gly
                565                 570                 575

Ala Ala Ser Thr Gly Val Gly Gly Gln Val Ser Val Asn Met Pro Leu
            580                 585                 590

Gln Lys Thr Met Glu Ile Gly Glu Asn Leu Thr Ser Arg Thr Phe Arg
            595                 600                 605

Tyr Thr Asp Phe Ser Asn Pro Phe Ser Phe Arg Ala Asn Pro Asp Ile
        610                 615                 620

Ile Gly Ile Ser Glu Gln Pro Leu Phe Gly Ala Gly Ser Ile Ser Ser
625                 630                 635                 640

Gly Glu Leu Tyr Ile Asp Lys Ile Glu Ile Ile Leu Ala Asp Ala Thr
                645                 650                 655

Phe Glu Ala Glu Ser Asp Leu Glu Arg Ala Gln Lys Ala Val Asn Ala
            660                 665                 670

Leu Phe Thr Ser Thr Asn Gln Leu Gly Leu Lys Thr Asn Val Thr Asp
            675                 680                 685

Tyr His Ile Asp Gln Val Ser Asn Leu Val Thr Tyr Leu Ser Asp Glu
        690                 695                 700

Phe Cys Leu Asp Glu Lys Arg Glu Leu Ser Glu Lys Val Lys His Ala
705                 710                 715                 720

Lys Arg Leu Ser Asp Glu Arg Asn Leu Leu Gln Asp Ser Asn Phe Lys
                725                 730                 735

Asp Ile Asn Arg Gln Pro Glu Arg Gly Trp Gly Gly Ser Thr Gly Ile
            740                 745                 750

Thr Ile Gln Gly Gly Asp Asp Val Phe Lys Glu Asn Tyr Val Thr Leu
            755                 760                 765

Ser Gly Thr Phe Asp Glu Cys Tyr Pro Thr Tyr Leu Tyr Gln Lys Ile
        770                 775                 780

Asp Glu Ser Lys Leu Lys Ala Phe Thr Arg Tyr Gln Leu Arg Gly Tyr
785                 790                 795                 800
```

-continued

```
Ile Glu Asp Ser Gln Asp Leu Glu Ile Tyr Leu Ile Arg Tyr Asn Ala
                805                 810                 815

Lys His Glu Thr Val Asn Val Pro Gly Thr Gly Ser Leu Trp Pro Leu
            820                 825                 830

Ser Ala Gln Ser Pro Ile Gly Lys Cys Gly Glu Pro Asn Arg Cys Ala
            835                 840                 845

Pro His Leu Glu Trp Asn Pro Asp Leu Asp Cys Ser Cys Arg Asp Gly
850                 855                 860

Glu Lys Cys Ala His His Ser His His Phe Ser Leu Asp Ile Asp Val
865                 870                 875                 880

Gly Cys Thr Asp Leu Asn Glu Asp Leu Gly Val Trp Val Ile Phe Lys
                885                 890                 895

Ile Lys Thr Gln Asp Gly His Ala Arg Leu Gly Asn Leu Glu Phe Leu
            900                 905                 910

Glu Glu Lys Pro Leu Val Gly Glu Ala Leu Ala Arg Val Lys Arg Ala
            915                 920                 925

Glu Lys Lys Trp Arg Asp Lys Arg Glu Lys Leu Glu Trp Glu Thr Asn
            930                 935                 940

Ile Val Tyr Lys Glu Ala Lys Glu Ser Val Asp Ala Leu Phe Val Asn
945                 950                 955                 960

Ser Gln Tyr Asp Gln Leu Gln Ala Asp Thr Asn Ile Ala Met Ile His
                965                 970                 975

Ala Ala Asp Lys Arg Val His Ser Ile Arg Glu Ala Tyr Leu Pro Glu
            980                 985                 990

Leu Ser Val Ile Pro Gly Val Asn Ala Ala Ile Phe Glu Glu Leu Glu
            995                 1000                1005

Gly Arg Ile Phe Thr Ala Phe Ser Leu Tyr Asp Ala Arg Asn Val
        1010                1015                1020

Ile Lys Asn Gly Asp Phe Asn Asn Gly Leu Ser Cys Trp Asn Val
        1025                1030                1035

Lys Gly His Val Asp Val Glu Glu Gln Asn Asn Gln Arg Ser Val
        1040                1045                1050

Leu Val Val Pro Glu Trp Glu Ala Glu Val Ser Gln Glu Val Arg
        1055                1060                1065

Val Cys Pro Gly Arg Gly Tyr Ile Leu Arg Val Thr Ala Tyr Lys
        1070                1075                1080

Glu Gly Tyr Gly Glu Gly Cys Val Thr Ile His Glu Ile Glu Asn
        1085                1090                1095

Asn Thr Asp Glu Leu Lys Phe Ser Asn Cys Val Glu Glu Ile
        1100                1105                1110

Tyr Pro Asn Asn Thr Val Thr Cys Asn Asp Tyr Thr Val Asn Gln
        1115                1120                1125

Glu Glu Tyr Gly Gly Ala Tyr Thr Ser Arg Asn Arg Gly Tyr Asn
        1130                1135                1140

Glu Ala Pro Ser Val Pro Ala Asp Tyr Ala Ser Val Tyr Glu Glu
        1145                1150                1155

Lys Ser Tyr Thr Asp Gly Arg Arg Glu Asn Pro Cys Glu Phe Asn
        1160                1165                1170

Arg Gly Tyr Arg Asp Tyr Thr Pro Leu Pro Val Gly Tyr Val Thr
        1175                1180                1185

Lys Glu Leu Glu Tyr Phe Pro Glu Thr Asp Lys Val Trp Ile Glu
        1190                1195                1200

Ile Gly Glu Thr Glu Gly Thr Phe Ile Val Asp Ser Val Glu Leu
```

Leu Leu  Met Glu Glu
    1220

<210> SEQ ID NO 8
<211> LENGTH: 3564
<212> TYPE: DNA
<213> ORGANISM: Artificial
<220> FEATURE:
<223> OTHER INFORMATION: Recombinant nucleotide sequence used for
      expression in a bacterial cell encoding TIC867.

<400> SEQUENCE: 8

| | |
|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca aacgggtatt | 180 |
| aacatagctg gtagaatact aggtgtatta ggcgtaccgt tgctggaca aatagctagt | 240 |
| ttttatagtt ttcttgttgg tgaattatgg ccccgcggca gagatccttg ggaaattttc | 300 |
| ctagaacatg tcgaacaact tataagacaa caagtaacag aaaatactag ggatacggct | 360 |
| cttgctcgat tacaaggttt aggaaattcc tttagagcct atcaacagtc acttgaagat | 420 |
| tggctagaaa accgtgatga tgcaagaacg agaagtgttc tttataccca atatatagcc | 480 |
| ttagaacttg attttcttaa tgcgatgccg cttttcgcaa ttagaaacca gaagttcca | 540 |
| ttattaatgg tatatgctca agctgcaaat ttacacctat tattattgag agatgcctct | 600 |
| ctttttggta gtgaatttgg gcttacatcc caagaaattc aacgttatta tgagcgccaa | 660 |
| gtggaaaaaa cgagagaata ttctgattat tgcgcaagat ggtataatac gggtttaaat | 720 |
| aatttgagag gacaaatgc tgaaagttgg ttgcgtatata atcaattccg tagagactta | 780 |
| acgctaggag tattagatct agtggcacta ttcccaagct atgacacgcg tgtttatcca | 840 |
| atgaatacca gtgctcaatt aacaagagaa atttatacag atccaattgg agaacaaat | 900 |
| gcaccttcag gatttgcaag tacgaattgg tttaataata tgcaccatc gttttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |
| gtggggacac aactatttga ttcagaaact gaattaccac cagaaacaac agaacgacca | 1380 |
| aattatgaat cttacagtca tagattatct aatataagac taatatcagg aaacactttg | 1440 |
| agagcaccag tatattcttg gacgcaccgt agtgcagatc gtacaaatac cattagttca | 1500 |
| gatagcatta cacaaatacc attggtaaag gcgcataccc tccaatcggg taccactgta | 1560 |
| gtaaaagggc cagggtttac aggagggggat atcctccgtc gaacaagtgg aggaccattt | 1620 |
| gcttttagta tgttaatct agattttaac ttgtcacaaa ggtatcgtgc tagaattcgt | 1680 |
| tatgcctcta ctactaacct aagaatttac gtaacggttg caggtgaacg aattttttgct | 1740 |
| ggtcaatttg acaaaactat ggatgctggt gccccattaa cattccaatc ttttagttac | 1800 |
| gcaactatta tacagctttt acattccca gaaagatcga gcagcttgac tgtaggtgcc | 1860 |
| gatacgttta gttcaggtaa tgaagtttat gtagatagat ttgaattaat cccagttact | 1920 |

```
gcaaccttcg aggcagaatc tgatttagaa agagcacaaa aggcggtgaa tgagctgttt    1980
acttcttcca atcaaatcgg gttaaaaaca gatgtgacgg attatcatat tgatcaagta    2040
tccaatttag ttgagtgttt atctgatgaa ttttgtctgg atgaaaaaaa agaattgtcc    2100
gagaaagtca acatgcgaa gcgacttagt gatgagcgga atttacttca agatccaaac    2160
tttagaggga tcaatagaca actagaccgt ggctggagag aagtacgga tattaccatc    2220 caaggaggcg atgacgtatt caaagagaat tacgttacgc tattgggtac ctttgatgag    2280
tgctatccaa cgtatttata tcaaaaaata gatgagtcga aattaaaagc ctatacccgt    2340
taccaattaa gagggtatat cgaagatagt caagacttag aaatctattt aattcgctac    2400
aatgccaaac acgaaacagt aaatgtgcca ggtacgggtt ccttatggcc gctttcagcc    2460
ccaagtccaa tcggaaaatg tgcccatcat tcccatcatt tctccttgga cattgatgtt    2520
ggatgtacag acttaaatga ggacttaggt gtatgggtga tattcaagat taagacgcaa    2580
gatggccatg caagactagg aaatctagaa tttctcgaag agaaaccatt agtaggagaa    2640
gcactagctc gtgtgaaaag agcggagaaa aaatggagag acaaacgtga aaaattggaa    2700
tgggaaacaa atattgttta taagaggca aaagaatctg tagatgcttt atttgtaaac    2760
tctcaatatg atagattaca agcggatacc aacatcgcga tgattcatgc ggcagataaa    2820
cgcgttcata gcattcgaga agcttatctg cctgagctgt ctgtgattcc gggtgtcaat    2880
gcggctattt ttgaagaatt agaagggcgt attttcactg cattctccct atatgatgcg    2940
agaaatgtca ttaaaaatgg tgattttaat aatggcttat cctgctggaa cgtgaaaggg    3000
catgtagatg tagaagaaca aaacaaccac cgttcggtcc ttgttgttcc ggaatgggaa    3060
gcagaagtgt cacaagaagt tcgtgtctgt ccgggtcgtg gctatatcct tcgtgtcaca    3120
gcgtacaagg agggatatgg agaaggttgc gtaaccattc atgagatcga gaacaataca    3180
gacgaactga gtttagcaa ctgtgtagaa gaggaagtat atccaaacaa cacggtaacg    3240
tgtaatgatt atactgcgac tcaagaagaa tatgagggta cgtacacttc tcgtaatcga    3300
ggatatgacg gagcctatga aagcaattct tctgtaccag ctgattatgc atcagcctat    3360
gaagaaaaag catatacaga tggacgaaga gacaatcctt gtgaatcaa cagaggatat    3420 ggggattaca caccactacc agctggctat gtgacaaaag aattagagta cttcccagaa    3480
accgataagg tatggattga gatcggagaa acggaaggaa cattcatcgt ggacagcgtg    3540
gaattacttc ttatggagga atag                                           3564
```

<210> SEQ ID NO 9
<211> LENGTH: 3564
<212> TYPE: DNA
<213> ORGANISM: Artificial
<220> FEATURE:
<223> OTHER INFORMATION: Synthetic nucleotide sequence designed for expression in a plant cell encoding TIC867.

<400> SEQUENCE: 9

```
atgaccagca accgaaagaa cgagaacgag atcatcaacg ccctgtccat accggccgtg      60
tcaaaccact ccgcccagat gaacctctcc accgacgcga ggatcgagga ctccctctgc    120
atcgccgagg gcaacaacat cgacccgttc gtgtctgcaa gcacggtcca gaccggcatc    180
aacatcgcgg gccgcatcct gggcgtgctc ggcgtgccct tcgcgggtca aatcgcctct    240
ttctactcat tcctcgtggg cgagctgtgg ccgcgcggac gtgacccgtg ggaaatcttc    300
ctggagcacg ttgagcagct catccggcag caagtgaccg agaacaccag ggacaccgca    360
```

```
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgacctc    780
acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata cgctccttc tttctctgcc     960 atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc tctgaactc actgcgcggc agccttctct acactatcgg ctacaccggc    1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccttcg aagctgagtc ggacctggag cgtgcacaga aggcagtcaa cgagctgttc   1980
acctctagca accagatcgg cctcaagacc gacgtcacag actaccacat cgaccaagtg   2040
tccaacctgg tcgagtgcct tagcgacgag ttctgcctag acgagaagaa ggagctgtcg   2100
gagaaggtca aacacgccaa gcgtctgagc gatgagcgca acctgctcca agaccctaac   2160
ttccgtggca tcaacaggca gcttgaccgt ggctggcgcg ctcgacgga catcacgatc    2220 cagggtggcg acgacgtatt caaggagaat tacgtgacct tgcttgggac gtttgacgag   2280
tgctatccca cctacctcta ccagaagatt gatgaatcga aattgaaggc gtacacgaga   2340
taccagctcc gtggctacat cgaggacagc caggacttgg agatctacct catacgctac   2400
aacgctaaac atgagaccgt gaacgtccct gggacgggca gtctgtggcc actctctgct   2460
cctagcccta tcggcaagtg cgctcaccac tcgcaccact tcagccttga catcgacgtg   2520
ggatgtactg acctcaacga agacctgggc gtctgggtta tcttcaagat caagacccag   2580 gacgccacg cccgactcgg caacctggag ttcctggagg agaaaccact ggtgggcgag    2640
gcgctcgccc gcgtgaagcg tgccgagaag aagtggcggg acaagaggga gaagctagaa   2700
```

```
tgggagacga acatcgtgta caaggaggcc aaggaaagcg tcgatgccct gttcgtgaac    2760
tcacagtacg accgtctcca ggcggacacg aacatcgcca tgatccacgc ggctgacaag    2820
cgcgtccact ccatccgcga ggcgtactta ccggagctgt cggtgatccc aggcgtaaac    2880
gcggcgatct tcgaggagct agagggacgc atcttcacag cgttcagcct gtacgacgca    2940
cgcaacgtca tcaagaacgg cgatttcaac aacggactgt cctgctggaa cgtgaagggc    3000
cacgtcgatg tcgaggaaca gaacaaccac cgctctgtcc tggtggtccc agagtgggag    3060
gccgaggtct cccaggaggt ccgcgtgtgc cctgggcgtg gctacatcct ccgtgtgaca    3120
gcctacaagg agggctacgg tgagggctgc gtcaccattc acgagatcga gaacaacact    3180
gacgaactca agttctcgaa ttgcgtggag gaggaggtgt acccgaacaa tacggtgacg    3240
tgcaacgact acacggcaac ccaagaggag tacgagggca cctacaccag taggaaccgt    3300
ggctacgacg gtgcctacga gtcgaactcc agcgtccctg cggactacgc cagcgcgtac    3360
gaggagaagg cttacaccga cggacgccgg gacaacccat gcgagagcaa ccgtggctac    3420
ggcgactaca ctcctctccc ggccggatac gtcacaaagg agctggagta tttcccagag    3480
acggacaagg tgtggatcga aatcggagag acagagggaa ccttcatcgt ggacagcgtg    3540
gagctgctcc tcatggagga gtga                                          3564
```

<210> SEQ ID NO 10
<211> LENGTH: 1187
<212> TYPE: PRT
<213> ORGANISM: Artificial
<220> FEATURE:
<223> OTHER INFORMATION: Amino acid sequence of the chimeric protein
      TIC867.

<400> SEQUENCE: 10

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205
```

```
Thr Ser Gln Glu Ile Gln Arg Tyr Tyr Glu Arg Gln Val Glu Lys Thr
    210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Val Tyr Pro Met Asn Thr Ser Ala Gln Leu Thr
            275                 280                 285
Arg Glu Ile Tyr Thr Asp Pro Ile Gly Arg Thr Asn Ala Pro Ser Gly
    290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
    355                 360                 365
Ser Leu Ser Thr Ser Thr His Gly Asn Thr Asn Thr Ser Ile Asn Pro
370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
            435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Thr Gln Ile Pro Leu Val Lys Ala His
                500                 505                 510
Thr Leu Gln Ser Gly Thr Thr Val Val Lys Gly Pro Gly Phe Thr Gly
            515                 520                 525
Gly Asp Ile Leu Arg Arg Thr Ser Gly Gly Pro Phe Ala Phe Ser Asn
    530                 535                 540
Val Asn Leu Asp Phe Asn Leu Ser Gln Arg Tyr Arg Ala Arg Ile Arg
545                 550                 555                 560
Tyr Ala Ser Thr Thr Asn Leu Arg Ile Tyr Val Thr Val Ala Gly Glu
                565                 570                 575
Arg Ile Phe Ala Gly Gln Phe Asp Lys Thr Met Asp Ala Gly Ala Pro
                580                 585                 590
Leu Thr Phe Gln Ser Phe Ser Tyr Ala Thr Ile Asn Thr Ala Phe Thr
            595                 600                 605
Phe Pro Glu Arg Ser Ser Ser Leu Thr Val Gly Ala Asp Thr Phe Ser
    610                 615                 620
```

```
Ser Gly Asn Glu Val Tyr Val Asp Arg Phe Glu Leu Ile Pro Val Thr
625                 630                 635                 640

Ala Thr Phe Glu Ala Glu Ser Asp Leu Glu Arg Ala Gln Lys Ala Val
            645                 650                 655

Asn Glu Leu Phe Thr Ser Ser Asn Gln Ile Gly Leu Lys Thr Asp Val
            660                 665                 670

Thr Asp Tyr His Ile Asp Gln Val Ser Asn Leu Val Glu Cys Leu Ser
        675                 680                 685

Asp Glu Phe Cys Leu Asp Glu Lys Lys Glu Leu Ser Glu Lys Val Lys
690                 695                 700

His Ala Lys Arg Leu Ser Asp Glu Arg Asn Leu Leu Gln Asp Pro Asn
705                 710                 715                 720

Phe Arg Gly Ile Asn Arg Gln Leu Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Leu Gly Thr Phe Asp Glu Cys Tyr Pro Thr Tyr Leu Tyr Gln
        755                 760                 765

Lys Ile Asp Glu Ser Lys Leu Lys Ala Tyr Thr Arg Tyr Gln Leu Arg
770                 775                 780

Gly Tyr Ile Glu Asp Ser Gln Asp Leu Glu Ile Tyr Leu Ile Arg Tyr
785                 790                 795                 800

Asn Ala Lys His Glu Thr Val Asn Val Pro Gly Thr Gly Ser Leu Trp
                805                 810                 815

Pro Leu Ser Ala Pro Ser Pro Ile Gly Lys Cys Ala His His Ser His
            820                 825                 830

His Phe Ser Leu Asp Ile Asp Val Gly Cys Thr Asp Leu Asn Glu Asp
        835                 840                 845

Leu Gly Val Trp Val Ile Phe Lys Ile Lys Thr Gln Asp Gly His Ala
850                 855                 860

Arg Leu Gly Asn Leu Glu Phe Leu Glu Glu Lys Pro Leu Val Gly Glu
865                 870                 875                 880

Ala Leu Ala Arg Val Lys Arg Ala Glu Lys Lys Trp Arg Asp Lys Arg
                885                 890                 895

Glu Lys Leu Glu Trp Glu Thr Asn Ile Val Tyr Lys Glu Ala Lys Glu
            900                 905                 910

Ser Val Asp Ala Leu Phe Val Asn Ser Gln Tyr Asp Arg Leu Gln Ala
        915                 920                 925

Asp Thr Asn Ile Ala Met Ile His Ala Ala Asp Lys Arg Val His Ser
930                 935                 940

Ile Arg Glu Ala Tyr Leu Pro Glu Leu Ser Val Ile Pro Gly Val Asn
945                 950                 955                 960

Ala Ala Ile Phe Glu Glu Leu Glu Gly Arg Ile Phe Thr Ala Phe Ser
                965                 970                 975

Leu Tyr Asp Ala Arg Asn Val Ile Lys Asn Gly Asp Phe Asn Asn Gly
            980                 985                 990

Leu Ser Cys Trp Asn Val Lys Gly His Val Asp Val Glu Glu Gln Asn
        995                 1000                1005

Asn His Arg Ser Val Leu Val Pro Glu Trp Glu Ala Glu Val
        1010                1015                1020

Ser Gln Glu Val Arg Val Cys Pro Gly Arg Gly Tyr Ile Leu Arg
        1025                1030                1035

Val Thr Ala Tyr Lys Glu Gly Tyr Gly Glu Gly Cys Val Thr Ile
```

His Glu Ile Glu Asn Asn Thr Asp Glu Leu Lys Phe Ser Asn Cys
1055               1060                1065

Val Glu Glu Val Tyr Pro Asn Asn Thr Val Thr Cys Asn Asp
1070               1075                1080

Tyr Thr Ala Thr Gln Glu Glu Tyr Glu Gly Thr Tyr Thr Ser Arg
1085               1090                1095

Asn Arg Gly Tyr Asp Gly Ala Tyr Glu Ser Asn Ser Ser Val Pro
1100               1105                1110

Ala Asp Tyr Ala Ser Ala Tyr Glu Glu Lys Ala Tyr Thr Asp Gly
1115               1120                1125

Arg Arg Asp Asn Pro Cys Glu Ser Asn Arg Gly Tyr Gly Asp Tyr
1130               1135                1140

Thr Pro Leu Pro Ala Gly Tyr Val Thr Lys Glu Leu Glu Tyr Phe
1145               1150                1155

Pro Glu Thr Asp Lys Val Trp Ile Glu Ile Gly Glu Thr Glu Gly
1160               1165                1170

Thr Phe Ile Val Asp Ser Val Glu Leu Leu Leu Met Glu Glu
1175               1180                1185

<210> SEQ ID NO 11
<211> LENGTH: 3642
<212> TYPE: DNA
<213> ORGANISM: Artificial
<220> FEATURE:
<223> OTHER INFORMATION: Recombinant nucleotide sequence used for
      expression in a bacterial cell encoding TIC867_20.

<400> SEQUENCE: 11
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca aacgggtatt     180
aacatagctg gtagaatact aggtgtatta ggcgtaccgt ttgctggaca aatagctagt     240 tttatagtt tcttgttgg tgaattatgg ccccgcggca gagatccttg gaaattttc      300 ctagaacatg tcgaacaact tataagacaa caagtaacag aaaatactag ggatacggct     360
cttgctcgat acaaggtttt aggaaattcc tttagagcct atcaacagtc acttgaagat     420
tggctagaaa accgtgatga tgcaagaacg agaagtgttc tttataccca atatatagcc     480
ttagaacttg atttttcttaa tgcgatgccg cttttcgcaa ttagaaacca agaagttcca     540
ttattaatgg tatatgctca agctgcaaat ttacacctat tattattgag agatgcctct     600 cttttttggta gtgaatttgg gcttacatcc caagaaattc aacgttatta tgagcgccaa     660
gtggaaaaaa cgagagaata ttctgattat tgcgcaagat ggtataatac gggtttaaat     720
aatttgagag gacaaatgc tgaaagttgg ttgcgatata atcaattccg tagagactta     780
acgctaggag tattagatct agtggcacta ttcccaagct atgacacgcg tgtttatcca     840
atgaatacca gtgctcaatt aacaagagaa atttatacag atccaattgg gagaacaaat     900
gcaccttcag gatttgcaag tacgaattgg tttaataata atgcaccatc gttttctgcc     960
atagaggctg ccgttattag gcctccgcat ctacttgatt ttccagaaca gcttacaatt    1020
ttcagcgtat taagtcgatg gagtaatact caatatatga attactgggt gggacataga    1080
cttgaatcgc gaacaataag ggggtcatta agtacctcga cacacggaaa taccaatact    1140
tctattaatc ctgtaacatt acagttcaca tctcgagacg tttatagaac agaatcattt    1200

```
gcagggataa atatacttct aactactcct gtgaatggag taccttgggc tagatttaat    1260
tggagaaatc ccctgaattc tcttagaggt agccttctct atactatagg gtatactgga    1320
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta cacaaatacc attggtaaag gcgcataccc tccaatcggg taccactgta    1560
gtaaaagggc cagggtttac aggaggggat atcctccgtc gaacaagtgg aggaccattt    1620
gcttttagta atgttaatct agattttaac ttgtcacaaa ggtatcgtgc tagaattcgt    1680
tatgcctcta ctactaacct aagaatttac gtaacggttg caggtgaacg aattttttgct   1740 ggtcaatttg acaaaactat ggatgctggt gccccattaa cattccaatc ttttagttac    1800
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaacctttg aggcagaata tgatttagaa agagcgcaaa aggtggtgaa tgccctgttt    1980
acgtctacaa accaactagg gctaaaaaca gatgtgacgg attatcatat tgatcaggta    2040
tccaatctag ttgcgtgttt atcggatgaa ttttgtctgg atgaaaagag agaattgtcc    2100
gagaaagtta acatgcaaa gcgactcagt gatgagcgga atttacttca agatccaaac    2160
ttcagaggga tcaataggca accagaccgt ggctggagag aagtacgga tattactatc    2220 caaggaggag atgacgtatt caaagagaat tacgttacgc taccgggtac ctttgatgag    2280
tgctatccaa cgtatttata tcaaaaaata gatgagtcga aattaaaagc ctatacccgt    2340
tatcaattaa gagggtatat cgaagatagt caagacttag aaatctattt aattcgttac    2400
aatgcaaaac acgaaatagt aaatgtacca ggtacaggaa gtttatggcc tctttctgta    2460
gaaaatcaaa ttggaccttg tggagaaccg aatcgatgcg cgccacacct tgaatggaat    2520
cctgatttac actgttcctg cagagacggg gaaaaatgtg cacatcattc tcatcatttc    2580
tctttggaca ttgatgttgg atgtacagac ttaaatgagg acttaggtgt atgggtgata    2640
ttcaagatta agacgcaaga tggccacgca cgactaggga atctagagtt ctcgaagag    2700 aaaccattat taggagaagc actagctcgt gtgaaaagag cggagaaaaa atggagagac    2760
aaacgcgaaa cattacaatt ggaaacaact atcgtttata aagaggcaaa agaatctgta    2820
gatgctttat ttgtaaactc tcaatatgat agattacaag cggatacgaa catcgcgatg    2880
attcatgcgg cagataaacg cgttcataga attcgagaag cgtatctgcc ggagctgtct    2940
gtgattccgg gtgtcaatgc ggctattttt gaagaattag aagagcgtat tttcactgca    3000 tttttccctat atgatgcgag aaatattatt aaaaatggcg atttcaataa tggcttatta    3060
tgctggaacg tgaaagggca tgtagaggta gaagaacaaa acaatcaccg ttcagtcctg    3120
gttatcccag aatgggaggc agaagtgtca caagaggttc gtgtctgtcc aggtcgtggc    3180
tatatccttc gtgttacagc gtacaaagag ggatatggag aaggttgcgt aacgatccat    3240
gagatcgaga acaatacaga cgaactgaaa ttcaacaact gtgtagaaga ggaagtatat    3300
ccaaacaaca cggtaacgtg tattaattat actgcgactc aagaagaata tgagggtacg    3360
tacacttctc gtaatcgagg atatgacgaa gcctatggta ataacccttc cgtaccagct    3420
gattatgcgt cagtctatga agaaaaatcg tatacagata gacgaagaga gaatccttgt    3480
gaatctaaca gaggatatgg agattacaca ccactaccag ctggttatgt aacaaaggaa    3540
```

-continued

| | |
|---|---|
| ttagagtact tcccagagac cgataaggta tggattgaga ttggagaaac agaaggaaca | 3600 |
| ttcatcgtgg acagcgtgga attactcctt atggaggaat ag | 3642 |

<210> SEQ ID NO 12
<211> LENGTH: 3642
<212> TYPE: DNA
<213> ORGANISM: Artificial
<220> FEATURE:
<223> OTHER INFORMATION: Synthetic nucleotide sequence designed for
      expression in a plant cell encoding TIC867_20.

<400> SEQUENCE: 12

| | |
|---|---|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg caacaacat cgacccgttc gtgtctgcaa gcacggtcca gaccggcatc | 180 |
| aacatcgcgg gccgcatcct gggcgtgctc ggcgtgccct cgcgggtca atcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga ccgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgg tgtacgcaca agcagcgaac ctccatctgc tcctgctgcg agacgcatct | 600 |
| ctgttcggca gtgagttcgg gctgacgagc caggagatcc agcgctacta cgagcgccaa | 660 |
| gtggagaaga ctcgtgagta cagcgactac tgcgcgcgct ggtacaacac gggcttgaac | 720 |
| aaccttcgcg gacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |
| atgaacacga gcgcacagct cacccgtgag atctacacag atcccatcgg ccgcaccaac | 900 |
| gctcccagtg gcttcgcaag cacgaattgg ttcaacaata cgctccttc tttctctgcc | 960 |
| atcgaggccg ctgtcatcag accgccgcac ttactcgatt ccccggagca gctcactatc | 1020 |
| ttctctgtgt tgtcccggtg gtcgaacacg cagtacatga actactgggt gggccacagg | 1080 |
| ctagagagcc ggaccatccg tggcagtctc tcaacctcga cccacggcaa cacgaacacg | 1140 |
| agcatcaacc ctgtcactct ccagtttaca tctagggacg tttacaggac agagtcgttc | 1200 |
| gctggcatta acattctgtt gaccactccg gtgaacggcg tcccttgggc ccgcttcaac | 1260 |
| tggaggaatc tctgaactc actgcgcggc agccttctct acactatcgg ctacaccggc | 1320 |
| gttgggacgc aactcttcga ctcggagacc gagctgccgc ccgagaccac cgagcggcct | 1380 |
| aactacgaga gttattcaca caggctctcc aacatccgct tgatttctgg gaacaccttg | 1440 |
| cgggctccgg tgtactcctg gacgcaccgc agcgccgaca gaactaatac catcagctcc | 1500 |
| gactcgatca cccagatccc gctggtgaag gctcacacgc ttcagtcggg caccacagtc | 1560 |
| gtcaagggcc ctggcttcac cggcggcgac atcctgcgtc gcacatctgg cggacccttc | 1620 |
| gccttcagca acgtgaactt ggacttcaat ttgtcacagc ggtatcgtgc cagaatccgg | 1680 |
| tacgccagca ctacgaacct gcgaatctat gttactgtgg cgggcgagcg gatcttcgcc | 1740 |
| gggcaattcg acaagacgat ggacgcggga gcacctctga cattccagtc attctcttac | 1800 |
| gccacgatca acacggcatt cacgtttccg gagcgttcca gtagcctgac cgtgggcgct | 1860 |
| gataccttca gtagcgggaa cgaggtgtac gttgaccgtt cgagctgat cccggtcacc | 1920 |

```
gccaccttcg aggccgagta cgaccttgag cgcgcccaga aggtggtgaa cgccctcttc      1980
actagcacta accagctagg cctgaagact gacgtgaccg actaccacat cgaccaagtg      2040
agcaacctag tggcctgcct ctccgacgag ttctgcctcg acgagaagcg cgagctgtcc      2100
gagaaggtga agcacgccaa cgcctctcc gacgagcgca acctgctcca ggaccccaac       2160
ttcagggca tcaacaggca gcccgaccgc ggctggcgcg gctccaccga catcaccatc       2220
cagggcggtg acgacgtatt caaggagaac tacgttaccc tccccggcac cttcgacgag      2280
tgttacccca cctacctcta ccagaagatc gacgagtcca agctgaaggc ctacacccgc      2340
taccagctcc gcggctacat cgaggactcc caggacctgg aaatctacct catccgctac      2400
aacgccaagc acgagatcgt gaacgtgcct ggcaccggca gcctctggcc tctcagcgtg      2460
gagaaccaga tcggcccttg cggcgagcct aaccgctgcg cccctcacct cgagtggaac      2520
cctgacctcc actgctcgtg cagggacggc gagaagtgcg cccaccatag ccaccacttc      2580
tctctggaca tcgacgtggg ctgcaccgac ctgaacgagg acctgggcgt gtgggttatc      2640
ttcaagatca agacccagga cggtcacgcc aggctgggta acctggagtt ccttgaggaa      2700
aagcctctgc tgggtgaggc cctggccagg gtcaagaggg ctgagaagaa atggagggat      2760
aagagggaga ccctgcagct ggagaccact atcgtctaca aggaggctaa ggagtctgtc      2820
gatgctctgt tcgtcaactc tcagtacgat agactgcaag ctgataccaa catcgctatg      2880
atccacgctg cggataagcg ggtccaccgg atccgggagg cttaccttcc ggagctttct      2940
gtcatcccgg tgtcaacgc tgcgatcttc gaggaacttg aggaacggat cttcactgcg       3000
tttagtcttt acgatgcgcg gaacatcatc aagaacgggg acttcaacaa tggtctgctg      3060
tgctggaacg tcaagggtca tgtcgaggtc gaggaacaaa acaatcatcg tagtgtcctt      3120
gtcattcctg agtgggaggc ggaggtctct caagaggtcc gtgtttgccc ggggcgtggg      3180
tacattcttc gtgttactgc gtacaaggag gggtacgggg aggggtgcgt tactattcat      3240
gagattgaga caatactga tgagcttaag ttcaacaatt gtgttgagga ggaggtttac       3300
ccgaacaata ctgttacgtg catcaactac acggcaacgc aagaggaata cgagggacg      3360
tacacctcgc gtaatagagg gtatgatgag gcgtacggaa acaacccgtc ggttccagca      3420
gattatgcct cggtttatga ggagaagtcg tacacggata cgacgcga gaatccatgt       3480
gagtcaaatc gaggatacgg agattacaca ccattaccag caggatacgt tacaaaggag      3540
ttggaatact ccccggaaac agataaagtt tggattgaaa tcggagaaac agaaggaaca      3600
ttcatcgtcg actcagtaga attgttgttg atggaagaat ga                         3642
```

<210> SEQ ID NO 13
<211> LENGTH: 1213
<212> TYPE: PRT
<213> ORGANISM: Artificial
<220> FEATURE:
<223> OTHER INFORMATION: Amino acid sequence of the chimeric protein
      variant TIC867_20.

<400> SEQUENCE: 13

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly

```
            50                  55                  60
Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                     85                  90                  95

Trp Glu Ile Phe Leu Glu His Val Glu Gln Leu Ile Arg Gln Gln Val
                    100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
                275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
            370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480
```

```
Arg Ala Pro Val Tyr Ser Trp Thr His Arg Ser Ala Asp Arg Thr Asn
            485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
            530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
                580                 585                 590

Leu Thr Phe Gln Ser Phe Ser Tyr Ala Thr Ile Asn Thr Ala Phe Thr
                595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Phe Glu Ala Glu Tyr Asp Leu Glu Arg Ala Gln Lys Val Val
                645                 650                 655

Asn Ala Leu Phe Thr Ser Thr Asn Gln Leu Gly Leu Lys Thr Asp Val
                660                 665                 670

Thr Asp Tyr His Ile Asp Gln Val Ser Asn Leu Val Ala Cys Leu Ser
            675                 680                 685

Asp Glu Phe Cys Leu Asp Glu Lys Arg Glu Leu Ser Glu Lys Val Lys
            690                 695                 700

His Ala Lys Arg Leu Ser Asp Glu Arg Asn Leu Leu Gln Asp Pro Asn
705                 710                 715                 720

Phe Arg Gly Ile Asn Arg Gln Pro Asp Arg Gly Trp Arg Gly Ser Thr
                725                 730                 735

Asp Ile Thr Ile Gln Gly Gly Asp Asp Val Phe Lys Glu Asn Tyr Val
                740                 745                 750

Thr Leu Pro Gly Thr Phe Asp Glu Cys Tyr Pro Thr Tyr Leu Tyr Gln
            755                 760                 765

Lys Ile Asp Glu Ser Lys Leu Lys Ala Tyr Thr Arg Tyr Gln Leu Arg
            770                 775                 780

Gly Tyr Ile Glu Asp Ser Gln Asp Leu Glu Ile Tyr Leu Ile Arg Tyr
785                 790                 795                 800

Asn Ala Lys His Glu Ile Val Asn Val Pro Gly Thr Gly Ser Leu Trp
                805                 810                 815

Pro Leu Ser Val Glu Asn Gln Ile Gly Pro Cys Gly Glu Pro Asn Arg
            820                 825                 830

Cys Ala Pro His Leu Glu Trp Asn Pro Asp Leu His Cys Ser Cys Arg
            835                 840                 845

Asp Gly Glu Lys Cys Ala His His Ser His His Phe Ser Leu Asp Ile
            850                 855                 860

Asp Val Gly Cys Thr Asp Leu Asn Glu Asp Leu Gly Val Trp Val Ile
865                 870                 875                 880

Phe Lys Ile Lys Thr Gln Asp Gly His Ala Arg Leu Gly Asn Leu Glu
                885                 890                 895
```

```
Phe Leu Glu Glu Lys Pro Leu Leu Gly Ala Leu Ala Arg Val Lys
            900                 905                 910

Arg Ala Glu Lys Lys Trp Arg Asp Lys Arg Glu Thr Leu Gln Leu Glu
        915                 920                 925

Thr Thr Ile Val Tyr Lys Glu Ala Lys Glu Ser Val Asp Ala Leu Phe
    930                 935                 940

Val Asn Ser Gln Tyr Asp Arg Leu Gln Ala Asp Thr Asn Ile Ala Met
945                 950                 955                 960

Ile His Ala Ala Asp Lys Arg Val His Arg Ile Arg Glu Ala Tyr Leu
                965                 970                 975

Pro Glu Leu Ser Val Ile Pro Gly Val Asn Ala Ala Ile Phe Glu Glu
            980                 985                 990

Leu Glu Glu Arg Ile Phe Thr Ala Phe Ser Leu Tyr Asp Ala Arg Asn
        995                 1000                1005

Ile Ile Lys Asn Gly Asp Phe Asn Asn Gly Leu Leu Cys Trp Asn
    1010                1015                1020

Val Lys Gly His Val Glu Val Glu Glu Gln Asn Asn His Arg Ser
    1025                1030                1035

Val Leu Val Ile Pro Glu Trp Glu Ala Glu Val Ser Gln Glu Val
    1040                1045                1050

Arg Val Cys Pro Gly Arg Gly Tyr Ile Leu Arg Val Thr Ala Tyr
    1055                1060                1065

Lys Glu Gly Tyr Gly Glu Gly Cys Val Thr Ile His Glu Ile Glu
    1070                1075                1080

Asn Asn Thr Asp Glu Leu Lys Phe Asn Asn Cys Val Glu Glu Glu
    1085                1090                1095

Val Tyr Pro Asn Asn Thr Val Thr Cys Ile Asn Tyr Thr Ala Thr
    1100                1105                1110

Gln Glu Glu Tyr Glu Gly Thr Tyr Thr Ser Arg Asn Arg Gly Tyr
    1115                1120                1125

Asp Glu Ala Tyr Gly Asn Asn Pro Ser Val Pro Ala Asp Tyr Ala
    1130                1135                1140

Ser Val Tyr Glu Glu Lys Ser Tyr Thr Asp Arg Arg Arg Glu Asn
    1145                1150                1155

Pro Cys Glu Ser Asn Arg Gly Tyr Gly Asp Tyr Thr Pro Leu Pro
    1160                1165                1170

Ala Gly Tyr Val Thr Lys Glu Leu Glu Tyr Phe Pro Glu Thr Asp
    1175                1180                1185

Lys Val Trp Ile Glu Ile Gly Glu Thr Glu Gly Thr Phe Ile Val
    1190                1195                1200

Asp Ser Val Glu Leu Leu Leu Met Glu Glu
    1205                1210

<210> SEQ ID NO 14
<211> LENGTH: 3690
<212> TYPE: DNA
<213> ORGANISM: Artificial
<220> FEATURE:
<223> OTHER INFORMATION: Recombinant nucleotide sequence used for
      expression in a bacterial cell encoding TIC867_21.

<400> SEQUENCE: 14
atgacttcaa ataggaaaaa tgagaatgaa attataaatg ctttatcgat tccagctgta    60
tcgaatcatt ccgcacaaat gaatctatca accgatgctc gtattgagga tagcttgtgt   120
atagccgagg ggaacaatat cgatccattt gttagcgcat caacagtcca aacgggtatt   180
```

```
aacatagctg gtagaatact aggtgtatta ggcgtaccgt ttgctggaca aatagctagt      240
ttttatagtt ttcttgttgg tgaattatgg ccccgcggca gagatccttg ggaaattttc      300
ctagaacatg tcgaacaact tataagacaa caagtaacag aaaatactag ggatacggct      360
cttgctcgat tacaaggttt aggaaattcc tttagagcct atcaacagtc acttgaagat      420
tggctagaaa accgtgatga tgcaagaacg agaagtgttc tttataccca atatatagcc      480
ttagaacttg attttcttaa tgcgatgccg cttttcgcaa ttagaaacca agaagttcca      540
ttattaatgg tatatgctca agctgcaaat ttacacctat tattattgag agatgcctct      600 cttttttggta gtgaatttgg gcttacatcc caagaaattc aacgttatta tgagcgccaa      660
gtggaaaaaa cgagagaata ttctgattat tgcgcaagat ggtataatac gggtttaaat      720
aatttgagag gacaaatgc tgaaagttgg ttgcgatata atcaattccg tagagactta      780
acgctaggag tattagatct agtggcacta ttcccaagct atgacacgcg tgtttatcca      840
atgaatacca gtgctcaatt aacaagagaa atttatacag atccaattgg gagaacaaat      900
gcaccttcag gatttgcaag tacgaattgg tttaataata atgcaccatc gttttctgcc      960
atagaggctg ccgttattag gcctccgcat ctacttgatt ttccagaaca gcttacaatt      1020
ttcagcgtat taagtcgatg gagtaatact caatatatga attactgggt gggacataga      1080
cttgaatcgc gaacaataag ggggtcatta agtacctcga cacacggaaa taccaatact      1140
tctattaatc ctgtaacatt acagttcaca tctcgagacg tttatagaac agaatcattt      1200
gcagggataa atatacttct aactactcct gtgaatggag taccttgggc tagatttaat      1260
tggagaaatc ccctgaattc tcttagaggt agccttctct atactatagg gtatactgga      1320
gtggggacac aactatttga ttcagaaact gaattaccac cagaaacaac agaacgacca      1380
aattatgaat cttacagtca tagattatct aatataagac taatatcagg aaacactttg      1440
agagcaccag tatattcttg gacgcaccgt agtgcagatc gtacaaatac cattagttca      1500
gatagcatta cacaaatacc attggtaaag gcgcataccc tccaatcggg taccactgta      1560
gtaaaagggc cagggtttac aggaggggat atcctccgtc gaacaagtgg aggaccattt      1620
gcttttagta atgttaatct agattttaac ttgtcacaaa ggtatcgtgc tagaattcgt      1680
tatgcctcta ctactaacct aagaatttac gtaacggttg caggtgaacg aattttttgct      1740 ggtcaatttg acaaaactat ggatgctggt gccccattaa cattccaatc ttttagttac      1800
gcaactatta atacagcttt tacattccca gaaagatcga gcagcttgac tgtaggtgcc      1860
gatacgttta gttcaggtaa tgaagtttat gtagatagat ttgaattaat cccagttact      1920
gcaaccggaa cgacaaccta tgagtatgaa gagaagcaga atctagaaaa agcgcagaaa      1980
gcgttgaacg ctttgtttac ggatggcacg aatggctatc tacaaatgga tgccactgat      2040
tatgatatca atcaaactgc aaacttaata gaatgtgtat cagatgaatt gtatgcaaaa      2100
gaaaagatag ttttattaga tgaagtcaaa atgcgaagc ggcttagcat atcacgtaac      2160
ctacttttga acgatgattt agaattttca gatggatttg gagaaaacgg atggacgaca      2220
agtgataata tttcaatcca ggcggataat cccctttttta aggggaatta tttaaaaatg      2280
tttggggcaa gagatattga tggaacccta tttccaactt atctctatca aaaaatagat      2340
gagtccaggt taaaaccata tacacgttat cgagtaagag ggtttgtggg aagtagtaaa      2400
aatctaaaat tagtggtaac acgctatgag aaagaaattg atgccattat gaatgttcca      2460
aatgatttgg cacatatgca gcttaaccct tcatgtggag attatcgctg tgaatcatcg      2520
```

| | |
|---|---:|
| tcccagttttt tggtgaacca agtgcatcct acaccaacag ctggatatgc tcttgatatg | 2580 |
| tatgcatgcc cgtcaagttc agataaaaaa catattatgt gtcacgatcg tcatccattt | 2640 |
| gattttcata ttgacaccgg agaattaaat ccaaacacaa acctgggtat tgatgtcttg | 2700 |
| tttaaaattt ctaatccaaa tggatacgct acattaggga atctagaagt cattgaagaa | 2760 |
| ggaccactaa cagatgaagc attggtacat gtaaaacaaa aggaaaagaa atggcgtcag | 2820 |
| cacatggaga aaaacgaat ggaaacacaa caagcctatg atccagcaaa acaagctgta | 2880 |
| gatgcattat ttacaaatga acaagagtta gactatcata ctactttaga tcatattcag | 2940 |
| aacgccgatc agctggtaca ggcgattccc tatgtacacc atgcttggtt accggatgct | 3000 |
| ccaggtatga actatgatgt atatcaaggg ttaaacgcac gtatcatgca ggcgtacaat | 3060 |
| ttatatgatg cacgaaatgt cataataaat ggtgactta cacaaggact acaaggatgg | 3120 |
| cacgcaacag gaaaagcagc ggtacaacaa atagatggag cttcagtatt agttctatca | 3180 |
| aactggagtg ccgaggtatc tcagaatctg catgcccaag atcatcatgg atatatgtta | 3240 |
| cgtgtgattg ccaaaaaaga aggtcctgga aagggtatg taatgatgat ggattttaat | 3300 |
| ggaaagcagg aaacacttac gttcacttct tgtgaagaag gatatataac aaaaacaata | 3360 |
| gaggtattcc cggaaagtga tcgaatacga attgaaatgg gagaaacaga gggtacgttt | 3420 |
| tatgtagata gcatcgagtt gctttgtatg caaggatatg ctagcgataa taacccgcac | 3480 |
| acgggtaata tgtatgagca aagttataat ggaaattata tcaaaatac tagcgatgtg | 3540 |
| tatcaccaag gatatataaa caactataac caaaattcta gtagtatgta taatcaaaat | 3600 |
| tatattaaca atgatgacct gcattccggt tgcacatgta accaagggca taactctggc | 3660 |
| tgtacatgta atcaaggata taaccgttag | 3690 |

<210> SEQ ID NO 15
<211> LENGTH: 3690
<212> TYPE: DNA
<213> ORGANISM: Artificial
<220> FEATURE:
<223> OTHER INFORMATION: Synthetic nucleotide sequence designed for
      expression in a plant cell encoding TIC867_21.

<400> SEQUENCE: 15

| | |
|---|---:|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg gcaacaacat cgacccgttc gtgtctgcaa gcacggtcca gaccggcatc | 180 |
| aacatcgcgg gccgcatcct gggcgtgctc ggcgtgccct cgcgggtca aatcgcctct | 240 |
| ttctactcat tcctcgtggg cgagctgtgg ccgcgcggac gtgaccgtg ggaaatcttc | 300 |
| ctggagcac ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga accgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgg tgtacgcaca agcagcgaac ctccatctgc tcctgctgcg agacgcatct | 600 |
| ctgttcggca gtgagttcgg gctgacgagc caggagatcc agcgctacta cgagcgccaa | 660 |
| gtggagaaga ctcgtgagta cagcgactac tgcgcgcgct ggtacaacac gggcttgaac | 720 |
| aaccttcgcg gacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |

```
atgaacacga gcgcacagct cacccgtgag atctacacag atcccatcgg ccgcaccaac    900
gctcccagtg gcttcgcaag cacgaattgg ttcaacaata acgctccttc tttctctgcc    960
atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc tctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccggga ctaccaccta cgagtacgag gagaagcaga atctcgagaa ggctcagaag   1980
gctctgaacg ctctgttcac tgacgggacc aacggctacc tccagatgga cgccactgac   2040
tacgacatca accagacagc taacctgatt gagtgtgtga gtgacgaact gtacgctaag   2100
gagaagatcg tactcctgga cgaggtgaag tacgctaagc gcctgagcat tagccgtaac   2160
ctgctgctga cgacgatct ggagttcagc gacggctttg gcgagaacgg ctggaccacc   2220
agcgacaaca tctccatcca ggccgacaat ccactcttca aaggcaacta cctcaagatg   2280
ttcggagcca gggacatcga cggcaccctc tttccgacct acctctacca gaagatcgac   2340
gagtcccgcc tcaaacccta cacccgctac agggtgcgcg gcttcgtggg cagcagcaag   2400
aacctcaagc tcgtggtcac acggtatgag aaggagatcg acgccatcat gaacgtgccc   2460
aacgatctcg cccacatgca gctcaatcca tcctgcggcg actaccggtg cgagtccagc   2520
tcccagttcc tcgtgaacca ggtgcaccct actccgaccg ctggctatgc cctggacatg   2580
tacgcctgcc ctagttcctc cgacaagaag cacatcatgt gccacgaccg tcatccgttc   2640
gacttccaca tcgacaccgg cgaactgaac ccgaacacca acctgggcat cgacgtactg   2700
ttcaagattt ccaacccgaa cgggtacgcc accttgggca acctggaggt catcgaagaa   2760
ggcccgctga ccgacgaggc cctggtccac gtcaaacaga aggagaagaa gtggcggcag   2820
cacatggaga agaagcggat ggagactcaa caagcctacg acccggccaa gcaagctgtg   2880
gacgctctgt tcaccaacga gcaagagctt gactaccaca ctactcttga ccacatccag   2940
aatgctgacc agcttgtcca ggctattccg tacgtccacc acgcttggct accggacgct   3000
ccagggatga actacgatgt gtaccagggt ctgaacgcgc ggatcatgca agcgtacaac   3060
ctgtacgacg cgcgtaacgt catcatcaac ggtgacttca ctcagggtct tcaaggttgg   3120
cacgcgactg gcaaagcggc agtccagcag attgatggtg cgtctgttct tgtgttgagc   3180
aactggtctg cggaggtttc tcagaacctg cacgcacagg atcaccacgg ctacatgctg   3240
```

```
aggg tgattg ctaagaagga gggccctggc aaaggctacg tcatgatgat ggacttcaac    3300
ggaaagcaag aaaccctgac cttcactagc tgtgaggagg gctacatcac taagaccatt    3360
gaggtctttc cggagtctga ccgcatccgg atcgagatgg gcgagaccga aggcacgttc    3420
tacgtggact ccatcgaact cctctgcatg caaggctacg cctccgacaa caacccacac    3480
acgggcaaca tgtacgagca gtcctacaac gggaactaca accagaacac ctccgatgtg    3540
taccatcagg gctacatcaa caactacaac cagaacagca gcagcatgta caaccagaac    3600
tacatcaaca cgatgacttt gcactcgggt tgcacctgca accagggtca acagtggg     3660 tgcacgtgca accagggata caaccgttga                                    3690
```

```
<210> SEQ ID NO 16
<211> LENGTH: 1229
<212> TYPE: PRT
<213> ORGANISM: Artificial
<220> FEATURE:
<223> OTHER INFORMATION: Amino acid sequence of the chimeric protein
      variant TIC867_21.

<400> SEQUENCE: 16
```

| Met | Thr | Ser | Asn | Arg | Lys | Asn | Glu | Asn | Glu | Ile | Ile | Asn | Ala | Leu | Ser |
|---|---|---|---|---|---|---|---|---|---|---|---|---|---|---|---|
| 1 | | | | 5 | | | | | 10 | | | | | 15 | |

| Ile | Pro | Ala | Val | Ser | Asn | His | Ser | Ala | Gln | Met | Asn | Leu | Ser | Thr | Asp |
| | | | 20 | | | | | 25 | | | | | 30 | | |

| Ala | Arg | Ile | Glu | Asp | Ser | Leu | Cys | Ile | Ala | Glu | Gly | Asn | Asn | Ile | Asp |
| | | 35 | | | | | 40 | | | | | 45 | | | |

| Pro | Phe | Val | Ser | Ala | Ser | Thr | Val | Gln | Thr | Gly | Ile | Asn | Ile | Ala | Gly |
| 50 | | | | | 55 | | | | | 60 | | | | | |

| Arg | Ile | Leu | Gly | Val | Leu | Gly | Val | Pro | Phe | Ala | Gly | Gln | Ile | Ala | Ser |
| 65 | | | | 70 | | | | | 75 | | | | | 80 | |

| Phe | Tyr | Ser | Phe | Leu | Val | Gly | Glu | Leu | Trp | Pro | Arg | Gly | Arg | Asp | Pro |
| | | | | 85 | | | | | 90 | | | | | 95 | |

| Trp | Glu | Ile | Phe | Leu | Glu | His | Val | Glu | Gln | Leu | Ile | Arg | Gln | Gln | Val |
| | | | 100 | | | | | 105 | | | | | 110 | | |

| Thr | Glu | Asn | Thr | Arg | Asp | Thr | Ala | Leu | Ala | Arg | Leu | Gln | Gly | Leu | Gly |
| | | | 115 | | | | | 120 | | | | | 125 | | |

| Asn | Ser | Phe | Arg | Ala | Tyr | Gln | Gln | Ser | Leu | Glu | Asp | Trp | Leu | Glu | Asn |
| | 130 | | | | | 135 | | | | | 140 | | | | |

| Arg | Asp | Asp | Ala | Arg | Thr | Arg | Ser | Val | Leu | Tyr | Thr | Gln | Tyr | Ile | Ala |
| 145 | | | | | 150 | | | | | 155 | | | | | 160 |

| Leu | Glu | Leu | Asp | Phe | Leu | Asn | Ala | Met | Pro | Leu | Phe | Ala | Ile | Arg | Asn |
| | | | | 165 | | | | | 170 | | | | | 175 | |

| Gln | Glu | Val | Pro | Leu | Leu | Met | Val | Tyr | Ala | Gln | Ala | Ala | Asn | Leu | His |
| | | | 180 | | | | | 185 | | | | | 190 | | |

| Leu | Leu | Leu | Leu | Arg | Asp | Ala | Ser | Leu | Phe | Gly | Ser | Glu | Phe | Gly | Leu |
| | | | 195 | | | | | 200 | | | | | 205 | | |

| Thr | Ser | Gln | Glu | Ile | Gln | Arg | Tyr | Tyr | Glu | Arg | Gln | Val | Glu | Lys | Thr |
| | 210 | | | | | 215 | | | | | 220 | | | | |

| Arg | Glu | Tyr | Ser | Asp | Tyr | Cys | Ala | Arg | Trp | Tyr | Asn | Thr | Gly | Leu | Asn |
| 225 | | | | | 230 | | | | | 235 | | | | | 240 |

| Asn | Leu | Arg | Gly | Thr | Asn | Ala | Glu | Ser | Trp | Leu | Arg | Tyr | Asn | Gln | Phe |
| | | | | 245 | | | | | 250 | | | | | 255 | |

| Arg | Arg | Asp | Leu | Thr | Leu | Gly | Val | Leu | Asp | Leu | Val | Ala | Leu | Phe | Pro |
| | | | 260 | | | | | 265 | | | | | 270 | | |

Ser Tyr Asp Thr Arg Val Tyr Pro Met Asn Thr Ser Ala Gln Leu Thr
                275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
            595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Gly Thr Thr Thr Tyr Glu Tyr Glu Glu Lys Gln Asn Leu Glu
                645                 650                 655

Lys Ala Gln Lys Ala Leu Asn Ala Leu Phe Thr Asp Gly Thr Asn Gly
            660                 665                 670

Tyr Leu Gln Met Asp Ala Thr Asp Tyr Asp Ile Asn Gln Thr Ala Asn
            675                 680                 685

Leu Ile Glu Cys Val Ser Asp Glu Leu Tyr Ala Lys Glu Lys Ile Val

```
                690             695             700
Leu Leu Asp Glu Val Lys Tyr Ala Lys Arg Leu Ser Ile Ser Arg Asn
705             710             715             720

Leu Leu Leu Asn Asp Asp Leu Glu Phe Ser Asp Gly Phe Gly Glu Asn
            725             730             735

Gly Trp Thr Thr Ser Asp Asn Ile Ser Ile Gln Ala Asp Asn Pro Leu
            740             745             750

Phe Lys Gly Asn Tyr Leu Lys Met Phe Gly Ala Arg Asp Ile Asp Gly
            755             760             765

Thr Leu Phe Pro Thr Tyr Leu Tyr Gln Lys Ile Asp Glu Ser Arg Leu
            770             775             780

Lys Pro Tyr Thr Arg Tyr Arg Val Arg Gly Phe Val Gly Ser Ser Lys
785             790             795             800

Asn Leu Lys Leu Val Val Thr Arg Tyr Glu Lys Glu Ile Asp Ala Ile
            805             810             815

Met Asn Val Pro Asn Asp Leu Ala His Met Gln Leu Asn Pro Ser Cys
            820             825             830

Gly Asp Tyr Arg Cys Glu Ser Ser Gln Phe Leu Val Asn Gln Val
            835             840             845

His Pro Thr Pro Thr Ala Gly Tyr Ala Leu Asp Met Tyr Ala Cys Pro
            850             855             860

Ser Ser Ser Asp Lys Lys His Ile Met Cys His Asp Arg His Pro Phe
865             870             875             880

Asp Phe His Ile Asp Thr Gly Glu Leu Asn Pro Asn Thr Asn Leu Gly
            885             890             895

Ile Asp Val Leu Phe Lys Ile Ser Asn Pro Asn Gly Tyr Ala Thr Leu
            900             905             910

Gly Asn Leu Glu Val Ile Glu Gly Pro Leu Thr Asp Glu Ala Leu
            915             920             925

Val His Val Lys Gln Lys Glu Lys Lys Trp Arg Gln His Met Glu Lys
            930             935             940

Lys Arg Met Glu Thr Gln Gln Ala Tyr Asp Pro Ala Lys Gln Ala Val
945             950             955             960

Asp Ala Leu Phe Thr Asn Glu Gln Glu Leu Asp Tyr His Thr Thr Leu
            965             970             975

Asp His Ile Gln Asn Ala Asp Gln Leu Val Gln Ala Ile Pro Tyr Val
            980             985             990

His His Ala Trp Leu Pro Asp Ala Pro Gly Met Asn Tyr Asp Val Tyr
            995             1000            1005

Gln Gly Leu Asn Ala Arg Ile Met Gln Ala Tyr Asn Leu Tyr Asp
    1010            1015            1020

Ala Arg Asn Val Ile Ile Asn Gly Asp Phe Thr Gln Gly Leu Gln
    1025            1030            1035

Gly Trp His Ala Thr Gly Lys Ala Ala Val Gln Gln Ile Asp Gly
    1040            1045            1050

Ala Ser Val Leu Val Leu Ser Asn Trp Ser Ala Glu Val Ser Gln
    1055            1060            1065

Asn Leu His Ala Gln Asp His His Gly Tyr Met Leu Arg Val Ile
    1070            1075            1080

Ala Lys Lys Glu Gly Pro Gly Lys Gly Tyr Val Met Met Met Asp
    1085            1090            1095

Phe Asn Gly Lys Gln Glu Thr Leu Thr Phe Thr Ser Cys Glu Glu
    1100            1105            1110
```

Gly Tyr Ile Thr Lys Thr Ile Glu Val Phe Pro Glu Ser Asp Arg
1115                1120                1125

Ile Arg Ile Glu Met Gly Glu Thr Glu Gly Thr Phe Tyr Val Asp
1130                1135                1140

Ser Ile Glu Leu Leu Cys Met Gln Gly Tyr Ala Ser Asp Asn Asn
1145                1150                1155

Pro His Thr Gly Asn Met Tyr Glu Gln Ser Tyr Asn Gly Asn Tyr
1160                1165                1170

Asn Gln Asn Thr Ser Asp Val Tyr His Gln Gly Tyr Ile Asn Asn
1175                1180                1185

Tyr Asn Gln Asn Ser Ser Ser Met Tyr Asn Gln Asn Tyr Ile Asn
1190                1195                1200

Asn Asp Asp Leu His Ser Gly Cys Thr Cys Asn Gln Gly His Asn
1205                1210                1215

Ser Gly Cys Thr Cys Asn Gln Gly Tyr Asn Arg
1220                1225

<210> SEQ ID NO 17
<211> LENGTH: 3432
<212> TYPE: DNA
<213> ORGANISM: Artificial
<220> FEATURE:
<223> OTHER INFORMATION: Recombinant nucleotide sequence used for
      expression in a bacterial cell encoding TIC867_22.

<400> SEQUENCE: 17

| | | |
|---|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca aacgggtatt | 180 |
| aacatagctg gtagaatact aggtgtatta ggcgtaccgt tgctggaca aatagctagt | 240 |
| ttttatagtt ttcttgttgg tgaattatgg ccccgcggca gagatccttg gaaattttc | 300 |
| ctagaacatg tcgaacaact tataagacaa caagtaacag aaaatactag ggatacggct | 360 |
| cttgctcgat tacaaggttt aggaaattcc tttagagcct atcaacagtc acttgaagat | 420 |
| tggctagaaa accgtgatga tgcaagaacg agaagtgttc tttataccca atatatagcc | 480 |
| ttagaacttg atttttcttaa tgcgatgccg cttttcgcaa ttagaaacca agaagttcca | 540 |
| ttattaatgg tatatgctca agctgcaaat ttacacctat tattattgag agatgcctct | 600 |
| ctttttggta gtgaatttgg gcttacatcc caagaaattc aacgttatta tgagcgccaa | 660 |
| gtggaaaaaa cgagagaata ttctgattat tgcgcaagat ggtataatac gggtttaaat | 720 |
| aatttgagag ggacaaatgc tgaaagttgg ttgcgatata tcaattccg tagagactta | 780 |
| acgctaggag tattagatct agtggcacta ttcccaagct atgacacgcg tgtttatcca | 840 |
| atgaatacca gtgctcaatt aacaagagaa atttatacag atccaattgg agaacaaat | 900 |
| gcaccttcag gatttgcaag tacgaattgg tttaataata tgcaccatc gtttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |

```
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta cacaaatacc attggtaaag gcgcataccc tccaatcggg taccactgta    1560 gtaaagggc cagggtttac aggaggggat atcctccgtc gaacaagtgg aggaccattt     1620
gcttttagta atgttaatct agattttaac ttgtcacaaa ggtatcgtgc tagaattcgt    1680
tatgcctcta ctactaacct aagaatttac gtaacggttg caggtgaacg aattttgct    1740 ggtcaatttg acaaaactat ggatgctggt gccccattaa cattccaatc ttttagttac    1800
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaaccaatc cgacgcgaga ggcggaagag gatctagaag cagcgaagaa agcggtggcg    1980
agcttgttta cacgtacaag ggacggatta caagtaaatg tgacagatta tcaagtcgat    2040
caagcggcaa atttagtgtc atgcttatca gatgaacaat atgggcatga caaaaagatg    2100
ttattggaag cggtaagagc ggcaaaaacgc ctcagccgag aacgcaactt acttcaggat    2160
ccagatttta atacaatcaa tagtacagaa gaaaatggat ggaaagcaag taacggcgtt    2220
actattagcg agggcggtcc attctataaa ggccgtgcgc ttcagctagc aagcgcaaga    2280
gaaaattacc caacatacat ttatcaaaaa gtaaatgcat cagagttaaa gccgtataca    2340
cgttatagac tggatgggtt cgtgaagagt agtcaagatt tagaaattga tctcattcac    2400
catcataaag tccatctcgt gaaaaatgta ccagataatt tagtatccga tacttactcg    2460
gatggttctt gcagtggaat gaatcgatgt gaggaacaac agatggtaaa tgcgcaactg    2520
gaaacagaac atcatcatcc gatggattgc tgtgaagcgg ctcaaacaca tgagttttct    2580
tcctatatta atacaggcga tctaaattca agtgtagatc aaggcatttg ggttgtattg    2640
aaagttcgaa caaccgatgg ttatgcgacg ctaggaaatc ttgaattggt agaggtcgga    2700
ccgttatcgg gtgaatctct agaacgtgaa caaagggata tgcgaaatg gagtgcagag    2760 ctaggaagaa agcgtgcaga aacagatcgc gtgtatcaag atgccaaaca atccatcaat    2820
catttatttg tggattatca agatcaacaa ttaaatccag aaatagggat ggcagatatt    2880
attgacgctc aaaatcttgt cgcatcaatt tcagatgtgt atagcgatgc agtactgcaa    2940
atccctggaa ttaactatga gatttacaca gagctatcca atcgcttaca acaagcatcg    3000
tatctgtata cgtctcgaaa tgcggtgcaa aatgggact ttaacagcgg tctagatagt     3060
tggaatgcaa cagggggggc tacggtacaa caggatggca atacgcatt cttagttctt     3120 tctcattggg atgcacaagt ttctcaacaa tttagagtgc agccgaattg taaatatgta    3180
ttacgtgtaa cagcagagaa agtaggcggc ggagacggat acgtgacaat ccgggatggt    3240
gctcatcata cagaaaagct tacatttaat gcatgtgatt atgatataaa tggcacgtac    3300
gtgactgata atacgtatct aacaaaagaa gtggtattct attcacatac agaacacatg    3360
tgggtagagg taagtgaaac agaaggtgca tttcatatag atagtattga attcgttgaa    3420
acagaaaagt ag                                                       3432
```

<210> SEQ ID NO 18
<211> LENGTH: 3432
<212> TYPE: DNA
<213> ORGANISM: Artificial
<220> FEATURE:

<223> OTHER INFORMATION: Synthetic nucleotide sequence designed for
      expression in a plant cell encoding TIC867_22.

<400> SEQUENCE: 18

| | | | | | | |
|---|---|---|---|---|---|---|
| atgaccagca | accgaaagaa | cgagaacgag | atcatcaacg | ccctgtccat | accggccgtg | 60 |
| tcaaaccact | ccgcccagat | gaacctctcc | accgacgcga | ggatcgagga | ctccctctgc | 120 |
| atcgccgagg | gcaacaacat | cgacccgttc | gtgtctgcaa | gcacggtcca | gaccggcatc | 180 |
| aacatcgcgg | gccgcatcct | gggcgtgctc | ggcgtgccct | cgcgggtca | aatgcctct | 240 |
| ttctactcat | tcctcgtggg | cgagctgtgg | ccgcgcggac | gtgacccgtg | ggaaatcttc | 300 |
| ctggagcacg | ttgagcagct | catccggcag | caagtgaccg | agaacaccag | ggacaccgca | 360 |
| ctggcacggc | tccagggcct | tggcaacagc | ttccgcgcct | accagcagtc | gctggaggac | 420 |
| tggctggaga | accgagacga | cgccagaacc | cgctcagttc | tgtacacaca | gtacatcgcc | 480 |
| ctagagctgg | acttcctcaa | cgctatgccg | ctcttcgcca | tccgtaacca | ggaagtaccg | 540 |
| cttctgatgg | tgtacgcaca | agcagcgaac | ctccatctgc | tcctgctgcg | agacgcatct | 600 |
| ctgttcggca | gtgagttcgg | gctgacgagc | caggagatcc | agcgctacta | cgagcgccaa | 660 |
| gtggagaaga | ctcgtgagta | cagcgactac | tgcgcgcgct | ggtacaacac | gggcttgaac | 720 |
| aaccttcgcg | ggacaaacgc | cgaatcctgg | cttcgctaca | accagttccg | ccgcgacctc | 780 |
| acgctgggtg | tgctggacct | ggtcgcgctc | ttcccgtcct | acgacacacg | ggtgtaccca | 840 |
| atgaacacga | gcgcacagct | cacccgtgag | atctacacag | atcccatcgg | ccgcaccaac | 900 |
| gctcccagtg | gcttcgcaag | cacgaattgg | ttcaacaata | acgctccttc | tttctctgcc | 960 |
| atcgaggccg | ctgtcatcag | accgccgcac | ttactcgatt | tcccggagca | gctcactatc | 1020 |
| ttctctgtgt | tgtcccggtg | gtcgaacacg | cagtacatga | actactgggt | gggccacagg | 1080 |
| ctagagagcc | ggaccatccg | tggcagtctc | tcaacctcga | cccacggcaa | cacgaacacg | 1140 |
| agcatcaacc | ctgtcactct | ccagtttaca | tctagggacg | tttacaggac | agagtcgttc | 1200 |
| gctggcatta | acattctgtt | gaccactccg | gtgaacggcg | tcccttgggc | ccgcttcaac | 1260 |
| tggaggaatc | ctctgaactc | actgcgcggc | agccttctct | acactatcgg | ctacaccggc | 1320 |
| gttgggacgc | aactcttcga | ctcggagacc | gagctgccgc | ccgagaccac | cgagcggcct | 1380 |
| aactacgaga | gttattcaca | caggctctcc | aacatccgct | tgatttctgg | gaacaccttg | 1440 |
| cgggctccgg | tgtactcctg | gacgcaccgc | agcgccgaca | gaactaatac | catcagctcc | 1500 |
| gactcgatca | cccagatccc | gctggtgaag | gctcacacgc | ttcagtcggg | caccacagtc | 1560 |
| gtcaagggcc | ctggcttcac | cggcggcgac | atcctgcgtc | gcacatctgg | cggacccttc | 1620 |
| gccttcagca | acgtgaactt | ggacttcaat | ttgtcacagc | ggtatcgtgc | cagaatccgg | 1680 |
| tacgccagca | ctacgaacct | gcgaatctat | gttactgtgg | cgggcgagcg | gatcttcgcc | 1740 |
| gggcaattcg | acaagacgat | ggacgcggga | gcacctctga | cattccagtc | attctcttac | 1800 |
| gccacgatca | cacggcatt | cacgtttccg | gagcgttcca | gtagcctgac | cgtgggcgct | 1860 |
| gataccttca | gtagcgggaa | cgaggtgtac | gttgaccgtt | tcgagctgat | cccggtcacc | 1920 |
| gccaccaacc | cgacgcggga | agctgaggaa | gacttggaag | ccgccaagaa | agcggtcgcc | 1980 |
| agcctgttta | ctcggacgcg | ggacgggctc | caagtgaatg | tgacggacta | tcaagtggat | 2040 |
| caggccgcta | acctcgtgtc | atgcctgagc | gacgagcagt | acggtcacga | caagaaaatg | 2100 |
| ctgctggagg | ccgtccgggc | cgccaagcgg | ctgtccaggg | agcgtaacct | gctacaagat | 2160 |
| cccgacttta | acacgatcaa | cagcacagag | gagaatggct | ggaaggccag | caacggagtt | 2220 |

```
acgataagcg agggcggtcc gttctacaag ggtcgtgccc tccagctcgc ctctgcaagg    2280
gagaactatc caacctacat ctatcagaag gtgaacgcat ccgagcttaa gccctacaca    2340
cgctaccgcc tggacgggtt cgttaagtcc agtcaagacc tagagataga cctcatccac    2400
caccacaaag tgcatctggt caagaacgtt cccgataatc tcgtgagcga tacctactca    2460
gacggctcat gctctggcat gaacagatgt gaggagcaac agatggttaa tgctcaactc    2520
gaaaccgagc atcatcatcc tatggattgc tgcgaggccg cgcagaccca tgagttcagc    2580
tcttacatca acaccggaga cctcaacagt agcgtggatc agggaatttg ggtggtgctt    2640
aaagtgcgta caaccgacgg ctacgccacc ctcggcaacc ttgagcttgt cgaggtcgga    2700
ccacttagcg gcgagtccct ggaacgtgag cagcgggaca acgccaaatg gagcgcagag    2760
ctagggcgca aacgcgcgga gacggaccgg gtttatcagg acgcgaagca gtccatcaat    2820
cacctcttcg tggattatca ggaccagcag cttaatccag agatcggcat ggccgacatc    2880
atcgacgccc agaacctagt agcgtcgatt tccgatgtct attccgacgc cgtgcttcaa    2940
atacctggca tcaactacga gatctacaca gagttgtcca acaggctcca gcaagcgtca    3000
tacctctaca ccagccgcaa cgccgtccag aatggcgact tcaattccgg actagactcc    3060
tggaacgcca cgggcggagc tacggtgcaa caagacggca cacccacttt cctcgtactt    3120
agccactggg acgctcaagt gagtcagcaa ttccgggttc agccgaactg caagtacgtc    3180
ctgcgcgtaa cggccgagaa ggttggaggc ggagacggca cgttaccat ccgcgacggc     3240 gctcaccaca ccgagaaact gacgttcaac gcttgtgact cgacatcaa cggcacttac     3300 gtgacggaca cacctaccct gacgaaggag gtggtgttct attctcacac cgagcacatg    3360
tgggttgagg tcagcgagac cgagggagcc ttccacattg acagcatcga gttcgtggag    3420
actgagaagt ga                                                        3432
```

<210> SEQ ID NO 19
<211> LENGTH: 1143
<212> TYPE: PRT
<213> ORGANISM: Artificial
<220> FEATURE:
<223> OTHER INFORMATION: Amino acid sequence of the chimeric protein variant TIC867_22.

<400> SEQUENCE: 19

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140
```

```
Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
                195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
                500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
            530                 535                 540

Val Asn Leu Asp Phe Asn Leu Ser Gln Arg Tyr Arg Ala Arg Ile Arg
545                 550                 555                 560
```

```
Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
            595                 600                 605

Phe Pro Glu Arg Ser Ser Ser Leu Thr Val Gly Ala Asp Thr Phe Ser
        610                 615                 620

Ser Gly Asn Glu Val Tyr Val Asp Arg Phe Glu Leu Ile Pro Val Thr
625                 630                 635                 640

Ala Thr Asn Pro Thr Arg Glu Ala Glu Asp Leu Glu Ala Ala Lys
                645                 650                 655

Lys Ala Val Ala Ser Leu Phe Thr Arg Thr Arg Asp Gly Leu Gln Val
            660                 665                 670

Asn Val Thr Asp Tyr Gln Val Asp Gln Ala Ala Asn Leu Val Ser Cys
            675                 680                 685

Leu Ser Asp Glu Gln Tyr Gly His Asp Lys Lys Met Leu Leu Glu Ala
        690                 695                 700

Val Arg Ala Ala Lys Arg Leu Ser Arg Glu Arg Asn Leu Leu Gln Asp
705                 710                 715                 720

Pro Asp Phe Asn Thr Ile Asn Ser Thr Glu Glu Asn Gly Trp Lys Ala
                725                 730                 735

Ser Asn Gly Val Thr Ile Ser Glu Gly Pro Phe Tyr Lys Gly Arg
            740                 745                 750

Ala Leu Gln Leu Ala Ser Ala Arg Glu Asn Tyr Pro Thr Tyr Ile Tyr
            755                 760                 765

Gln Lys Val Asn Ala Ser Glu Leu Lys Pro Tyr Thr Arg Tyr Arg Leu
770                 775                 780

Asp Gly Phe Val Lys Ser Gln Asp Leu Glu Ile Asp Leu Ile His
785                 790                 795                 800

His His Lys Val His Leu Val Lys Asn Val Pro Asp Asn Leu Val Ser
                805                 810                 815

Asp Thr Tyr Ser Asp Gly Ser Cys Ser Gly Met Asn Arg Cys Glu Glu
            820                 825                 830

Gln Gln Met Val Asn Ala Gln Leu Glu Thr Glu His His His Pro Met
            835                 840                 845

Asp Cys Cys Glu Ala Ala Gln Thr His Glu Phe Ser Ser Tyr Ile Asn
        850                 855                 860

Thr Gly Asp Leu Asn Ser Ser Val Asp Gln Gly Ile Trp Val Val Leu
865                 870                 875                 880

Lys Val Arg Thr Thr Asp Gly Tyr Ala Thr Leu Gly Asn Leu Glu Leu
                885                 890                 895

Val Glu Val Gly Pro Leu Ser Gly Glu Ser Leu Glu Arg Glu Gln Arg
            900                 905                 910

Asp Asn Ala Lys Trp Ser Ala Glu Leu Gly Arg Lys Ala Glu Thr
            915                 920                 925

Asp Arg Val Tyr Gln Asp Ala Lys Gln Ser Ile Asn His Leu Phe Val
        930                 935                 940

Asp Tyr Gln Asp Gln Leu Asn Pro Glu Ile Gly Met Ala Asp Ile
945                 950                 955                 960

Ile Asp Ala Gln Asn Leu Val Ala Ser Ile Ser Asp Val Tyr Ser Asp
                965                 970                 975

Ala Val Leu Gln Ile Pro Gly Ile Asn Tyr Glu Ile Tyr Thr Glu Leu
```

|   |   |   |   | 980 |   |   | 985 |   |   | 990 |   |   |
|---|---|---|---|---|---|---|---|---|---|---|---|---|
| Ser | Asn | Arg | Leu | Gln | Gln | Ala | Ser | Tyr | Leu | Tyr | Thr | Ser | Arg | Asn | Ala |
|   |   |   | 995 |   |   |   | 1000 |   |   |   | 1005 |   |

| Val | Gln | Asn | Gly | Asp | Phe | Asn | Ser | Gly | Leu | Asp | Ser | Trp | Asn | Ala |
|   | 1010 |   |   |   |   | 1015 |   |   |   |   | 1020 |

| Thr | Gly | Gly | Ala | Thr | Val | Gln | Gln | Asp | Gly | Asn | Thr | His | Phe | Leu |
|   | 1025 |   |   |   |   | 1030 |   |   |   |   | 1035 |

| Val | Leu | Ser | His | Trp | Asp | Ala | Gln | Val | Ser | Gln | Gln | Phe | Arg | Val |
|   | 1040 |   |   |   |   | 1045 |   |   |   |   | 1050 |

| Gln | Pro | Asn | Cys | Lys | Tyr | Val | Leu | Arg | Val | Thr | Ala | Glu | Lys | Val |
|   | 1055 |   |   |   |   | 1060 |   |   |   |   | 1065 |

| Gly | Gly | Gly | Asp | Gly | Tyr | Val | Thr | Ile | Arg | Asp | Gly | Ala | His | His |
|   | 1070 |   |   |   |   | 1075 |   |   |   |   | 1080 |

| Thr | Glu | Lys | Leu | Thr | Phe | Asn | Ala | Cys | Asp | Tyr | Asp | Ile | Asn | Gly |
|   | 1085 |   |   |   |   | 1090 |   |   |   |   | 1095 |

| Thr | Tyr | Val | Thr | Asp | Asn | Thr | Tyr | Leu | Thr | Lys | Glu | Val | Val | Phe |
|   | 1100 |   |   |   |   | 1105 |   |   |   |   | 1110 |

| Tyr | Ser | His | Thr | Glu | His | Met | Trp | Val | Glu | Val | Ser | Glu | Thr | Glu |
|   | 1115 |   |   |   |   | 1120 |   |   |   |   | 1125 |

| Gly | Ala | Phe | His | Ile | Asp | Ser | Ile | Glu | Phe | Val | Glu | Thr | Glu | Lys |
|   | 1130 |   |   |   |   | 1135 |   |   |   |   | 1140 |

<210> SEQ ID NO 20
<211> LENGTH: 3696
<212> TYPE: DNA
<213> ORGANISM: Artificial
<220> FEATURE:
<223> OTHER INFORMATION: Synthetic nucleotide sequence designed for
      expression in a plant cell encoding TIC867_23.

<400> SEQUENCE: 20

```
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg caacaacat cgacccgttc gtgtctgcaa gcacggtcca gaccggcatc     180
aacatcgcgg gccgcatcct gggcgtgctc ggcgtgccct cgcgggtca atcgcctct      240
ttctactcat tcctcgtggg cgagctgtgg ccgcgcggac gtgacccgtg gaaatcttc     300
ctggagcacg ttgagcagct catccggcag caagtgaccg agaacaccag ggacaccgca     360
ctggcacggc tccagggcct tggcaacagc ttccgcgcct accagcagtc gctggaggac     420
tggctggaga accgagacga cgccagaacc cgctcagttc tgtacacaca gtacatcgcc     480
ctagagctgg acttcctcaa cgctatgccg ctcttcgcca tccgtaacca ggaagtaccg     540
cttctgatgg tgtacgcaca agcagcgaac ctccatctgc tcctgctgcg agacgcatct     600
ctgttcggca gtgagttcgg gctgacgagc caggagatcc agcgctacta cgagcgccaa     660
gtggagaaga ctcgtgagta cagcgactac tgcgcgcgct ggtacaacac gggcttgaac     720
aaccttcgcg gacaaacgc cgaatcctgg cttcgctaca ccagttccg ccgcgacctc      780
acgctgggtg tgctggacct ggtcgcgctc ttccgtcct acgacacacg ggtgtaccca     840
atgaacacga gcgcacagct cacccgtgag atctacacag atcccatcgg ccgcaccaac     900
gctcccagtg gcttcgcaag cacgaattgg ttcaacaata acgctccttc tttctctgcc     960
atcgaggccg ctgtcatcag accgccgcac ttactcgatt cccgagga gctcactatc     1020
ttctctgtgt tgtcccggtg gtcgaacacg cagtacatga actactgggt gggccacagg    1080
```

```
ctagagagcc ggaccatccg tggcagtctc tcaacctcga cccacggcaa cacgaacacg    1140
agcatcaacc ctgtcactct ccagtttaca tctagggacg tttacaggac agagtcgttc    1200
gctggcatta acattctgtt gaccactccg gtgaacggcg tcccttgggc ccgcttcaac    1260
tggaggaatc ctctgaactc actgcgcggc agccttctct acactatcgg ctacaccggc    1320
gttgggacgc aactcttcga ctcggagacc gagctgccgc ccgagaccac cgagcggcct    1380
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggacccttc    1620
gccttcagca acgtgaactt ggacttcaat ttgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccacgg cgaccttcga ggcggagtat gacttggagc gggctcagga ggccgtcaac    1980
gcgctgttca caaacaccaa tcctcgccgc ctcaagacgg gtgtgactga ttaccacatt    2040
gacgaggtct ccaacttggt cgcgtgtctg tccgatgagt tctgcctgga cgagaagcgg    2100
gaactgctgg agaaggtcaa gtacgccaag cgcctctccg acgaaaggaa cctcctccaa    2160
gatcccaact ttacttccat taacaagcag ccggacttca tctccaccaa cgagcagtcc    2220
aacttcacct caatccacga gcagtcggag cacgggtggt ggggcagcga aacatcacc    2280 atccaagagg gcaacgacgt cttcaaggag aactacgtga tcctgcccgg caccttcaac    2340
gagtgttacc cgacctatct ctaccagaag attggcgaag cggaactcaa ggcttacacc    2400
cgttaccaac tgagtggcta cattgaggac tcacaagacc tggaaatcta cctgatccgc    2460
tacaacgcca agcacgagac cctcgacgtg cctggcacgg agtccgtctg gcccttgagc    2520
gtggagtctc ctatcggtcg ttgcggcgag cccaatcgct gcgctccgca ctttgagtgg    2580
aatcctgatt tggattgctc ctgccgagac ggtgagaaat gcgcccacca ctcgcaccac    2640
ttcagcctag acatcgacgt gggctgcatc gacctgcacg agaacttggg cgtctgggtc    2700
gtgttcaaga tcaagacaca ggagggccat gctcggcttg ggaacctgga gttcatcgag    2760
gagaagccac tgctgggtga agccttgtca cgggtgaaac gcgccgagaa gaagtggcgg    2820
gacaaacggg agaagctcca gttggagaca aagcgtgtgt acacagaggc caaggaggcc    2880
gtggatgcct tgttcgtgga cagtcagtac gacaggctgc aagcggacac caacatcggg    2940
atgatccacg cggctgataa gcttgttcac agaatccgcg aggcgtacct gtcagagctt    3000
agcgtgatcc caggcgtcaa cgccgaaatc ttcgaggaac tggagggccg cattatcacg    3060
gcaatctcac tttatgacgc gaggaatgtg gtcaagaacg gtgacttcaa caacggcttg    3120
gcgtgttgga acgttaaagg gcacgtggat gtacaacagt cacaccacag aagtgtcttg    3180
gtcatcccgg agtgggaggc ggaagtgagc caggccgtcc gggtctgccc tgggcgcggt    3240
tacatcctcc gcgtgacagc gtacaaggag ggctacggtg agggctgcgt gacgatccac    3300
gagattgaga caacacgga cgagcttaag ttcaagaact gcgaggagga ggaagtgtac    3360
ccgacagaca ccggcacctg caacgactac accgcccacc aagggaccgc cgcctgcaac    3420
agccgcaacg cgggctatga agatgcgtac gaggttgata ccaccgcctc agtgaactac    3480
```

```
aaaccgactt atgaggagga gacatacacg gacgtcaggc gcgacaacca ttgtgagtac    3540
gaccgtggct acgtgaacta tccgccggtg ccagcgggct acatgacgaa ggagctagaa    3600
tacttccctg agacggacaa ggtgtggatt gaaatcggcg agaccgaggg caagtttatc    3660
gtggattctg tcgagctgct gctaatggag gagtag                              3696
```

<210> SEQ ID NO 21
<211> LENGTH: 1231
<212> TYPE: PRT
<213> ORGANISM: Artificial
<220> FEATURE:
<223> OTHER INFORMATION: Amino acid sequence of the chimeric protein variant TIC867_23.

<400> SEQUENCE: 21

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

```
Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
            370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
                500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
            530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
                580                 585                 590

Leu Thr Phe Gln Ser Phe Ser Tyr Ala Thr Ile Asn Thr Ala Phe Thr
            595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Tyr Asp Leu Glu Arg Ala Gln
                645                 650                 655

Glu Ala Val Asn Ala Leu Phe Thr Asn Thr Asn Pro Arg Arg Leu Lys
                660                 665                 670

Thr Gly Val Thr Asp Tyr His Ile Asp Glu Val Ser Asn Leu Val Ala
            675                 680                 685

Cys Leu Ser Asp Glu Phe Cys Leu Asp Glu Lys Arg Glu Leu Leu Glu
            690                 695                 700

Lys Val Lys Tyr Ala Lys Arg Leu Ser Asp Glu Arg Asn Leu Leu Gln
705                 710                 715                 720

Asp Pro Asn Phe Thr Ser Ile Asn Lys Gln Pro Asp Phe Ile Ser Thr
                725                 730                 735
```

```
Asn Glu Gln Ser Asn Phe Thr Ser Ile His Glu Gln Ser Glu His Gly
            740                 745                 750

Trp Trp Gly Ser Glu Asn Ile Thr Ile Gln Glu Gly Asn Asp Val Phe
        755                 760                 765

Lys Glu Asn Tyr Val Ile Leu Pro Gly Thr Phe Asn Glu Cys Tyr Pro
    770                 775                 780

Thr Tyr Leu Tyr Gln Lys Ile Gly Glu Ala Glu Leu Lys Ala Tyr Thr
785                 790                 795                 800

Arg Tyr Gln Leu Ser Gly Tyr Ile Glu Asp Ser Gln Asp Leu Glu Ile
                805                 810                 815

Tyr Leu Ile Arg Tyr Asn Ala Lys His Glu Thr Leu Asp Val Pro Gly
            820                 825                 830

Thr Glu Ser Val Trp Pro Leu Ser Val Glu Ser Pro Ile Gly Arg Cys
            835                 840                 845

Gly Glu Pro Asn Arg Cys Ala Pro His Phe Glu Trp Asn Pro Asp Leu
        850                 855                 860

Asp Cys Ser Cys Arg Asp Gly Glu Lys Cys Ala His His Ser His His
865                 870                 875                 880

Phe Ser Leu Asp Ile Asp Val Gly Cys Ile Asp Leu His Glu Asn Leu
                885                 890                 895

Gly Val Trp Val Val Phe Lys Ile Lys Thr Gln Glu Gly His Ala Arg
            900                 905                 910

Leu Gly Asn Leu Glu Phe Ile Glu Lys Pro Leu Leu Gly Glu Ala
            915                 920                 925

Leu Ser Arg Val Lys Arg Ala Glu Lys Lys Trp Arg Asp Lys Arg Glu
    930                 935                 940

Lys Leu Gln Leu Glu Thr Lys Arg Val Tyr Thr Glu Ala Lys Glu Ala
945                 950                 955                 960

Val Asp Ala Leu Phe Val Asp Ser Gln Tyr Asp Arg Leu Gln Ala Asp
                965                 970                 975

Thr Asn Ile Gly Met Ile His Ala Ala Asp Lys Leu Val His Arg Ile
            980                 985                 990

Arg Glu Ala Tyr Leu Ser Glu Leu  Ser Val Ile Pro Gly  Val Asn Ala
        995                 1000                1005

Glu Ile  Phe Glu Glu Leu Glu  Gly Arg Ile Ile Thr  Ala Ile Ser
    1010                1015                1020

Leu Tyr Asp Ala Arg Asn Val  Val Lys Asn Gly Asp  Phe Asn Asn
    1025                1030                1035

Gly Leu Ala Cys Trp Asn Val  Lys Gly His Val Asp  Val Gln Gln
    1040                1045                1050

Ser His  His Arg Ser Val Leu  Val Ile Pro Glu Trp  Glu Ala Glu
    1055                1060                1065

Val Ser  Gln Ala Val Arg Val  Cys Pro Gly Arg Gly  Tyr Ile Leu
    1070                1075                1080

Arg Val  Thr Ala Tyr Lys Glu  Gly Tyr Gly Glu Gly  Cys Val Thr
    1085                1090                1095

Ile His  Glu Ile Glu Asn Asn  Thr Asp Glu Leu Lys  Phe Lys Asn
    1100                1105                1110

Cys Glu  Glu Glu Glu Val Tyr  Pro Thr Asp Thr Gly  Thr Cys Asn
    1115                1120                1125

Asp Tyr  Thr Ala His Gln Gly  Thr Ala Ala Cys Asn  Ser Arg Asn
    1130                1135                1140

Ala Gly  Tyr Glu Asp Ala Tyr  Glu Val Asp Thr Thr  Ala Ser Val
```

```
                1145                1150                1155
Asn Tyr Lys Pro Thr Tyr Glu Glu Glu Thr Tyr Thr Asp Val Arg
            1160                1165                1170

Arg Asp Asn His Cys Glu Tyr Asp Arg Gly Tyr Val Asn Tyr Pro
            1175                1180                1185

Pro Val Pro Ala Gly Tyr Met Thr Lys Glu Leu Glu Tyr Phe Pro
            1190                1195                1200

Glu Thr Asp Lys Val Trp Ile Glu Ile Gly Glu Thr Glu Gly Lys
            1205                1210                1215

Phe Ile Val Asp Ser Val Glu Leu Leu Leu Met Glu Glu
            1220                1225                1230

<210> SEQ ID NO 22
<211> LENGTH: 3666
<212> TYPE: DNA
<213> ORGANISM: Artificial
<220> FEATURE:
<223> OTHER INFORMATION: Synthetic nucleotide sequence designed for
      expression in a plant cell encoding TIC867_24.

<400> SEQUENCE: 22
atgaccagca accgaaagaa cgagaacgag atcatcaacg ccctgtccat accggccgtg      60
tcaaaccact ccgcccagat gaacctctcc accgacgcga ggatcgagga ctccctctgc    120
atcgccgagg caacaacat cgacccgttc gtgtctgcaa gcacggtcca gaccggcatc     180
aacatcgcgg ccgcatcct gggcgtgctc ggcgtgccct cgcgggtca aatcgcctct     240 ttctactcat tcctcgtggg cgagctgtgg ccgcgcggac gtgacccgtg gaaatcttc    300 ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg gacaaacgc cgaatcctgg cttcgctaca accagttccg ccgcgacctc     780
acgctgggtg tgctggacct ggtcgcgctc ttcccgtcct acgacacacg ggtgtaccca    840
atgaacacga cgcacagct cacccgtgag atctacacag atcccatcgg ccgcaccaac    900
gctcccagtg gcttcgcaag cacgaattgg ttcaacaata cgctccttc tttctctgcc    960 atcgaggccg ctgtcatcag accgccgcac ttactcgatt cccggagca gctcactatc   1020 ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctaggacg tttacaggac agagtcgttc     1200
gctggcatta acattctgtt gaccactccg gtgaacggcg tccctggc ccgcttcaac    1260 tggaggaatc ctctgaactc actgcgcggc agccttctct acactatcgg ctacaccggc   1320
gttgggacgc aactcttcga ctcggagacc gagctgccgc cgagaccac cgagcggcct   1380 aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
```

```
gtcaagggcc ctggcttcac cggcggcgac atcctgcgtc gcacatctgg cggacccttc    1620
gccttcagca acgtgaactt ggacttcaat ttgtcacagc ggtatcgtgc cagaatccgg    1680
tacgccagca ctacgaacct gcgaatctat gttactgtgg cgggcgagcg atcttcgcc    1740 gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccaccg cgacgtttga agctgaatcc gacctcgagc gtgcgcgcaa ggcggtgaac    1980
gctctgttca cgagcaccaa ccctcgtggc ttgaagacgg atgtgacgga ctaccacatc    2040
gaccaagtct cgaacctcgt ggagtgcctg agcgacgagt tctgtcttga caagaagcgc    2100
gagctgctgg aggaggtgaa gtacgccaag cgcctctccg atgagcgcaa cctgctccaa    2160
gatcctacct tcacgtcgat ttccggccaa accgaccgtg gatggatcgg ctcgactggc    2220
atctccatcc agggcggcga cgacatcttc aaggagaact atgttcggct gccgggcacg    2280
gtggacgagt gttacccgac gtacctctac cagaagatag acgagagtca actcaagtcc    2340
tacacgcggt atcagttacg tggctacatt gaagactccc aggacttgga aatctatctc    2400
atacggtaca acgccaagca cgagaccttc agcgtgccgg aacggagtc gccctggcca    2460 agctctggcg tgtaccccttc cggtaggtgc ggcgagccca accgctgtgc acctcgaatc    2520
gaatggaacc cggaccttga ctgctcttgc cggtacggcg agaagtgcgt ccatcattct    2580
caccacttca gcttggacat tgacgtcggc tgcaccgacc tcaatgaaga cctcggagtg    2640
tgggtcatct tcaagatcaa gacacaggac gggcacgcga aactaggaaa cctggagttc    2700
atcgaggaga agccactcct cggcaaggca ctttccaggg tcaagcgggc cgagaagaaa    2760
tggagggaca agtacgagaa actccagctc gaaacaaagc gggtgtacac ggaggcaaag    2820
gaatccgtgg acgccctgtt cgtggactct cagtacgaca agctccagca gaacacaaac    2880
attggcatca tccacggtgc ggacaagcaa gtgcacagga tacgggagcc ttacctctcg    2940
gagctgccgg tgattccctc gatcaacgcg gcgatcttcg aggaactgga gggccacatc    3000
ttcaaggcgt attctctgta cgacgcgcgt aacgtcatca agaacggcga cttcaacaat    3060
gggctgtcct gctggaacgt taaaggccac gtcgatgtcc agcagaacca ccataggtca    3120
gtcctggtgc tgagcgagtg ggaggcggag gtgtcccaga aggtgcgcgt gtgcccggat    3180
cgcggctaca tcttgagggt gacagcctac aaggagggct acggcgaggg ctgtgtcacg    3240
atccatgagt tcgaggacaa cacgatgtc ctgaaattcc gtaacttcgt cgaggaggag    3300
gtctatccca caacaccgt gacctgcaac gactacacga ccaatcagtc ggctgagggc    3360
agtaccgatg cctgcaacag ctacaaccgt ggttacgaag atggatacga gaaccgctac    3420
gagcccaatc cttcggctcc cgtgaattac actcccacgt acgaggaggg catgtacact    3480
gacactcagg gctacaacca ttgcgtcagc gaccgtggct accgcaacca cacgccgctc    3540
ccagcgggct acgtgacgct ggagctggaa tactttcccg agacagaaca agtgtggata    3600
gagatcggcg agaccgaggg cacattcatc gtgggctctg tggaattgct cctcatggag    3660
gagtaa                                                              3666
```

<210> SEQ ID NO 23  
<211> LENGTH: 1221  
<212> TYPE: PRT  
<213> ORGANISM: Artificial  
<220> FEATURE:

<223> OTHER INFORMATION: Amino acid sequence of the chimeric protein variant TIC867_24.

<400> SEQUENCE: 23

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400
```

-continued

```
Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Pro Phe Ala Phe Ser Asn
            530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
            565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
            595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Ser Asp Leu Glu Arg Ala Arg
            645                 650                 655

Lys Ala Val Asn Ala Leu Phe Thr Ser Thr Asn Pro Arg Gly Leu Lys
            660                 665                 670

Thr Asp Val Thr Asp Tyr His Ile Asp Gln Val Ser Asn Leu Val Glu
            675                 680                 685

Cys Leu Ser Asp Glu Phe Cys Leu Asp Lys Lys Arg Glu Leu Leu Glu
            690                 695                 700

Glu Val Lys Tyr Ala Lys Arg Leu Ser Asp Glu Arg Asn Leu Leu Gln
705                 710                 715                 720

Asp Pro Thr Phe Thr Ser Ile Ser Gly Gln Thr Asp Arg Gly Trp Ile
            725                 730                 735

Gly Ser Thr Gly Ile Ser Ile Gln Gly Gly Asp Asp Ile Phe Lys Glu
            740                 745                 750

Asn Tyr Val Arg Leu Pro Gly Thr Val Asp Glu Cys Tyr Pro Thr Tyr
            755                 760                 765

Leu Tyr Gln Lys Ile Asp Glu Ser Gln Leu Lys Ser Tyr Thr Arg Tyr
            770                 775                 780

Gln Leu Arg Gly Tyr Ile Glu Asp Ser Gln Asp Leu Glu Ile Tyr Leu
785                 790                 795                 800

Ile Arg Tyr Asn Ala Lys His Glu Thr Leu Ser Val Pro Gly Thr Glu
            805                 810                 815
```

-continued

Ser Pro Trp Pro Ser Ser Gly Val Tyr Pro Ser Gly Arg Cys Gly Glu
             820                 825                 830

Pro Asn Arg Cys Ala Pro Arg Ile Glu Trp Asn Pro Asp Leu Asp Cys
         835                 840                 845

Ser Cys Arg Tyr Gly Glu Lys Cys Val His His Ser His His Phe Ser
     850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Lys Leu Gly
             885                 890                 895

Asn Leu Glu Phe Ile Glu Glu Lys Pro Leu Leu Gly Lys Ala Leu Ser
         900                 905                 910

Arg Val Lys Arg Ala Glu Lys Lys Trp Arg Asp Lys Tyr Glu Lys Leu
     915                 920                 925

Gln Leu Glu Thr Lys Arg Val Tyr Thr Glu Ala Lys Glu Ser Val Asp
 930                 935                 940

Ala Leu Phe Val Asp Ser Gln Tyr Asp Lys Leu Gln Ala Asn Thr Asn
945                 950                 955                 960

Ile Gly Ile Ile His Gly Ala Asp Lys Gln Val His Arg Ile Arg Glu
             965                 970                 975

Pro Tyr Leu Ser Glu Leu Pro Val Ile Pro Ser Ile Asn Ala Ala Ile
         980                 985                 990

Phe Glu Glu Leu Glu Gly His Ile Phe Lys Ala Tyr Ser Leu Tyr Asp
     995                 1000                 1005

Ala Arg Asn Val Ile Lys Asn Gly Asp Phe Asn Asn Gly Leu Ser
    1010                 1015                 1020

Cys Trp Asn Val Lys Gly His Val Asp Val Gln Gln Asn His His
    1025                 1030                 1035

Arg Ser Val Leu Val Leu Ser Glu Trp Glu Ala Glu Val Ser Gln
    1040                 1045                 1050

Lys Val Arg Val Cys Pro Asp Arg Gly Tyr Ile Leu Arg Val Thr
    1055                 1060                 1065

Ala Tyr Lys Glu Gly Tyr Gly Glu Gly Cys Val Thr Ile His Glu
    1070                 1075                 1080

Phe Glu Asp Asn Thr Asp Val Leu Lys Phe Arg Asn Phe Val Glu
    1085                 1090                 1095

Glu Glu Val Tyr Pro Asn Asn Thr Val Thr Cys Asn Asp Tyr Thr
    1100                 1105                 1110

Thr Asn Gln Ser Ala Glu Gly Ser Thr Asp Ala Cys Asn Ser Tyr
    1115                 1120                 1125

Asn Arg Gly Tyr Glu Asp Gly Tyr Glu Asn Arg Tyr Glu Pro Asn
    1130                 1135                 1140

Pro Ser Ala Pro Val Asn Tyr Thr Pro Thr Tyr Glu Glu Gly Met
    1145                 1150                 1155

Tyr Thr Asp Thr Gln Gly Tyr Asn His Cys Val Ser Asp Arg Gly
    1160                 1165                 1170

Tyr Arg Asn His Thr Pro Leu Pro Ala Gly Tyr Val Thr Leu Glu
    1175                 1180                 1185

Leu Glu Tyr Phe Pro Glu Thr Glu Gln Val Trp Ile Glu Ile Gly
    1190                 1195                 1200

Glu Thr Glu Gly Thr Phe Ile Val Gly Ser Val Glu Leu Leu Leu
    1205                 1210                 1215

Met Glu Glu

<210> SEQ ID NO 24
<211> LENGTH: 3651
<212> TYPE: DNA
<213> ORGANISM: Artificial
<220> FEATURE:
<223> OTHER INFORMATION: Synthetic nucleotide sequence designed for expression in a plant cell encoding TIC867_25.

<400> SEQUENCE: 24

```
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg gcaacaacat cgacccgttc gtgtctgcaa gcacggtcca gaccggcatc     180
aacatcgcgg gccgcatcct gggcgtgctc ggcgtgccct cgcgggtca aatcgcctct      240
ttctactcat cctcgtgggc gagctgtgg ccgcgcggac gtgacccgtg ggaaatcttc      300
ctggagcacg ttgagcagct catccggcag caagtgaccg agaacaccag ggacaccgca     360
ctggcacggc tccagggcct tggcaacagc ttccgcgcct accagcagtc gctggaggac     420
tggctggaga accgagacga cgccagaacc cgctcagttc tgtacacaca gtacatcgcc     480
ctagagctgg acttcctcaa cgctatgccg ctcttcgcca tccgtaacca ggaagtaccg     540
cttctgatgg tgtacgcaca agcagcgaac ctccatctgc cctgctgcg agacgcatct      600
ctgttcggca gtgagttcgg gctgacgagc caggagatcc agcgctacta cgagcgccaa     660
gtggagaaga ctcgtgagta cagcgactac tgcgcgcgct ggtacaacac gggcttgaac     720
aaccttcgcg gacaaacgc cgaatcctgg cttcgctaca accagttccg ccgcgacctc     780
acgctgggtg tgctggacct ggtcgcgctc ttcccgtcct acgacacacg ggtgtaccca     840
atgaacacga gcgcacagct cacccgtgag atctacacag atcccatcgg ccgcaccaac     900
gctcccagtg cttcgcaag cacgaattgg ttcaacaata cgctccttc tttctctgcc      960
atcgaggccg ctgtcatcag accgccgcac ttactcgatt ccccggagca gctcactatc    1020
ttctctgtgt tgtcccggtg gtcgaacacg cagtacatga actactgggt gggccacagg    1080
ctagagagcc ggaccatccg tggcagtctc tcaacctcga cccacggcaa cacgaacacg    1140
agcatcaacc ctgtcactct ccagtttaca tctagggacg tttacaggac agagtcgttc    1200
gctggcatta acattctgtt gaccactccg gtgaacggcg tcccttgggc ccgcttcaac    1260
tggaggaatc ctctgaactc actgcgcggc agccttctct acactatcgg ctacaccggc    1320
gttgggacgc aactcttcga ctcggagacc gagctgccgc ccgagaccac cgagcggcct    1380
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggaccttc    1620
gccttcagca acgtgaactt ggacttcaat tgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtgcgggaa cgaggtgtac gttgaccgtt cgagctgat cccggtcacc    1920
gccaccgatg ctaccttttga agcagagtcc gacttggaac gtgcacagaa ggcagtgaac    1980
```

```
gcactcttca cctcaagcaa ccagatcgga ttgaagacag atgtgacaga ttaccacatc    2040
gaccaagtga gcaacttggt ggattgcttg tcagatgagt tctgcttgga tgagaagcgt    2100
gaactctccg agaaggtgaa gcacgcaaag cgtctctcag atgaacgtaa tctccttcaa    2160
gaccctaact ttcgtggtat caatcgtcag ccagatcgtg gatggcgtgg atcaacagac    2220
atcaccatcc agggaggcga tgatgtgttc aaggagaact acgtgaccct cccaggaacc    2280
gtggatgaat gctacccaac ctacctctac cagaagatcg acgagtcaaa gctcaaggct    2340
tacacccgtt atgaactccg tggctacatc gaagatagcc aggatctcga atctatctc     2400 atccgttaca atgctaagca cgaaatcgtg aatgtgccag gaaccggctc actctggcca    2460
ctctcagcac agtcaccaat cggcaagtgc ggcgaaccca atcgctgcgc tcctcatctc    2520
gaatggaatc ccgatctcga ctgctcctgc cgagacggcg agaagtgtgc acatcactca    2580
caccacttca ccctcgacat cgacgtgggc tgcaccgacc tcaatgaaga cctgggcgtg    2640
tgggtgatct tcaagatcaa gacccaggac ggccacgcac gactgggcaa tctggagttt    2700
ctggaggaga agccactgct tggcgaggca ctggcacgag tgaaacgagc cgagaagaaa    2760
tggcgagaca aacgtgagaa gctgcaactg gagaccaaca tcgtgtacaa agaggccaaa    2820
gagtcagttg acgccctgtt tgtcaatagc agtatgacc gactgcaagt tgacaccaac     2880
atcgccatga tccacgctgc ggacaagcgc gtccaccgca tccgcgaggc ttatctgccc    2940
gagctgagcg tcattcccgg cgtcaatgcc gcgatcttcg aggagttaga gggccgcatc    3000
ttcaccgcct acagcctcta tgacgcccgc aatgtcatta gaatggcga cttcaacaat     3060 ggcttactat gctggaatgt caaagggcac gttgacgtcg aggagcagaa caataccgc     3120 agcgtcttag tcatacccga gtgggaggcc gaagtcagcc aggaagtccg cgtctgtcca    3180
gggcgcgggt acatcctgcg ggtcaccgcc tacaaagagg gatacggcga gggttgtgtc    3240
accatacacg agatagagga caataccgac gaactcaagt tcagcaattg tgtcgaggag    3300
gaagtctatc ccaacaatac cgtaacctgc aacaactaca ccggaaccca ggaggagtat    3360
gaagggacgt acacctcgcg gaaccagggc tatgacgaag cctatgggaa caacccgtcg    3420
gtgcctgctg actatgcgtc ggtctatgag gagaaatcgt acacgacgg gcggcgggag    3480 aatccgtgtg agtcgaatcg cgggtatggt gactacacgc cgctaccggc gggctatgta    3540
acgaaagacc tggaatactt cccggagacg gacaaagtat ggatagagat aggcgagacg    3600
gagggaacgt tcatcgtgga ctcggtagag ctgctgctca tggaggagtg a             3651
```

<210> SEQ ID NO 25
<211> LENGTH: 1216
<212> TYPE: PRT
<213> ORGANISM: Artificial
<220> FEATURE:
<223> OTHER INFORMATION: Amino acid sequence of the chimeric protein variant TIC867_25.

<400> SEQUENCE: 25

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60
```

-continued

```
Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                 85                  90                  95

Trp Glu Ile Phe Leu Glu His Val Gln Leu Ile Arg Gln Gln Val
            100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
```

-continued

```
            485                 490                 495
Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Pro Phe Ala Phe Ser Asn
            530                 535             540

Val Asn Leu Asp Phe Asn Leu Ser Gln Arg Tyr Arg Ala Arg Ile Arg
545             550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
                595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Asp Ala Thr Phe Glu Ala Glu Ser Asp Leu Glu Arg Ala Gln
                    645                 650                 655

Lys Ala Val Asn Ala Leu Phe Thr Ser Ser Asn Gln Ile Gly Leu Lys
                660                 665                 670

Thr Asp Val Thr Asp Tyr His Ile Asp Gln Val Ser Asn Leu Val Asp
                675                 680                 685

Cys Leu Ser Asp Glu Phe Cys Leu Asp Glu Lys Arg Glu Leu Ser Glu
            690                 695                 700

Lys Val Lys His Ala Lys Arg Leu Ser Asp Glu Arg Asn Leu Leu Gln
705                 710                 715                 720

Asp Pro Asn Phe Arg Gly Ile Asn Arg Gln Pro Asp Arg Gly Trp Arg
                    725                 730                 735

Gly Ser Thr Asp Ile Thr Ile Gln Gly Gly Asp Asp Val Phe Lys Glu
                740                 745                 750

Asn Tyr Val Thr Leu Pro Gly Thr Val Asp Glu Cys Tyr Pro Thr Tyr
                755                 760                 765

Leu Tyr Gln Lys Ile Asp Glu Ser Lys Leu Lys Ala Tyr Thr Arg Tyr
            770                 775                 780

Glu Leu Arg Gly Tyr Ile Glu Asp Ser Gln Asp Leu Glu Ile Tyr Leu
785                 790                 795                 800

Ile Arg Tyr Asn Ala Lys His Glu Ile Val Asn Val Pro Gly Thr Gly
                805                 810                 815

Ser Leu Trp Pro Leu Ser Ala Gln Ser Pro Ile Gly Lys Cys Gly Glu
            820                 825                 830

Pro Asn Arg Cys Ala Pro His Leu Glu Trp Asn Pro Asp Leu Asp Cys
                835                 840                 845

Ser Cys Arg Asp Gly Glu Lys Cys Ala His His Ser His His Phe Thr
            850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Arg Leu Gly
                885                 890                 895

Asn Leu Glu Phe Leu Glu Glu Lys Pro Leu Leu Gly Glu Ala Leu Ala
            900                 905                 910
```

-continued

Arg Val Lys Arg Ala Glu Lys Lys Trp Arg Asp Lys Arg Glu Lys Leu
        915                 920                 925

Gln Leu Glu Thr Asn Ile Val Tyr Lys Glu Ala Lys Glu Ser Val Asp
    930                 935                 940

Ala Leu Phe Val Asn Ser Gln Tyr Asp Arg Leu Gln Val Asp Thr Asn
945                 950                 955                 960

Ile Ala Met Ile His Ala Ala Asp Lys Arg Val His Arg Ile Arg Glu
            965                 970                 975

Ala Tyr Leu Pro Glu Leu Ser Val Ile Pro Gly Val Asn Ala Ala Ile
        980                 985                 990

Phe Glu Glu Leu Glu Gly Arg Ile Phe Thr Ala Tyr Ser Leu Tyr Asp
        995                1000                1005

Ala Arg Asn Val Ile Lys Asn Gly Asp Phe Asn Asn Gly Leu Leu
    1010                1015                1020

Cys Trp Asn Val Lys Gly His Val Asp Val Glu Glu Gln Asn Asn
    1025                1030                1035

His Arg Ser Val Leu Val Ile Pro Glu Trp Glu Ala Glu Val Ser
    1040                1045                1050

Gln Glu Val Arg Val Cys Pro Gly Arg Gly Tyr Ile Leu Arg Val
    1055                1060                1065

Thr Ala Tyr Lys Glu Gly Tyr Gly Glu Gly Cys Val Thr Ile His
    1070                1075                1080

Glu Ile Glu Asp Asn Thr Asp Glu Leu Lys Phe Ser Asn Cys Val
    1085                1090                1095

Glu Glu Glu Val Tyr Pro Asn Asn Thr Val Thr Cys Asn Asn Tyr
    1100                1105                1110

Thr Gly Thr Gln Glu Glu Tyr Glu Gly Thr Tyr Thr Ser Arg Asn
    1115                1120                1125

Gln Gly Tyr Asp Glu Ala Tyr Gly Asn Asn Pro Ser Val Pro Ala
    1130                1135                1140

Asp Tyr Ala Ser Val Tyr Glu Glu Lys Ser Tyr Thr Asp Gly Arg
    1145                1150                1155

Arg Glu Asn Pro Cys Glu Ser Asn Arg Gly Tyr Gly Asp Tyr Thr
    1160                1165                1170

Pro Leu Pro Ala Gly Tyr Val Thr Lys Asp Leu Glu Tyr Phe Pro
    1175                1180                1185

Glu Thr Asp Lys Val Trp Ile Glu Ile Gly Glu Thr Glu Gly Thr
    1190                1195                1200

Phe Ile Val Asp Ser Val Glu Leu Leu Leu Met Glu Glu
    1205                1210                1215

<210> SEQ ID NO 26
<211> LENGTH: 3600
<212> TYPE: DNA
<213> ORGANISM: Artificial
<220> FEATURE:
<223> OTHER INFORMATION: Recombinant nucleotide sequence used for
      expression in a bacterial cell encoding TIC868.

<400> SEQUENCE: 26
atgacttcaa ataggaaaaa tgagaatgaa attataaatg ctttatcgat tccagctgta     60
tcgaatcatt ccgcacaaat gaatctatca accgatgctc gtattgagga tagcttgtgt    120
atagccgagg ggaacaatat cgatccattt gttagcgcat caacagtcca acgggtatt    180 aacatagctg gtagaatact aggtgtatta ggcgtaccgt ttgctggaca aatagctagt    240

```
ttttatagtt ttcttgttgg tgaattatgg ccccgcggca gagatccttg ggaaattttc      300
ctagaacatg tcgaacaact tataagacaa caagtaacag aaaatactag ggatacggct      360
cttgctcgat tacaaggttt aggaaattcc tttagagcct atcaacagtc acttgaagat      420
tggctagaaa accgtgatga tgcaagaacg agaagtgttc tttatacccca atatatagcc      480 ttagaacttg attttcttaa tgcgatgccg cttttcgcaa ttagaaacca agaagttcca      540
ttattaatgg tatatgctca agctgcaaat ttacacctat tattattgag agatgcctct      600 cttttggta gtgaatttgg gcttacatcc caagaaattc aacgttatta tgagcgccaa      660
gtggaaaaaa cgagagaata ttctgattat tgcgcaagat ggtataatac gggtttaaat      720
aatttgagag ggacaaatgc tgaaagttgg ttgcgatata atcaattccg tagagactta      780
acgctaggag tattagatct agtggcacta ttcccaagct atgacacgcg tgtttatcca      840
atgaatacca gtgctcaatt aacaagagaa atttatacag atccaattgg gagaacaaat      900
gcaccttcag gatttgcaag tacgaattgg tttaataata atgcaccatc gttttctgcc      960
atagaggctg ccgttattag gcctccgcat ctacttgatt ttccagaaca gcttacaatt     1020
ttcagcgtat taagtcgatg gagtaatact caatatatga attactgggt gggacataga     1080
cttgaatcgc gaacaataag ggggtcatta agtacctcga cacacggaaa taccaatact     1140
tctattaatc ctgtaacatt acagttcaca tctcgagacg tttatagaac agaatcattt     1200
gcagggataa atatacttct aactactcct gtgaatggag taccttgggc tagatttaat     1260
tggagaaatc ccctgaattc tcttagaggt agccttctct atactatagg gtatactgga     1320
gtggggacac aactatttga ttcagaaact gaattaccac cagaaacaac agaacgacca     1380
aattatgaat cttacagtca tagattatct aatataagac taatatcagg aaacactttg     1440
agagcaccag tatattcttg gacgcaccgt agtgcagatc gtacaaatac cattagttca     1500
gatagcatta tcaaatacc tttagtgaaa ggatttagag tttgggggg cacctctgtc     1560 attacaggac caggatttac aggaggggat atccttcgaa gaaatacctt tggtgatttt     1620
gtatctctac aagtcaatat taattcacca attacccaaa gataccgttt aagatttcgt     1680
tacgcttcca gtagggatgc acgagttata gtattaacag gagcggcatc cacaggagtg     1740
ggaggccaag ttagtgtaaa tatgcctctt cagaaaacta tggaaatagg ggagaactta     1800
acatctagaa catttagata taccgatttt agtaatcctt tttcatttag agctaatcca     1860
gatataattg ggataagtga acaacctcta tttggtgcag gttctattag tagcggtgaa     1920
ctttatatag ataaaattga aattattcta gcagatgcaa catttgaagc agaatctgat     1980
ttagaaagag cacaaaaggc ggtgaatgag ctgtttactt cttccaatca aatcgggtta     2040
aaaacagatg tgacggatta tcatattgat caagtatcca atttagttga gtgtttatct     2100
gatgaatttt gtctggatga aaaaaagaa ttgtccgaga agtcaaaca tgcgaagcga     2160 cttagtgatg agcggaattt acttcaagat ccaaacttta gagggatcaa tagacaacta     2220
gaccgtggct ggagaggaag tacggatatt accatccaag gaggcgatga cgtattcaaa     2280
gagaattacg ttacgctatt gggtacccttt gatgagtgct atccaacgta tttatatcaa     2340
aaaatagatg agtcgaaatt aaaagcctat acccgttacc aattaagagg gtatatcgaa     2400
gatagtcaag acttagaaat ctatttaatt cgctacaatg ccaaacacga aacagtaaat     2460
gtgccaggta cgggttcctt atggccgctt tcagccccaa gtccaatcgg aaaatgtgcc     2520
catcattccc atcatttctc cttggacatt gatgttggat gtacagactt aaatgaggac     2580
```

| | |
|---|---|
| ttaggtgtat gggtgatatt caagattaag acgcaagatg gccatgcaag actaggaaat | 2640 |
| ctagaatttc tcgaagagaa accattagta ggagaagcac tagctcgtgt gaaaagagcg | 2700 |
| gagaaaaaat ggagagacaa acgtgaaaaa ttggaatggg aaacaaatat tgtttataaa | 2760 |
| gaggcaaaag aatctgtaga tgctttattt gtaaactctc aatatgatag attacaagcg | 2820 |
| gataccaaca tcgcgatgat tcatgcggca gataaacgcg ttcatagcat tcgagaagct | 2880 |
| tatctgcctg agctgtctgt gattccgggt gtcaatgcgg ctattttga agaattagaa | 2940 |
| gggcgtattt tcactgcatt ctccctatat gatgcgagaa atgtcattaa aaatggtgat | 3000 |
| tttaataatg gcttatcctg ctggaacgtg aaagggcatg tagatgtaga agaacaaaac | 3060 |
| aaccaccgtt cggtccttgt tgttccggaa tgggaagcag aagtgtcaca agaagttcgt | 3120 |
| gtctgtccgg gtcgtggcta tatccttcgt gtcacagcgt acaaggaggg atatggagaa | 3180 |
| ggttgcgtaa ccattcatga gatcgagaac aatacagacg aactgaagtt tagcaactgt | 3240 |
| gtagaagagg aagtatatcc aaacaacacg gtaacgtgta atgattatac tgcgactcaa | 3300 |
| gaagaatatg agggtacgta cacttctcgt aatcgaggat atgacggagc ctatgaaagc | 3360 |
| aattcttctg taccagctga ttatgcatca gcctatgaag aaaaagcata tacagatgga | 3420 |
| cgaagagaca atccttgtga atctaacaga ggatatgggg attacacacc actaccagct | 3480 |
| ggctatgtga caaaagaatt agagtacttc ccagaaaccg ataaggtatg gattgagatc | 3540 |
| ggagaaacgg aaggaacatt catccgtgga cagcgtggaat tacttcttat ggaggaatag | 3600 |

<210> SEQ ID NO 27
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868.

<400> SEQUENCE: 27

| | |
|---|---|
| atgacgagca accggaagaa cgagaacgag atcatcaacg ccctctcgat ccctgctgtt | 60 |
| tcaaaccact ccgcgcagat gaacctgtcc accgacgcgc gcatcgagga ctccctctgc | 120 |
| atagccgagg caacaacat cgacccattc gtgtcggcca gcacggttca gaccggcatc | 180 |
| aacatcgcgg gccgtatcct cggcgtcctc ggtgtcccat cgccggtca gatcgcgtcc | 240 |
| ttctactcgt tccttgtggg cgagctgtgg cctcgcggtc gtgacccgtg ggagatcttc | 300 |
| ctggagcatg tggagcagtt gatccggcag caagtcacgg agaacacccg cgatactgct | 360 |
| ctggccaggc tacagggcct gggaaactcc tttcgggcat accagcagtc actggaggac | 420 |
| tggttggaga acagggatga cgcgcgaaca cgctcggtac tctacaccca gtacatcgct | 480 |
| ctcgaactcg acttcctgaa cgctatgccg ctgttcgcca tcaggaacca ggaagttcca | 540 |
| ctccttatgg tgtacgccca ggccgccaac ttacatctgc tcctgctgcg ggacgccagc | 600 |
| ctgttcggct ccgagttcgg actcacatct caagaaatcc agcgttacta cgagcgccaa | 660 |
| gtggagaaga cccgtgagta cagtgactac tgcgctcgat ggtacaacac agggctcaac | 720 |
| aacctgcgcg gcaccaacgc tgagtcatgg ctccgttaca accagttccg ccgcgacttg | 780 |
| actttgggtg tcctagacct ggtggcgcta ttcccgtctt acgacacacg ggtgtaccca | 840 |
| atgaacacta gcgcgcaact cacgcgggag atctacacag acccaatcgg ccggacgaac | 900 |
| gcaccctccg gtttcgcatc cacgaattgg ttcaacaaca acgcaccctc cttctcggca | 960 |
| atcgaggccg ccgtcatccg ccctcctcac ctgctcgact ttcccgagca gctcacgatc | 1020 |

```
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtctgac   1980
ctggagcggg ctcagaaggc tgtcaacgaa ctgttcacca gcagcaacca gattgggctc   2040
aagaccgacg tcacggacta tcacattgac caagtgtcca accttgtgga gtgcctgtcc   2100
gacgagttct gcctcgacga aagaaggag ctgtccgaga ggtcaaaaca cgcgaagcgt   2160
ctgagtgacg agcggaattt gctccaggac ccgaacttcc gtggcatcaa ccgccagctc   2220
gaccgtggtt ggcgcgggag tacagacatc accatccagg gaggcgacga tgtgttcaag   2280
gagaactatg tgacgctgct cgggactttc gacgaatgct acccgacgta tctctaccag   2340
aagatagacg agagtaaatt gaaggcgtac acccgctacc agcttcgcgg gtacatcgag   2400
gatagtcagg acctggaaat ctacctgatc cgatacaacg ccaagcacga gacagtgaac   2460
gtgccaggca cgggctcact ttggccattg agcgctccct ctccaatcgg aaagtgcgct   2520
caccactcgc accacttctc tctggacatc gacgtgggct gcaccgacct caacgaggac   2580
ctgggtgtct gggttatctt caagattaag acccaggacg gacatgcccg cctcggcaac   2640
ctggagttcc ttgaggagaa gcctctcgtg ggcgaggccc tcgctcgtgt gaagcgcgcc   2700
gagaagaaat ggcgagacaa gcgggagaag ctggagtggg agaccaacat cgtgtacaag   2760
gaggccaagg agtcagtgga cgcactcttc gtcaacagcc agtacgaccg cctccaggct   2820
gacaccaaca tcgccatgat ccacgcggct gacaagcggg tccacagcat ccgtgaggcg   2880
tacctgcccg agctgtcagt gatccctggt gtgaacgcgg cgatcttcga ggaactggag   2940
ggccgcatct tcacagcatt cagcctgtac gatgccagga atgttattaa gaacggtgac   3000
ttcaacaacg ggctgagttg ctggaacgtc aagggccatg tggacgtcga ggagcagaac   3060
aaccaccggt ccgtgctggt cgtgccggag tgggaggcag aggtgagcca ggaggtccgc   3120
gtctgccctg gtcgcggcta catcctccgt gtgactgcgt acaaggaagg ctacggtgaa   3180
ggctgcgtga ctatccacga gatcgagaac aacaccgacg agctcaagtt ctcgaactgt   3240
gtggaggagg aggtgtaccc gaacaacacc gttacttgca acgactacac tgccacgcaa   3300
gaggagtaca agggcactta cacttcccgg aatcgcggct atgatggcgc gtacgagtcc   3360
aacagcagcg tgcctgcgga ttatgcgtcc gcttacgagg agaaggcgta caccgacgga   3420
```

```
cggagggaca  accettgcga  gtccaaccgt  ggctacggtg  actacactcc  gctgcccgcc      3480
gggtacgtca  ccaaggagct  ggagtacttc  ccggagaccg  acaaagtctg  gatcgagatc      3540
ggcgagacgg  agggcacttt  catcgtggac  tcggtcgagc  tgctactgat  ggaggagtga      3600
```

<210> SEQ ID NO 28
<211> LENGTH: 1199
<212> TYPE: PRT
<213> ORGANISM: Artificial
<220> FEATURE:
<223> OTHER INFORMATION: Amino acid sequence of the chimeric protein TIC868.

<400> SEQUENCE: 28

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
```

```
                    325                 330                 335
Gln Leu Thr Ile Phe Ser Val Leu Ser Arg Trp Ser Asn Thr Gln Tyr
                340                 345                 350
Met Asn Tyr Trp Val Gly His Arg Leu Glu Ser Arg Thr Ile Arg Gly
                355                 360                 365
Ser Leu Ser Thr Ser Thr His Gly Asn Thr Asn Thr Ser Ile Asn Pro
370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
                435                 440                 445
Glu Thr Glu Leu Pro Pro Glu Thr Thr Glu Arg Pro Asn Tyr Glu Ser
                450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Asn Gln Ile Pro Leu Val Lys Gly Phe
                500                 505                 510
Arg Val Trp Gly Gly Thr Ser Val Ile Thr Gly Pro Gly Phe Thr Gly
                515                 520                 525
Gly Asp Ile Leu Arg Arg Asn Thr Phe Gly Asp Phe Val Ser Leu Gln
                530                 535                 540
Val Asn Ile Asn Ser Pro Ile Thr Gln Arg Tyr Arg Leu Arg Phe Arg
545                 550                 555                 560
Tyr Ala Ser Ser Arg Asp Ala Arg Val Ile Val Leu Thr Gly Ala Ala
                565                 570                 575
Ser Thr Gly Val Gly Gly Gln Val Ser Val Asn Met Pro Leu Gln Lys
                580                 585                 590
Thr Met Glu Ile Gly Glu Asn Leu Thr Ser Arg Thr Phe Arg Tyr Thr
                595                 600                 605
Asp Phe Ser Asn Pro Phe Ser Phe Arg Ala Asn Pro Asp Ile Ile Gly
                610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Phe Glu
                645                 650                 655
Ala Glu Ser Asp Leu Glu Arg Ala Gln Lys Ala Val Asn Glu Leu Phe
                660                 665                 670
Thr Ser Ser Asn Gln Ile Gly Leu Lys Thr Asp Val Thr Asp Tyr His
                675                 680                 685
Ile Asp Gln Val Ser Asn Leu Val Glu Cys Leu Ser Asp Glu Phe Cys
                690                 695                 700
Leu Asp Glu Lys Lys Glu Leu Ser Glu Lys Val Lys His Ala Lys Arg
705                 710                 715                 720
Leu Ser Asp Glu Arg Asn Leu Leu Gln Asp Pro Asn Phe Arg Gly Ile
                725                 730                 735
Asn Arg Gln Leu Asp Arg Gly Trp Arg Gly Ser Thr Asp Ile Thr Ile
                740                 745                 750
```

-continued

Gln Gly Gly Asp Asp Val Phe Lys Glu Asn Tyr Val Thr Leu Leu Gly
    755                 760                 765

Thr Phe Asp Glu Cys Tyr Pro Thr Tyr Leu Tyr Gln Lys Ile Asp Glu
770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
                820                 825                 830

Pro Ser Pro Ile Gly Lys Cys Ala His His Ser His His Phe Ser Leu
                835                 840                 845

Asp Ile Asp Val Gly Cys Thr Asp Leu Asn Glu Asp Leu Gly Val Trp
850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
                900                 905                 910

Trp Glu Thr Asn Ile Val Tyr Lys Glu Ala Lys Glu Ser Val Asp Ala
                915                 920                 925

Leu Phe Val Asn Ser Gln Tyr Asp Arg Leu Gln Ala Asp Thr Asn Ile
930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
                980                 985                 990

Arg Asn Val Ile Lys Asn Gly Asp Phe Asn Asn Gly Leu Ser Cys Trp
                995                 1000                1005

Asn Val Lys Gly His Val Asp Val Glu Glu Gln Asn Asn His Arg
    1010                1015                1020

Ser Val Leu Val Val Pro Glu Trp Glu Ala Glu Val Ser Gln Glu
    1025                1030                1035

Val Arg Val Cys Pro Gly Arg Gly Tyr Ile Leu Arg Val Thr Ala
    1040                1045                1050

Tyr Lys Glu Gly Tyr Gly Glu Gly Cys Val Thr Ile His Glu Ile
    1055                1060                1065

Glu Asn Asn Thr Asp Glu Leu Lys Phe Ser Asn Cys Val Glu Glu
    1070                1075                1080

Glu Val Tyr Pro Asn Asn Thr Val Thr Cys Asn Asp Tyr Thr Ala
    1085                1090                1095

Thr Gln Glu Glu Tyr Glu Gly Thr Tyr Thr Ser Arg Asn Arg Gly
    1100                1105                1110

Tyr Asp Gly Ala Tyr Glu Ser Asn Ser Ser Val Pro Ala Asp Tyr
    1115                1120                1125

Ala Ser Ala Tyr Glu Glu Lys Ala Tyr Thr Asp Gly Arg Arg Asp
    1130                1135                1140

Asn Pro Cys Glu Ser Asn Arg Gly Tyr Gly Asp Tyr Thr Pro Leu
    1145                1150                1155

| | | | | | | | | | | | |
|---|---|---|---|---|---|---|---|---|---|---|---|
|Pro|Ala|Gly|Tyr|Val|Thr|Lys|Glu|Leu|Glu|Tyr|Phe|Pro|Glu|Thr|
| |1160| | | | |1165| | | |1170| | | | |

| | | | | | | | | | | | |
|---|---|---|---|---|---|---|---|---|---|---|---|
|Asp|Lys|Val|Trp|Ile|Glu|Ile|Gly|Glu|Thr|Glu|Gly|Thr|Phe|Ile|
| |1175| | | | |1180| | | |1185| | | | |

| | | | | | | | | |
|---|---|---|---|---|---|---|---|---|
|Val|Asp|Ser|Val|Glu|Leu|Leu|Leu|Met|Glu|Glu|
| |1190| | | | |1195| | | | |

<210> SEQ ID NO 29
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_9.

<400> SEQUENCE: 29

| | | |
|---|---|---|
|atgacgagca accggaagaa cgagaacgag atcatcaacg ccctctcgat ccctgctgtt|60|
|tcaaaccact ccgcgcagat gaacctgtcc accgacgcgc gcatcgagga ctccctctgc|120|
|atagccgagg gcaacaacat cgacccattc gtgtcggcca gcacggttca gaccggcatc|180|
|aacatcgcgg gccgtatcct cggcgtcctc ggtgtcccat cgccggtca gatcgcgtcc|240|
|ttctactcgt tccttgtggg cgagctgtgg cctcgcggtc gtgaccgtg ggagatcttc|300|
|ctggagcatg tggagcagtt gatccggcag caagtcacgg agaacacccg cgatactgct|360|
|ctggccaggc tacagggcct gggaaactcc tttcgggcat accagcagtc actgaggac|420|
|tggttggaga cagggatga cgcgcgaaca cgctcggtac tctacaccca gtacatcgct|480|
|ctcgaactcg acttcctgaa cgctatgccg ctgttcgcca tcaggaacca ggaagttcca|540|
|ctccttatgg tgtacgccca ggccgccaac ttacatctgc cctgctgcg ggacgccagc|600|
|ctgttcggct ccgagttcgg actcacatct caagaaatcc agcgttacta cgagcgccaa|660|
|gtggagaaga cccgtgagta cagtgactac tgcgctcgat ggtacaacac agggctcaac|720|
|agcctgcgcg gcaccaacgc tgagtcatgg ctccgttaca accagttccg ccgcgacttg|780|
|actttgggtg tcctagacct ggtggcgcta ttcccgtctt acgacacacg ggtgtaccca|840|
|atgaacacta gcgcgcaact cacgcgggag atctacacag cccaatcgg ccggacgaac|900|
|gcaccctccg gtttcgcatc cacgaattgg ttcaacaaca cgcaccctc cttctcggca|960|
|atcgaggccg ccgtcatccg ccctcctcac ctgctcgact ttcccgagca gctcacgatc|1020|
|ttctccgtgc tctcacgctg gtccaacaca cagtacatga actactgggt cgggcaccga|1080|
|ttggagagta ggacgatccg tggcagcttg agcaccagta cccacggcaa caccaacacc|1140|
|tccatcaacc cagttacgct acagttcacg agccgcgacg tttaccggac tgagtcgcag|1200|
|gcgggcatta acatccttat gacaacgccc gtcaacggcg tcccgtgggc ccggttcaac|1260|
|tggcgtaacc cgaagaactc cctgcgcggg tcattgctct acaccatcgg gtacacgggc|1320|
|gtcggcaccc agctcttcga cagtgaaact gagctgccgc cgagaccac ggaacgcccg|1380|
|aactacgagt cctacagcca ccgcctgtcc aacatccggc tcatctctgg caacacgctc|1440|
|cgtgcgccgg tgtactcctg gacacaccgc agcgccgacc ggaccaacac gatctcttcc|1500|
|gactccatta accagatccc gctcgtgaag ggcttccgtg tgtggggtgg cacgagcgtc|1560|
|atcaccggtc cgggcttcac cggtggagac atactgcggc gcaacacttt cggcgacttc|1620|
|gtttcgttgc aagtgaacat caactcgccg atcacccagc gttaccgtct gaggttccgc|1680|
|tacgcttcaa gccgcgacgc gagggtcatt gtcctgaccg gagccgcgtc cacaggcgtg|1740|
|ggaggccaag tctcagtcaa catgcctctc cagaagacga tggagatagg cgagaacttg|1800|

-continued

```
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgttcgaggc cgagtctgac    1980
ctggagcggg ctcagaaggc tgtcaacgaa ctgttcacca gcagcaacca gattgggctc    2040
aagaccgacg tcacggacta tcacattgac caagtgtcca accttgtgga gtgcctgtcc    2100
gacgagttct gcctcgacga gaagaaggag ctgtccgaga aggtcaaaca cgcgaagcgt    2160
ctgagtgacg agcggaattt gctccaggac ccgaacttcc gtggcatcaa ccgccagctc    2220
gaccgtggtt ggcgcgggag tacagacatc accatccagg gaggcgacga tgtgttcaag    2280
gagaactatg tgacgctgct cgggactttc gacgaatgct acccgacgta tctctaccag    2340
aagatagacg agagtaaatt gaaggcgtac acccgctacc agcttcgcgg gtacatcgag    2400
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg acatgcccg cctcggcaac    2640
ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
gaggccaagg agtcagtgga cgcactcttc gtcaacagcc agtacgaccg cctccaggct    2820
gacaccaaca tcgccatgat ccacgcggct gacaagcggg tccacagcat ccgtgaggcg    2880
tacctgcccg agctgtcagt gatccctggt gtgaacgcgg cgatcttcga ggaactggag    2940
ggccgcatct tcacagcatt cagcctgtac gatgccagga atgttattaa gaacggtgac    3000
ttcaacaacg ggctgagttg ctggaacgtc aagggccatg tggacgtcga ggagcagaac    3060
aaccaccggt ccgtgctggt cgtgccgag tgggaggcag aggtgagcca ggaggtccgc    3120
gtctgccctg gtcgcggcta catcctccgt gtgactgcgt acaaggaagg ctacggtgaa    3180
ggctgcgtga ctatccacga gatcgagaac aacaccgacg agctcaagtt ctcgaactgt    3240
gtggaggagg aggtgtaccc gaacaacacc gttacttgca acgactacac tgccacgcaa    3300
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca accccttgcga gtccaaccgt ggctacggtg actacactcc gctgcccgcc    3480
gggtacgtca ccaaggagct ggagtacttc ccggagaccg acaaagtctg gatcgagatc    3540
ggcgagacgg agggcacttt catcgtggac tcggtcgagc tgctactgat ggaggagtga    3600
```

<210> SEQ ID NO 30
<211> LENGTH: 1199
<212> TYPE: PRT
<213> ORGANISM: Artificial
<220> FEATURE:
<223> OTHER INFORMATION: Amino acid sequence of the chimeric protein variant TIC868_9.

<400> SEQUENCE: 30

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp

```
                35                  40                  45
Pro Phe Val Ser Ala Ser Thr Val Gln Thr Gly Ile Asn Ile Ala Gly
 50                  55                  60

Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                 85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Ser Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
                275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Gln
385                 390                 395                 400

Ala Gly Ile Asn Ile Leu Met Thr Thr Pro Val Asn Gly Val Pro Trp
                405                 410                 415

Ala Arg Phe Asn Trp Arg Asn Pro Lys Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460
```

```
Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
            515                 520                 525

Gly Asp Ile Leu Arg Arg Asn Thr Phe Gly Asp Phe Val Ser Leu Gln
        530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
            645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
            725                 730                 735

Asn Arg Gln Leu Asp Arg Gly Trp Arg Gly Ser Thr Asp Ile Thr Ile
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
        770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
            805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
            835                 840                 845

Asp Ile Asp Val Gly Cys Thr Asp Leu Asn Glu Asp Leu Gly Val Trp
    850                 855                 860

Val Ile Phe Lys Ile Lys Thr Gln Asp Gly His Ala Arg Leu Gly Asn
865                 870                 875                 880
```

| | | | | | | | | | | | |
|---|---|---|---|---|---|---|---|---|---|---|---|
|Leu|Glu|Phe|Leu|Glu|Glu|Lys|Pro|Leu|Val|Gly|Glu|Ala|Leu|Ala|Arg|
| | | | |885| | | |890| | | |895| | | |
|Val|Lys|Arg|Ala|Glu|Lys|Lys|Trp|Arg|Asp|Lys|Arg|Glu|Lys|Leu|Glu|
| | | |900| | | | |905| | | | |910| | |

```
Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
        915                 920                 925

Leu Phe Val Asn Ser Gln Tyr Asp Arg Leu Gln Ala Asp Thr Asn Ile
    930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
            965                 970                 975

Glu Glu Leu Glu Gly Arg Ile Phe Thr Ala Phe Ser Leu Tyr Asp Ala
        980                 985                 990

Arg Asn Val Ile Lys Asn Gly Asp Phe Asn Asn Gly Leu Ser Cys Trp
    995                 1000                1005

Asn Val Lys Gly His Val Asp Val Glu Glu Gln Asn Asn His Arg
    1010                1015                1020

Ser Val Leu Val Val Pro Glu Trp Glu Ala Glu Val Ser Gln Glu
    1025                1030                1035

Val Arg Val Cys Pro Gly Arg Gly Tyr Ile Leu Arg Val Thr Ala
    1040                1045                1050

Tyr Lys Glu Gly Tyr Gly Glu Gly Cys Val Thr Ile His Glu Ile
    1055                1060                1065

Glu Asn Asn Thr Asp Glu Leu Lys Phe Ser Asn Cys Val Glu Glu
    1070                1075                1080

Glu Val Tyr Pro Asn Asn Thr Val Thr Cys Asn Asp Tyr Thr Ala
    1085                1090                1095

Thr Gln Glu Glu Tyr Glu Gly Thr Tyr Thr Ser Arg Asn Arg Gly
    1100                1105                1110

Tyr Asp Gly Ala Tyr Glu Ser Asn Ser Ser Val Pro Ala Asp Tyr
    1115                1120                1125

Ala Ser Ala Tyr Glu Glu Lys Ala Tyr Thr Asp Gly Arg Arg Asp
    1130                1135                1140

Asn Pro Cys Glu Ser Asn Arg Gly Tyr Gly Asp Tyr Thr Pro Leu
    1145                1150                1155

Pro Ala Gly Tyr Val Thr Lys Glu Leu Glu Tyr Phe Pro Glu Thr
    1160                1165                1170

Asp Lys Val Trp Ile Glu Ile Gly Glu Thr Glu Gly Thr Phe Ile
    1175                1180                1185

Val Asp Ser Val Glu Leu Leu Leu Met Glu Glu
    1190                1195

<210> SEQ ID NO 31
<211> LENGTH: 3678
<212> TYPE: DNA
<213> ORGANISM: Artificial
<220> FEATURE:
<223> OTHER INFORMATION: Recombinant nucleotide sequence used for
      expression in a bacterial cell encoding TIC868_10.

<400> SEQUENCE: 31
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca aacgggtatt     180
```

```
aacatagctg gtagaatact aggtgtatta ggcgtaccgt ttgctggaca aatagctagt    240
ttttatagtt ttcttgttgg tgaattatgg ccccgcggca gagatccttg ggaaattttc    300
ctagaacatg tcgaacaact tataagacaa caagtaacag aaaatactag ggatacggct    360
cttgctcgat tacaaggttt aggaaattcc tttagagcct atcaacagtc acttgaagat    420
tggctagaaa accgtgatga tgcaagaacg agaagtgttc tttataccca atatatagcc    480
ttagaacttg attttcttaa tgcgatgccg cttttcgcaa ttagaaacca agaagttcca    540
ttattaatgg tatatgctca agctgcaaat ttacacctat tattattgag agatgcctct    600 cttttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag gacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttggggggg cacctctgtc   1560
attacaggac caggatttac aggaggggat atccttcgaa gaaataccct tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa catttgaggc agaatatgat   1980 ttagaaaagag cgcaaaaggt ggtgaatgcc ctgtttacgt ctacaaacca actagggcta   2040
aaaacagatg tgacggatta tcatattgat caggtatcca atctagttgc gtgtttatcg   2100
gatgaatttt gtctggatga aaagagagaa ttgtccgaga agttaaaaca tgcaaagcga   2160
ctcagtgatg agcggaattt acttcaagat ccaaacttca gagggatcaa taggcaacca   2220
gaccgtggct ggagaggaag tacgatatt actatccaag gaggagatga cgtattcaaa   2280
gagaattacg ttacgctacc gggtaccttt gatgagtgct atccaacgta tttatatcaa   2340
aaaatagatg agtcgaaatt aaaagcctat accgcttatc aattaagagg gtatatcgaa   2400
gatagtcaag acttagaaat ctatttaatt cgttacaatg caaaacacga aatagtaaat   2460
gtaccaggta caggaagttt atggcctctt tctgtagaaa atcaaattgg accttgtgga   2520
```

-continued

```
gaaccgaatc gatgcgcgcc acaccttgaa tggaatcctg atttacactg ttcctgcaga    2580
gacggggaaa aatgtgcaca tcattctcat catttctctt tggacattga tgttggatgt    2640
acagacttaa atgaggactt aggtgtatgg gtgatattca agattaagac gcaagatggc    2700
cacgcacgac tagggaatct agagtttctc gaagagaaac cattattagg agaagcacta    2760
gctcgtgtga aaagagcgga gaaaaatgg agagacaaac gcgaaacatt acaattggaa     2820
acaactatcg tttataaaga ggcaaaagaa tctgtagatg ctttatttgt aaactctcaa    2880
tatgatagat tacaagcgga tacgaacatc gcgatgattc atgcggcaga taaacgcgtt    2940
catagaattc gagaagcgta tctgccggag ctgtctgtga ttccgggtgt caatgcggct    3000
attttttgaag aattagaaga gcgtattttc actgcatttt ccctatatga tgcgagaaat    3060
attattaaaa atggcgattt caataatggc ttattatgct ggaacgtgaa agggcatgta    3120
gaggtagaag aacaaaacaa tcaccgttca gtcctggtta tcccagaatg ggaggcagaa    3180
gtgtcacaag aggttcgtgt ctgtccaggt cgtggctata tccttcgtgt tacagcgtac    3240
aaagagggat atggagaagg ttgcgtaacg atccatgaga tcgagaacaa tacagacgaa    3300
ctgaaattca caactgtgt agaagaggaa gtatatccaa acaacacggt aacgtgtatt     3360
aattatactg cgactcaaga agaatatgag ggtacgtaca cttctcgtaa tcgaggatat    3420
gacgaagcct atggtaataa cccttccgta ccagctgatt atgcgtcagt ctatgaagaa    3480
aaatcgtata cagatagacg aagagagaat ccttgtgaat ctaacagagg atatggagat    3540
tacacaccac taccagctgg ttatgtaaca aaggaattag agtacttccc agagaccgat    3600
aaggtatgga ttgagattgg agaaacagaa ggaacattca tcgtggacag cgtggaatta    3660
ctccttatgg aggaatag                                                  3678
```

<210> SEQ ID NO 32
<211> LENGTH: 3678
<212> TYPE: DNA
<213> ORGANISM: Artificial
<220> FEATURE:
<223> OTHER INFORMATION: Synthetic nucleotide sequence designed for
      expression in a plant cell encoding TIC868_10.

<400> SEQUENCE: 32

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg caacaacat cgacccattc gtgtcggcca gcacggttca gaccggcatc      180
aacatcgcgg ccgtatcct cggcgtcctc ggtgtcccat cgccggtca gatcgcgtcc       240
ttctactcgt tccttgtggg cgagctgtgg cctcgcggtc gtgaccgtg ggagatcttc       300
ctggagcatg tggagcagtt gatccggcag caagtcacgg agaacacccg cgatactgct     360
ctggccaggc tacagggcct gggaaactcc tttcgggcat accagcagtc actggaggac    420
tggttggaga cagggatga cgcgcgaaca cgctcggtac tctacacccca gtacatcgct    480
ctcgaactcg acttcctgaa cgctatgccg ctgttcgcca tcaggaacca ggaagttcca    540
ctccttatgg tgtacgccca ggccgccaac ttacatctgc cctgctgcg ggacgccagc     600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
acttgggtg tcctagacct ggtggcgcta ttcccgtctt acgacacacg ggtgtacca      840
```

```
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtacgac   1980
cttgagcgcg cccagaaggt ggtgaacgcc ctcttcacta gcactaacca gctaggcctg   2040
aagactgacg tgaccgacta ccacatcgac caagtgagca acctagtggc ctgcctctcc   2100
gacgagttct gcctcgacga gaagcgcgag ctgtccgaga aggtgaagca cgccaagcgc   2160
ctctccgacg agcgcaacct gctccaggac cccaacttca ggggcatcaa caggcagccc   2220
gaccgcggct ggcgcggctc caccgacatc accatccagg gcggtgacga cgtattcaag   2280
gagaactacg ttaccctccc cggcaccttc gacgagtgtt acccccaccta cctctaccag   2340
aagatcgacg agtccaagct gaaggcctac acccgctacc agctccgcgg ctacatcgag   2400
gactcccagg acctggaaat ctacctcatc cgctacaacg ccaagcacga gatcgtgaac   2460
gtgcctggca ccggcagcct ctggcctctc agcgtggaga accagatcgg cccttgcggc   2520
gagcctaacc gctgcgcccc tcacctcgag tggaaccctg acctccactg ctcgtgcagg   2580
gacggcgaga agtgcgccca ccatagccac cacttctctc tggacatcga cgtgggctgc   2640
accgacctga cgaggacct gggcgtgtgg gttatcttca agatcaagac ccaggacggt   2700
cacgccaggc tgggtaacct ggagttcctt gaggaaaagc ctctgctggg tgaggccctg   2760
gccagggtca agagggctga aagaaatgg agggataaga gggagaccct gcagctggag   2820
accactatcg tctacaagga ggctaaggag tctgtcgatg ctctgttcgt caactctcag   2880
tacgatagac tgcaagctga taccaacatc gctatgatcc acgctgcgga taagcgggtc   2940
caccggatcc gggaggctta ccttccggag ctttctgtca tcccgggtgt caacgctgcg   3000
atcttcgagg aacttgagga acggatcttc actgcgttta gtctttacga tgcgcggaac   3060
atcatcaaga acggggactt caacaatggt ctgctgtgct ggaacgtcaa gggtcatgtc   3120
gaggtcgagg aacaaaacaa tcatcgtagt gtccttgtca ttcctgagtg ggaggcggag   3180
gtctctcaag aggtccgtgt ttgcccgggg cgtgggtaca ttcttcgtgt tactgcgtac   3240
```

-continued

```
aaggaggggt acggggaggg gtgcgttact attcatgaga ttgagaacaa tactgatgag    3300
cttaagttca caattgtgt tgaggaggag gtttacccga acaatactgt tacgtgcatc    3360
aactacacgg caacgcaaga ggaatacgag gggacgtaca cctcgcgtaa tagagggtat    3420
gatgaggcgt acgaaacaa cccgtcggtt ccagcagatt atgcctcggt ttatgaggag    3480
aagtcgtaca cggatagacg acgcgagaat ccatgtgagt caaatcgagg atacggagat    3540
tacacaccat taccagcagg atacgttaca aaggagttgg aatacttccc ggaaacagat    3600
aaagtttgga ttgaaatcgg agaaacagaa ggaacattca tcgtcgactc agtagaattg    3660
ttgttgatgg aagaatga                                                  3678
```

<210> SEQ ID NO 33
<211> LENGTH: 1225
<212> TYPE: PRT
<213> ORGANISM: Artificial
<220> FEATURE:
<223> OTHER INFORMATION: Amino acid sequence of the chimeric protein
      variant TIC868_10.

<400> SEQUENCE: 33

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270
```

```
Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Tyr Asp Leu Glu Arg Ala Gln Lys Val Val Asn Ala Leu Phe
                660                 665                 670

Thr Ser Thr Asn Gln Leu Gly Leu Lys Thr Asp Val Thr Asp Tyr His
            675                 680                 685

Ile Asp Gln Val Ser Asn Leu Val Ala Cys Leu Ser Asp Glu Phe Cys
```

-continued

```
                690             695             700
Leu Asp Glu Lys Arg Glu Leu Ser Glu Lys Val Lys His Ala Lys Arg
705             710             715             720
Leu Ser Asp Glu Arg Asn Leu Leu Gln Asp Pro Asn Phe Arg Gly Ile
            725             730             735
Asn Arg Gln Pro Asp Arg Gly Trp Gly Ser Thr Asp Ile Thr Ile
            740             745             750
Gln Gly Gly Asp Asp Val Phe Lys Glu Asn Tyr Val Thr Leu Pro Gly
            755             760             765
Thr Phe Asp Glu Cys Tyr Pro Thr Tyr Leu Tyr Gln Lys Ile Asp Glu
            770             775             780
Ser Lys Leu Lys Ala Tyr Thr Arg Tyr Gln Leu Arg Gly Tyr Ile Glu
785             790             795             800
Asp Ser Gln Asp Leu Glu Ile Tyr Leu Ile Arg Tyr Asn Ala Lys His
            805             810             815
Glu Ile Val Asn Val Pro Gly Thr Gly Ser Leu Trp Pro Leu Ser Val
            820             825             830
Glu Asn Gln Ile Gly Pro Cys Gly Glu Pro Asn Arg Cys Ala Pro His
            835             840             845
Leu Glu Trp Asn Pro Asp Leu His Cys Ser Cys Arg Asp Gly Glu Lys
850             855             860
Cys Ala His His Ser His His Phe Ser Leu Asp Ile Asp Val Gly Cys
865             870             875             880
Thr Asp Leu Asn Glu Asp Leu Gly Val Trp Val Ile Phe Lys Ile Lys
            885             890             895
Thr Gln Asp Gly His Ala Arg Leu Gly Asn Leu Glu Phe Leu Glu Glu
            900             905             910
Lys Pro Leu Leu Gly Glu Ala Leu Ala Arg Val Lys Arg Ala Glu Lys
            915             920             925
Lys Trp Arg Asp Lys Arg Glu Thr Leu Gln Leu Glu Thr Thr Ile Val
            930             935             940
Tyr Lys Glu Ala Lys Glu Ser Val Asp Ala Leu Phe Val Asn Ser Gln
945             950             955             960
Tyr Asp Arg Leu Gln Ala Asp Thr Asn Ile Ala Met Ile His Ala Ala
            965             970             975
Asp Lys Arg Val His Arg Ile Arg Glu Ala Tyr Leu Pro Glu Leu Ser
            980             985             990
Val Ile Pro Gly Val Asn Ala Ala Ile Phe Glu Glu Leu Glu Glu Arg
            995             1000            1005
Ile Phe Thr Ala Phe Ser Leu Tyr Asp Ala Arg Asn Ile Ile Lys
            1010            1015            1020
Asn Gly Asp Phe Asn Asn Gly Leu Leu Cys Trp Asn Val Lys Gly
            1025            1030            1035
His Val Glu Val Glu Glu Gln Asn Asn His Arg Ser Val Leu Val
            1040            1045            1050
Ile Pro Glu Trp Glu Ala Glu Val Ser Gln Glu Val Arg Val Cys
            1055            1060            1065
Pro Gly Arg Gly Tyr Ile Leu Arg Val Thr Ala Tyr Lys Glu Gly
            1070            1075            1080
Tyr Gly Glu Gly Cys Val Thr Ile His Glu Ile Glu Asn Asn Thr
            1085            1090            1095
Asp Glu Leu Lys Phe Asn Asn Cys Val Glu Glu Glu Val Tyr Pro
            1100            1105            1110
```

| | | | | | | | | | | |
|---|---|---|---|---|---|---|---|---|---|---|
| Asn | Asn | Thr | Val | Thr | Cys | Ile | Asn | Tyr | Thr | Ala | Thr | Gln | Glu | Glu |
| | 1115 | | | | 1120 | | | | 1125 | |

| Tyr | Glu | Gly | Thr | Tyr | Thr | Ser | Arg | Asn | Arg | Gly | Tyr | Asp | Glu | Ala |
| | 1130 | | | | 1135 | | | | 1140 | |

| Tyr | Gly | Asn | Asn | Pro | Ser | Val | Pro | Ala | Asp | Tyr | Ala | Ser | Val | Tyr |
| | 1145 | | | | 1150 | | | | 1155 | |

| Glu | Glu | Lys | Ser | Tyr | Thr | Asp | Arg | Arg | Arg | Glu | Asn | Pro | Cys | Glu |
| | 1160 | | | | 1165 | | | | 1170 | |

| Ser | Asn | Arg | Gly | Tyr | Gly | Asp | Tyr | Thr | Pro | Leu | Pro | Ala | Gly | Tyr |
| | 1175 | | | | 1180 | | | | 1185 | |

| Val | Thr | Lys | Glu | Leu | Glu | Tyr | Phe | Pro | Glu | Thr | Asp | Lys | Val | Trp |
| | 1190 | | | | 1195 | | | | 1200 | |

| Ile | Glu | Ile | Gly | Glu | Thr | Glu | Gly | Thr | Phe | Ile | Val | Asp | Ser | Val |
| | 1205 | | | | 1210 | | | | 1215 | |

| Glu | Leu | Leu | Leu | Met | Glu | Glu |
| | 1220 | | | | 1225 | |

<210> SEQ ID NO 34
<211> LENGTH: 3726
<212> TYPE: DNA
<213> ORGANISM: Artificial
<220> FEATURE:
<223> OTHER INFORMATION: Recombinant nucleotide sequence used for
      expression in a bacterial cell encoding TIC868_11.

<400> SEQUENCE: 34

```
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca aacgggtatt     180
aacatagctg gtagaatact aggtgtatta ggcgtaccgt ttgctggaca aatagctagt     240
ttttatagtt ttcttgttgg tgaattatgg ccccgcggca gagatccttg ggaaattttc     300
ctagaacatg tcgaacaact tataagacaa caagtaacag aaaatactag ggatacggct     360
cttgctcgat tacaaggttt aggaaattcc tttagagcct atcaacagtc acttgaagat     420
tggctagaaa accgtgatga tgcaagaacg agaagtgttc tttataccca atatatagcc     480
ttagaacttg attttcttaa tgcgatgccg cttttcgcaa ttagaaacca agaagttcca     540
ttattaatgg tatatgctca agctgcaaat ttacacctat tattattgag agatgcctct     600
cttttttggta gtgaatttgg gcttacatcc caagaaattc aacgttatta tgagcgccaa     660
gtggaaaaaa cgagagaata ttctgattat tgcgcaagat ggtataatac gggtttaaat     720
aatttgagag ggacaaatgc tgaaagttgg ttgcgatata tcaattccg tagagactta     780
acgctaggag tattagatct agtggcacta ttcccaagct atgacacgcg tgtttatcca     840
atgaatacca gtgctcaatt aacaagagaa atttatacag atccaattgg gagaacaaat     900
gcaccttcag gatttgcaag tacgaattgg tttaataata atgcaccatc gttttctgcc     960
atagaggctg ccgttattag gcctccgcat ctacttgatt ttccagaaca gcttacaatt    1020
ttcagcgtat taagtcgatg gagtaatact caatatatga attactgggt gggacataga    1080
cttgaatcgc gaacaataag ggggtcatta agtacctcga cacacggaaa taccaatact    1140
tctattaatc ctgtaacatt acagttcaca tctcgagacg tttatagaac agaatcattt    1200
gcagggataa atatacttct aactactcct gtgaatggag taccttgggc tagatttaat    1260
tggagaaatc ccctgaattc tcttagaggt agccttctct atactatagg gtatactgga    1320
```

```
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta atcaaatacc tttagtgaaa ggatttagag tttgggggg cacctctgtc    1560 attacaggac caggatttac aggagggat atccttcgaa gaaatacctt tggtgatttt    1620
gtatctctac aagtcaatat taattcacca attacccaaa gataccgttt aagatttcgt    1680
tacgcttcca gtagggatgc acgagttata gtattaacag gagcggcatc cacaggagtg    1740
ggaggccaag ttagtgtaaa tatgcctctt cagaaaacta tggaaatagg ggagaactta    1800
acatctagaa catttagata taccgatttt agtaatcctt tttcatttag agctaatcca    1860
gatataattg ggataagtga acaacctcta tttggtgcag gttctattag tagcggtgaa    1920
ctttatatag ataaaattga aattattcta gcagatgcaa caggaacgac aacctatgag    1980
tatgaagaga agcagaatct agaaaaagcg cagaaagcgt tgaacgcttt gtttacggat    2040
ggcacgaatg gctatctaca aatggatgcc actgattatg atatcaatca aactgcaaac    2100
ttaatagaat gtgtatcaga tgaattgtat gcaaaagaaa agatagtttt attagatgaa    2160
gtcaaatatg cgaagcggct tagcatatca cgtaacctac ttttgaacga tgatttagaa    2220
ttttcagatg gatttggaga aaacggatgg acgacaagtg ataatatttc aatccaggcg    2280
gataatcccc ttttaaggg gaattattta aaaatgtttg gggcaagaga tattgatgga    2340
accctatttc caacttatct ctatcaaaaa atagatgagt ccaggttaaa accatataca    2400
cgttatcgag taagagggtt tgtgggaagt agtaaaaatc taaaattagt ggtaacacgc    2460
tatgagaaag aaattgatgc cattatgaat gttccaaatg atttggcaca tatgcagctt    2520
aacccttcat gtggagatta tcgctgtgaa tcatcgtccc agttttggt gaaccaagtg    2580 catcctacac caacagctgg atatgctctt gatatgtatg catgcccgtc aagttcagat    2640
aaaaaacata ttatgtgtca cgatcgtcat ccatttgatt tcatattga caccggagaa    2700 ttaaatccaa acacaaacct gggtattgat gtcttgttta aaatttctaa tccaaatgga    2760
tacgctacat tagggaatct agaagtcatt gaagaaggac cactaacaga tgaagcattg    2820
gtacatgtaa aacaaaagga aaagaaatgg cgtcagcaca tggagaaaaa acgaatggaa    2880
acacaacaag cctatgatcc agcaaaacaa gctgtagatg cattatttac aaatgaacaa    2940
gagttagact atcatactac tttagatcat attcagaacg ccgatcagct ggtacaggcg    3000
attccctatg tacaccatgc ttggttaccg gatgctccag gtatgaacta tgatgtatat    3060
caagggttaa acgcacgtat catgcaggcg tacaatttat atgatgcacg aaatgtcata    3120
ataaatggtg actttacaca aggactacaa ggatggcacg caacaggaaa agcagcggta    3180
caacaaatag atggagcttc agtattagtt ctatcaaact ggagtgccga ggtatctcag    3240
aatctgcatg cccaagatca tcatggatat atgttacgtg tgattgccaa aaagaaggt    3300 cctggaaaag ggtatgtaat gatgatggat tttaatggaa agcaggaaac acttacgttc    3360
acttcttgtg aagaaggata tataacaaaa acaatagagg tattcccgga aagtgatcga    3420
atacgaattg aaatgggaga acagagggt acgttttatg tagatagcat cgagttgctt    3480
tgtatgcaag gatatgctag cgataataac ccgcacacgg gtaatatgta tgagcaaagt    3540
tataatggaa attataatca aaatactagc gatgtgtatc accaaggata tataaacaac    3600
tataaccaaa attctagtag tatgtataat caaaattata ttaacaatga tgacctgcat    3660
```

-continued

| | |
|---|---|
| tccggttgca catgtaacca agggcataac tctggctgta catgtaatca aggatataac | 3720 |
| cgttag | 3726 |

<210> SEQ ID NO 35
<211> LENGTH: 3726
<212> TYPE: DNA
<213> ORGANISM: Artificial
<220> FEATURE:
<223> OTHER INFORMATION: Synthetic nucleotide sequence designed for
      expression in a plant cell encoding TIC868_11.

<400> SEQUENCE: 35

| | |
|---|---|
| atgacgagca accggaagaa cgagaacgag atcatcaacg ccctctcgat ccctgctgtt | 60 |
| tcaaaccact ccgcgcagat gaacctgtcc accgacgcgc catcgagga ctccctctgc | 120 |
| atagccgagg gcaacaacat cgacccattc gtgtcggcca gcacggttca gaccggcatc | 180 |
| aacatcgcgg gccgtatcct cggcgtcctc ggtgtcccat cgccggtca gatcgcgtcc | 240 |
| ttctactcgt tccttgtggg cgagctgtgg cctcgcggtc gtgacccgtg ggagatcttc | 300 |
| ctggagcatg tggagcagtt gatccggcag caagtcacgg agaacacccg cgatactgct | 360 |
| ctggccaggc tacagggcct gggaaaactcc tttcgggcat accagcagtc actggaggac | 420 |
| tggttggaga cagggatga cgcgcgaaca cgctcggtac tctacaccca gtacatcgct | 480 |
| ctcgaactcg acttcctgaa cgctatgccg ctgttcgcca tcaggaacca ggaagttcca | 540 |
| ctccttatgg tgtacgccca ggccgccaac ttacatctgc tcctgctgcg ggacgccagc | 600 |
| ctgttcggct ccgagttcgg actcacatct caagaaatcc agcgttacta cgagcgccaa | 660 |
| gtggagaaga cccgtgagta cagtgactac tgcgctcgat ggtacaacac agggctcaac | 720 |
| aacctgcgcg gcaccaacgc tgagtcatgg ctccgttaca accagttccg ccgcgacttg | 780 |
| actttgggtg tcctagacct ggtggcgcta ttcccgtctt acgacacacg ggtgtaccca | 840 |
| atgaacacta gcgcgcaact cacgcgggag atctacacag cccaatcgg ccggacgaac | 900 |
| gcaccctccg gtttcgcatc cacgaattgg ttcaacaaca acgcaccctc cttctcggca | 960 |
| atcgaggccg ccgtcatccg ccctcctcac ctgctcgact ttcccgagca gctcacgatc | 1020 |
| ttctccgtgc tctcacgctg gtccaacaca cagtacatga actactgggt cgggcaccga | 1080 |
| ttggagagta ggacgatccg tggcagcttg agcaccagta cccacggcaa caccaacacc | 1140 |
| tccatcaacc cagttacgct acagttcacg agccgcgacg tttaccggac tgagtcgttc | 1200 |
| gcgggcatta acatccttct gacaacgccc gtcaacggcg tcccgtgggc ccggttcaac | 1260 |
| tggcgtaacc cgttgaactc cctgcgcggg tcattgctct acaccatcgg gtacacgggc | 1320 |
| gtcggcaccc agctcttcga cagtgaaact gagctgccgc ccgagaccac ggaacgcccg | 1380 |
| aactacgagt cctacagcca ccgcctgtcc aacatccggc tcatctctgg caacacgctg | 1440 |
| cgtgcgccgg tgtactcctg gacacaccgc agcgccgacc ggaccaacac gatctcttcc | 1500 |
| gactccatta accagatccc gctcgtgaag ggcttccgtg tgtggggtgg cacgagcgtc | 1560 |
| atcaccggtc cgggcttcac cggtggagac atactgcggc gcaacacttt cggcgacttc | 1620 |
| gtttcgttgc aagtgaacat caactcgccg atcacccagc gttaccgtct gaggttccgc | 1680 |
| tacgcttcaa gccgcgacgc gagggtcatt gtcctgaccg gagccgcgtc cacaggcgtg | 1740 |
| ggaggccaag tctcagtcaa catgcctctc cagaagacga tggagatagg cgagaacttg | 1800 |
| actagccgaa cctccggta cactgatttc tcgaaccctt tctcattcag agcgaaccct | 1860 |
| gacatcattg ggatctccga gcaaccgctg ttcggtgctg gctccatcag gctctggcgaa | 1920 |

|  |  |  |  |  |
|---|---|---|---|---|
| ctgtacatcg | acaagattga | gatcatcctg | gcggatgcga | cggggactac cacctacgag | 1980 |
| tacgaggaga | agcagaatct | cgagaaggct | cagaaggctc | tgaacgctct gttcactgac | 2040 |
| gggaccaacg | gctacctcca | gatggacgcc | actgactacg | acatcaacca gacagctaac | 2100 |
| ctgattgagt | gtgtgagtga | cgaactgtac | gctaaggaga | gatcgtact cctggacgag | 2160 |
| gtgaagtacg | ctaagcgcct | gagcattagc | cgtaacctgc | tgctgaacga cgatctggag | 2220 |
| ttcagcgacg | gctttggcga | gaacggctgg | accaccagcg | acaacatctc catccaggcc | 2280 |
| gacaatccac | tcttcaaagg | caactacctc | aagatgttcg | agccaggga catcgacggc | 2340 |
| accctctttc | cgacctacct | ctaccagaag | atcgacgagt | cccgcctcaa acccctacacc | 2400 |
| cgctacaggg | tgcgcggctt | cgtgggcagc | agcaagaacc | tcaagctcgt ggtcacacgg | 2460 |
| tatgagaagg | agatcgacgc | catcatgaac | gtgcccaacg | atctcgccca catgcagctc | 2520 |
| aatccatcct | gcggcgacta | ccggtgcgag | tccagctccc | agttcctcgt gaaccaggtg | 2580 |
| caccctactc | cgaccgctgg | ctatgccctg | gacatgtacg | cctgccctag ttcctccgac | 2640 |
| aagaagcaca | tcatgtgcca | cgaccgtcat | ccgttcgact | ccacatcga caccggcgaa | 2700 |
| ctgaacccga | acaccaacct | gggcatcgac | gtactgttca | agatttccaa cccgaacggg | 2760 |
| tacgccacct | tgggcaacct | ggaggtcatc | gaagaaggcc | cgctgaccga cgaggccctg | 2820 |
| gtccacgtca | aacagaagga | gaagaagtgg | cggcagcaca | tggagaagaa gcggatggag | 2880 |
| actcaacaag | cctacgaccc | ggccaagcaa | gctgtggacg | ctctgttcac caacgagcaa | 2940 |
| gagcttgact | accacactac | tcttgaccac | atccagaatg | ctgaccagct tgtccaggct | 3000 |
| attccgtacg | tccaccacgc | ttggctaccg | gacgctccag | ggatgaacta cgatgtgtac | 3060 |
| cagggtctga | acgcgcggat | catgcaagcg | tacaacctgt | acgacgcgcg taacgtcatc | 3120 |
| atcaacggtg | acttcactca | gggtcttcaa | ggttggcacg | cgactggcaa agcggcagtc | 3180 |
| cagcagattg | atggtgcgtc | tgttcttgtg | ttgagcaact | ggtctgcgga ggtttctcag | 3240 |
| aacctgcacg | cacaggatca | ccacggctac | atgctgaggg | tgattgctaa gaaggagggc | 3300 |
| cctggcaaag | gctacgtcat | gatgatggac | ttcaacggaa | agcaagaaac cctgaccttc | 3360 |
| actagctgtg | aggagggcta | catcactaag | accattgagg | tctttccgga gtctgaccgc | 3420 |
| atccggatcg | agatgggcga | gaccgaaggc | acgttctacg | tggactccat cgaactcctc | 3480 |
| tgcatgcaag | gctacgcctc | cgacaacaac | ccacacacgg | gcaacatgta cgagcagtcc | 3540 |
| tacaacggga | actacaacca | gaacacctcc | gatgtgtacc | atcagggcta catcaacaac | 3600 |
| tacaaccaga | acagcagcag | catgtacaac | cagaactaca | tcaacaacga tgacttgcac | 3660 |
| tcgggttgca | cctgcaacca | gggtcacaac | agtgggtgca | cgtgcaacca gggatacaac | 3720 |
| cgttga |  |  |  |  | 3726 |

<210> SEQ ID NO 36
<211> LENGTH: 1241
<212> TYPE: PRT
<213> ORGANISM: Artificial
<220> FEATURE:
<223> OTHER INFORMATION: Amino acid sequence of the chimeric protein variant TIC868_11.

<400> SEQUENCE: 36

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

```
Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
 50                  55                  60

Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                 85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
```

```
            450                 455                 460
Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
                515                 520                 525

Gly Asp Ile Leu Arg Arg Asn Thr Phe Gly Asp Phe Val Ser Leu Gln
            530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
                595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Gly Thr
                645                 650                 655

Thr Thr Tyr Glu Tyr Glu Glu Lys Gln Asn Leu Glu Lys Ala Gln Lys
                660                 665                 670

Ala Leu Asn Ala Leu Phe Thr Asp Gly Thr Asn Gly Tyr Leu Gln Met
            675                 680                 685

Asp Ala Thr Asp Tyr Asp Ile Asn Gln Thr Ala Asn Leu Ile Glu Cys
            690                 695                 700

Val Ser Asp Glu Leu Tyr Ala Lys Glu Lys Ile Val Leu Leu Asp Glu
705                 710                 715                 720

Val Lys Tyr Ala Lys Arg Leu Ser Ile Ser Arg Asn Leu Leu Leu Asn
                725                 730                 735

Asp Asp Leu Glu Phe Ser Asp Gly Phe Gly Glu Asn Gly Trp Thr Thr
            740                 745                 750

Ser Asp Asn Ile Ser Ile Gln Ala Asp Asn Pro Leu Phe Lys Gly Asn
            755                 760                 765

Tyr Leu Lys Met Phe Gly Ala Arg Asp Ile Asp Gly Thr Leu Phe Pro
770                 775                 780

Thr Tyr Leu Tyr Gln Lys Ile Asp Glu Ser Arg Leu Lys Pro Tyr Thr
785                 790                 795                 800

Arg Tyr Arg Val Arg Gly Phe Val Gly Ser Ser Lys Asn Leu Lys Leu
                805                 810                 815

Val Val Thr Arg Tyr Glu Lys Glu Ile Asp Ala Ile Met Asn Val Pro
                820                 825                 830

Asn Asp Leu Ala His Met Gln Leu Asn Pro Ser Cys Gly Asp Tyr Arg
            835                 840                 845

Cys Glu Ser Ser Ser Gln Phe Leu Val Asn Gln Val His Pro Thr Pro
            850                 855                 860

Thr Ala Gly Tyr Ala Leu Asp Met Tyr Ala Cys Pro Ser Ser Ser Asp
865                 870                 875                 880
```

```
Lys Lys His Ile Met Cys His Asp Arg His Pro Phe Asp Phe His Ile
            885                 890                 895

Asp Thr Gly Glu Leu Asn Pro Asn Thr Asn Leu Gly Ile Asp Val Leu
        900                 905                 910

Phe Lys Ile Ser Asn Pro Asn Gly Tyr Ala Thr Leu Gly Asn Leu Glu
        915                 920                 925

Val Ile Glu Glu Gly Pro Leu Thr Asp Glu Ala Leu Val His Val Lys
930                 935                 940

Gln Lys Glu Lys Lys Trp Arg Gln His Met Glu Lys Lys Arg Met Glu
945                 950                 955                 960

Thr Gln Gln Ala Tyr Asp Pro Ala Lys Gln Ala Val Asp Ala Leu Phe
            965                 970                 975

Thr Asn Glu Gln Glu Leu Asp Tyr His Thr Thr Leu Asp His Ile Gln
        980                 985                 990

Asn Ala Asp Gln Leu Val Gln Ala Ile Pro Tyr Val His His Ala Trp
        995                 1000                1005

Leu Pro Asp Ala Pro Gly Met Asn Tyr Asp Val Tyr Gln Gly Leu
    1010                1015                1020

Asn Ala Arg Ile Met Gln Ala Tyr Asn Leu Tyr Asp Ala Arg Asn
    1025                1030                1035

Val Ile Ile Asn Gly Asp Phe Thr Gln Gly Leu Gln Gly Trp His
    1040                1045                1050

Ala Thr Gly Lys Ala Ala Val Gln Gln Ile Asp Gly Ala Ser Val
    1055                1060                1065

Leu Val Leu Ser Asn Trp Ser Ala Glu Val Ser Gln Asn Leu His
    1070                1075                1080

Ala Gln Asp His His Gly Tyr Met Leu Arg Val Ile Ala Lys Lys
    1085                1090                1095

Glu Gly Pro Gly Lys Gly Tyr Val Met Met Asp Phe Asn Gly
    1100                1105                1110

Lys Gln Glu Thr Leu Thr Phe Thr Ser Cys Glu Glu Gly Tyr Ile
    1115                1120                1125

Thr Lys Thr Ile Glu Val Phe Pro Glu Ser Asp Arg Ile Arg Ile
    1130                1135                1140

Glu Met Gly Glu Thr Glu Gly Thr Phe Tyr Val Asp Ser Ile Glu
    1145                1150                1155

Leu Leu Cys Met Gln Gly Tyr Ala Ser Asp Asn Asn Pro His Thr
    1160                1165                1170

Gly Asn Met Tyr Glu Gln Ser Tyr Asn Gly Asn Tyr Asn Gln Asn
    1175                1180                1185

Thr Ser Asp Val Tyr His Gln Gly Tyr Ile Asn Asn Tyr Asn Gln
    1190                1195                1200

Asn Ser Ser Ser Met Tyr Asn Gln Asn Tyr Ile Asn Asn Asp Asp
    1205                1210                1215

Leu His Ser Gly Cys Thr Cys Asn Gln Gly His Asn Ser Gly Cys
    1220                1225                1230

Thr Cys Asn Gln Gly Tyr Asn Arg
    1235                1240

<210> SEQ ID NO 37
<211> LENGTH: 3468
<212> TYPE: DNA
<213> ORGANISM: Artificial
<220> FEATURE:
```

<223> OTHER INFORMATION: Recombinant nucleotide sequence used for
      expression in a bacterial cell encoding TIC868_12.

<400> SEQUENCE: 37

| | | | | | |
|---|---|---|---|---|---|
| atgacttcaa | ataggaaaaa | tgagaatgaa | attataaatg | ctttatcgat | tccagctgta | 60 |
| tcgaatcatt | ccgcacaaat | gaatctatca | accgatgctc | gtattgagga | tagcttgtgt | 120 |
| atagccgagg | ggaacaatat | cgatccattt | gttagcgcat | caacagtcca | acgggtatt | 180 |
| aacatagctg | gtagaatact | aggtgtatta | ggcgtaccgt | tgctggaca | aatagctagt | 240 |
| ttttatagtt | ttcttgttgg | tgaattatgg | ccccgcggca | gagatccttg | ggaaattttc | 300 |
| ctagaacatg | tcgaacaact | tataagacaa | caagtaacag | aaaatactag | ggatacggct | 360 |
| cttgctcgat | tacaaggttt | aggaaattcc | tttagagcct | atcaacagtc | acttgaagat | 420 |
| tggctagaaa | accgtgatga | tgcaagaacg | agaagtgttc | tttatacccca | atatatagcc | 480 |
| ttagaacttg | attttcttaa | tgcgatgccg | cttttcgcaa | ttagaaacca | agaagttcca | 540 |
| ttattaatgg | tatatgctca | agctgcaaat | ttacacctat | tattattgag | agatgcctct | 600 |
| cttttttggta | gtgaatttgg | gcttacatcc | caagaaattc | aacgttatta | tgagcgccaa | 660 |
| gtggaaaaaa | cgagagaata | ttctgattat | tgcgcaagat | ggtataatac | gggtttaaat | 720 |
| aatttgagag | ggacaaatgc | tgaaagttgg | ttgcgatata | atcaattccg | tagagactta | 780 |
| acgctaggag | tattagatct | agtggcacta | ttcccaagct | atgacacgcg | tgtttatcca | 840 |
| atgaatacca | gtgctcaatt | aacaagagaa | atttatacag | atccaattgg | gagaacaaat | 900 |
| gcaccttcag | gatttgcaag | tacgaattgg | tttaataata | atgcaccatc | gtttctgcc | 960 |
| atagaggctg | ccgttattag | gcctccgcat | ctacttgatt | ttccagaaca | gcttacaatt | 1020 |
| ttcagcgtat | taagtcgatg | gagtaatact | caatatatga | attactgggt | gggacataga | 1080 |
| cttgaatcgc | gaacaataag | ggggtcatta | agtacctcga | cacacggaaa | taccaatact | 1140 |
| tctattaatc | ctgtaacatt | acagttcaca | tctcgagacg | tttatagaac | agaatcattt | 1200 |
| gcagggataa | atatacttct | aactactcct | gtgaatggag | taccttgggc | tagatttaat | 1260 |
| tggagaaatc | ccctgaattc | tcttagaggt | agccttctct | atactatagg | gtatactgga | 1320 |
| gtggggacac | aactatttga | ttcagaaact | gaattaccac | cagaaacaac | agaacgacca | 1380 |
| aattatgaat | cttacagtca | tagattatct | aatataagac | taatatcagg | aaacactttg | 1440 |
| agagcaccag | tatattcttg | gacgcaccgt | agtgcagatc | gtacaaatac | cattagttca | 1500 |
| gatagcatta | atcaaatacc | tttagtgaaa | ggatttagag | tttgggggggg | cacctctgtc | 1560 |
| attacaggac | caggatttac | aggagggat | atccttcgaa | gaaataccct | tggtgatttt | 1620 |
| gtatctctac | aagtcaatat | taattcacca | attacccaaa | gataccgttt | aagatttcgt | 1680 |
| tacgcttcca | gtagggatgc | acgagttata | gtattaacag | gagcggcatc | cacaggagtg | 1740 |
| ggaggccaag | ttagtgtaaa | tatgcctctt | cagaaaacta | tggaaatagg | ggagaactta | 1800 |
| acatctagaa | catttagata | taccgatttt | agtaatcctt | tttcatttag | agctaatcca | 1860 |
| gatataattg | ggataagtga | acaacctcta | tttggtgcag | gttctattag | tagcggtgaa | 1920 |
| ctttatatag | ataaaattga | aattattcta | gcagatgcaa | caaatccgac | gcgagaggcg | 1980 |
| gaagaggatc | tagaagcagc | gaagaaagcg | gtggcgagct | gtttacacg | tacaagggac | 2040 |
| ggattacaag | taaatgtgac | agattatcaa | gtcgatcaag | cggcaaattt | agtgtcatgc | 2100 |
| ttatcagatg | aacaatatgg | gcatgacaaa | agatgttat | tggaagcggt | aagagcggca | 2160 |
| aaacgcctca | gccgagaacg | caacttactt | caggatccag | attttaatac | aatcaatagt | 2220 |

| | |
|---|---:|
| acagaagaaa atggatggaa agcaagtaac ggcgttacta ttagcgaggg cggtccattc | 2280 |
| tataaaggcc gtgcgcttca gctagcaagc gcaagagaaa attacccaac atacattat | 2340 |
| caaaaagtaa atgcatcaga gttaaagccg tatacacgtt atagactgga tgggttcgtg | 2400 |
| aagagtagtc aagatttaga aattgatctc attcaccatc ataaagtcca tctcgtgaaa | 2460 |
| aatgtaccag ataatttagt atccgatact tactcggatg gttcttgcag tggaatgaat | 2520 |
| cgatgtgagg aacaacagat ggtaaatgcg caactggaaa cagaacatca tcatccgatg | 2580 |
| gattgctgtg aagcggctca aacacatgag ttttcttcct atattaatac aggcgatcta | 2640 |
| aattcaagtg tagatcaagg catttgggtt gtattgaaag ttcgaacaac cgatggttat | 2700 |
| gcgacgctag gaaatcttga attggtagag gtcggaccgt tatcgggtga atctctagaa | 2760 |
| cgtgaacaaa gggataatgc gaaatggagt gcagagctag gaagaaagcg tgcagaaaca | 2820 |
| gatcgcgtgt atcaagatgc caaacaatcc atcaatcatt tatttgtgga ttatcaagat | 2880 |
| caacaattaa atccagaaat agggatggca gatattattg acgctcaaaa tcttgtcgca | 2940 |
| tcaatttcag atgtgtatag cgatgcagta ctgcaaatcc tggaattaa ctatgagatt | 3000 |
| tacacagagc tatccaatcg cttacaacaa gcatcgtatc tgtatacgtc tcgaaatgcg | 3060 |
| gtgcaaaatg gggactttaa cagcggtcta gatagttgga atgcaacagg ggggctacg | 3120 |
| gtacaacagg atggcaatac gcatttctta gttctttctc attgggatgc acaagtttct | 3180 |
| caacaattta gagtgcagcc gaattgtaaa tatgtattac gtgtaacagc agagaaagta | 3240 |
| ggcggcggag acggatacgt gacaatccgg gatggtgctc atcatacaga aaagcttaca | 3300 |
| tttaatgcat gtgattatga tataaatggc acgtacgtga ctgataatac gtatctaaca | 3360 |
| aaagaagtgg tattctattc acatacagaa cacatgtggg tagaggtaag tgaaacagaa | 3420 |
| ggtgcatttc atatagatag tattgaattc gttgaaacag aaaagtag | 3468 |

<210> SEQ ID NO 38
<211> LENGTH: 3468
<212> TYPE: DNA
<213> ORGANISM: Artificial
<220> FEATURE:
<223> OTHER INFORMATION: Synthetic nucleotide sequence designed for
      expression in a plant cell encoding TIC868_12.

<400> SEQUENCE: 38

| | |
|---|---:|
| atgacgagca accggaagaa cgagaacgag atcatcaacg ccctctcgat ccctgctgtt | 60 |
| tcaaaccact ccgcgcagat gaacctgtcc accgacgcgc gcatcgagga ctccctctgc | 120 |
| atagccgagg caacaacat cgacccattc gtgtcggcca gcacggttca gaccggcatc | 180 |
| aacatcgcgg gccgtatcct cggcgtcctc ggtgtcccat cgccggtca gatcgcgtcc | 240 |
| ttctactcgt tccttgtggg cgagctgtgg cctcgcggtc gtgacccgtg ggagatcttc | 300 |
| ctggagcatg tggagcagtt gatccggcag caagtcacgg agaacacccg cgatactgct | 360 |
| ctggccaggc tacagggcct gggaaactcc tttcgggcat accagcagtc actggaggac | 420 |
| tggttggaga acagggatga cgcgcgaaca cgctcggtac tctacaccca gtacatcgct | 480 |
| ctcgaactcg acttcctgaa cgctatgccg ctgttcgcca tcaggaacca ggaagttcca | 540 |
| ctccttatgg tgtacgccca ggccgccaac ttacatctgc tcctgctgcg ggacgccagc | 600 |
| ctgttcggct ccgagttcgg actcacatct caagaaatcc agcgttacta cgagcgccaa | 660 |
| gtggagaaga cccgtgagta cagtgactac tgcgctcgat ggtacaacac agggctcaac | 720 |
| aacctgcgcg gcaccaacgc tgagtcatgg ctccgttaca ccagttccg ccgcgacttg | 780 |

```
actttgggtg tcctagacct ggtggcgcta ttcccgtctt acgacacacg ggtgtaccca      840
atgaacacta gcgcgcaact cacgcgggag atctacacag acccaatcgg ccggacgaac      900
gcaccctccg gtttcgcatc cacgaattgg ttcaacaaca acgcaccctc cttctcggca      960
atcgaggccg ccgtcatccg ccctcctcac ctgctcgact ttcccgagca gctcacgatc     1020
ttctccgtgc tctcacgctg gtccaacaca cagtacatga actactgggt cgggcaccga     1080
ttggagagta ggacgatccg tggcagcttg agcaccagta cccacggcaa caccaacacc     1140
tccatcaacc cagttacgct acagttcacg agccgcgacg tttaccggac tgagtcgttc     1200
gcgggcatta acatccttct gacaacgccc gtcaacggcg tcccgtgggc ccggttcaac     1260
tggcgtaacc cgttgaactc cctgcgcggg tcattgctct acaccatcgg gtacacgggc     1320
gtcggcaccc agctcttcga cagtgaaact gagctgccgc ccgagaccac ggaacgcccg     1380
aactacgagt cctacagcca ccgcctgtcc aacatccggc tcatctctgg caacacgctg     1440
cgtgcgccgg tgtactcctg gacacaccgc agcgccgacc ggaccaacac gatctcttcc     1500
gactccatta accagatccc gctcgtgaag ggcttccgtg tgtggggtgg cacgagcgtc     1560
atcaccggtc cgggcttcac cggtggagac atactgcggc gcaacacttt cggcgacttc     1620
gtttcgttgc aagtgaacat caactcgccg atcccccagc gttaccgtct gaggttccgc     1680
tacgcttcaa gccgcgacgc gagggtcatt gtcctgaccg gagccgcgtc cacaggcgtg     1740
ggaggccaag tctcagtcaa catgcctctc cagaagacga tggagatagg cgagaacttg     1800
actagccgaa ccttccggta cactgatttc tcgaacccct tctcattcag agcgaaccct     1860
gacatcattg ggatctccga gcaaccgctg ttcggtgctg gctccatcag ctctggcgaa     1920
ctgtacatcg acaagattga gatcatcctg gcggatgcga cgaacccgac gcgggaagct     1980
gaggaagact tggaagccgc caagaaagcg gtcgccagcc tgtttactcg gacgcgggac     2040
gggctccaag tgaatgtgac ggactatcaa gtggatcagg ccgctaacct cgtgtcatgc     2100
ctgagcgacg agcagtacgg tcacgacaag aaaatgctgc tggaggccgt ccgggccgcc     2160
aagcggctgt ccagggagcg taacctgcta caagatcccg actttaacac gatcaacagc     2220
acagaggaga atggctggaa ggccagcaac ggagttacga taagcgaggg cggtccgttc     2280
tacaagggtc gtgccctcca gctcgcctct gcaagggaga actatccaac ctacatctat     2340
cagaaggtga acgcatccga gcttaagccc tacacacgct accgcctgga cgggttcgtt     2400
aagtccagtc aagacctaga gatagacctc atccaccacc acaaagtgca tctggtcaag     2460
aacgttcccg ataatctcgt gagcgatacc tactcagacg gctcatgctc tggcatgaac     2520
agatgtgagg agcaacagat ggttaatgct caactcgaaa ccgagcatca tcatcctatg     2580
gattgctgcg aggccgcgca gacccatgag ttcagctctt acatcaacac cggagacctc     2640
aacagtagcg tggatcaggg aatttgggtg gtgcttaaag tgcgtacaac cgacggctac     2700
gccaccctcg gcaaccttga gcttgtcgag gtcggaccac ttagcggcga gtccctggaa     2760
cgtgagcagc gggacaacgc caaatggagc gcagagctag ggcgcaaacg cgcggagacg     2820
gaccgggttt atcaggacgc gaagcagtcc atcaatcacc tcttcgtgga ttatcaggac     2880
cagcagctta atccagagat cggcatggcc gacatcatcg acgcccagaa cctagtagcg     2940
tcgatttccg atgtctattc cgacgccgtg cttcaaatac ctggcatcaa ctacgagatc     3000
tacacagagt tgtccaacag gctccagcaa gcgtcatacc tctacaccag ccgcaacgcc     3060
gtccagaatg gcgacttcaa ttccggacta gactcctgga acgccacggg cggagctacg     3120
gtgcaacaag acggcaacac ccacttcctc gtacttagcc actgggacgc tcaagtgagt     3180
```

```
cagcaattcc gggttcagcc gaactgcaag tacgtcctgc gcgtaacggc cgagaaggtt    3240
ggaggcggag acggctacgt taccatccgc gacggcgctc accacaccga gaaactgacg    3300
ttcaacgctt gtgactacga catcaacggc acttacgtga cggacaacac ctacctgacg    3360
aaggaggtgg tgttctattc tcacaccgag cacatgtggg ttgaggtcag cgagaccgag    3420
ggagccttcc acattgacag catcgagttc gtggagactg agaagtga               3468
```

<210> SEQ ID NO 39
<211> LENGTH: 1155
<212> TYPE: PRT
<213> ORGANISM: Artificial
<220> FEATURE:
<223> OTHER INFORMATION: Amino acid sequence of the chimeric protein variant TIC868_12.

<400> SEQUENCE: 39

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300
```

```
Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
                500                 505                 510

Arg Val Trp Gly Gly Thr Ser Val Ile Thr Gly Pro Gly Phe Thr Gly
                515                 520                 525

Gly Asp Ile Leu Arg Arg Asn Thr Phe Gly Asp Phe Val Ser Leu Gln
                530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
                580                 585                 590

Thr Met Glu Ile Gly Glu Asn Leu Thr Ser Arg Thr Phe Arg Tyr Thr
                595                 600                 605

Asp Phe Ser Asn Pro Phe Ser Phe Arg Ala Asn Pro Asp Ile Ile Gly
                610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asn Pro
                645                 650                 655

Thr Arg Glu Ala Glu Glu Asp Leu Glu Ala Ala Lys Lys Ala Val Ala
                660                 665                 670

Ser Leu Phe Thr Arg Thr Arg Asp Gly Leu Gln Val Asn Val Thr Asp
                675                 680                 685

Tyr Gln Val Asp Gln Ala Ala Asn Leu Val Ser Cys Leu Ser Asp Glu
                690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
```

```
                        725                 730                 735
Thr Ile Asn Ser Thr Glu Glu Asn Gly Trp Lys Ala Ser Asn Gly Val
                    740                 745                 750

Thr Ile Ser Glu Gly Gly Pro Phe Tyr Lys Gly Arg Ala Leu Gln Leu
                    755                 760                 765

Ala Ser Ala Arg Glu Asn Tyr Pro Thr Tyr Ile Tyr Gln Lys Val Asn
                    770                 775                 780

Ala Ser Glu Leu Lys Pro Tyr Thr Arg Tyr Arg Leu Asp Gly Phe Val
785                 790                 795                 800

Lys Ser Ser Gln Asp Leu Glu Ile Asp Leu Ile His His Lys Val
                    805                 810                 815

His Leu Val Lys Asn Val Pro Asp Asn Leu Val Ser Asp Thr Tyr Ser
                    820                 825                 830

Asp Gly Ser Cys Ser Gly Met Asn Arg Cys Glu Glu Gln Met Val
                    835                 840                 845

Asn Ala Gln Leu Glu Thr Glu His His His Pro Met Asp Cys Cys Glu
850                 855                 860

Ala Ala Gln Thr His Glu Phe Ser Ser Tyr Ile Asn Thr Gly Asp Leu
865                 870                 875                 880

Asn Ser Ser Val Asp Gln Gly Ile Trp Val Val Leu Lys Val Arg Thr
                    885                 890                 895

Thr Asp Gly Tyr Ala Thr Leu Gly Asn Leu Glu Leu Val Glu Val Gly
                    900                 905                 910

Pro Leu Ser Gly Glu Ser Leu Glu Arg Glu Gln Arg Asp Asn Ala Lys
                    915                 920                 925

Trp Ser Ala Glu Leu Gly Arg Lys Arg Ala Glu Thr Asp Arg Val Tyr
                    930                 935                 940

Gln Asp Ala Lys Gln Ser Ile Asn His Leu Phe Val Asp Tyr Gln Asp
945                 950                 955                 960

Gln Gln Leu Asn Pro Glu Ile Gly Met Ala Asp Ile Ile Asp Ala Gln
                    965                 970                 975

Asn Leu Val Ala Ser Ile Ser Asp Val Tyr Ser Asp Ala Val Leu Gln
                    980                 985                 990

Ile Pro Gly Ile Asn Tyr Glu Ile  Tyr Thr Glu Leu Ser  Asn Arg Leu
                    995                 1000                1005

Gln Gln  Ala Ser Tyr Leu Tyr  Thr Ser Arg Asn Ala  Val Gln Asn
         1010                 1015                1020

Gly Asp  Phe Asn Ser Gly Leu  Asp Ser Trp Asn Ala  Thr Gly Gly
         1025                 1030                1035

Ala Thr  Val Gln Gln Asp Gly  Asn Thr His Phe Leu  Val Leu Ser
         1040                 1045                1050

His Trp  Asp Ala Gln Val Ser  Gln Gln Phe Arg Val  Gln Pro Asn
         1055                 1060                1065

Cys Lys  Tyr Val Leu Arg Val  Thr Ala Glu Lys Val  Gly Gly Gly
         1070                 1075                1080

Asp Gly  Tyr Val Thr Ile Arg  Asp Gly Ala His His  Thr Glu Lys
         1085                 1090                1095

Leu Thr  Phe Asn Ala Cys Asp  Tyr Asp Ile Asn Gly  Thr Tyr Val
         1100                 1105                1110

Thr Asp  Asn Thr Tyr Leu Thr  Lys Glu Val Val Phe  Tyr Ser His
         1115                 1120                1125

Thr Glu  His Met Trp Val Glu  Val Ser Glu Thr Glu  Gly Ala Phe
         1130                 1135                1140
```

His Ile Asp Ser Ile Glu Phe Val Glu Thr Glu Lys
    1145                1150               1155

<210> SEQ ID NO 40
<211> LENGTH: 3732
<212> TYPE: DNA
<213> ORGANISM: Artificial
<220> FEATURE:
<223> OTHER INFORMATION: Synthetic nucleotide sequence designed for
      expression in a plant cell encoding TIC868_13.

<400> SEQUENCE: 40

| | | | | |
|---|---|---|---|---|
| atgacgagca | accggaagaa | cgagaacgag | atcatcaacg | ccctctcgat | ccctgctgtt | 60 |
| tcaaaccact | ccgcgcagat | gaacctgtcc | accgacgcgc | gcatcgagga | ctccctctgc | 120 |
| atagccgagg | gcaacaacat | cgacccattc | gtgtcggcca | gcacggttca | gaccggcatc | 180 |
| aacatcgcgg | gccgtatcct | cggcgtcctc | ggtgtcccat | cgccggtca | gatcgcgtcc | 240 |
| ttctactcgt | tccttgtggg | cgagctgtgg | cctcgcggtc | gtgacccgtg | ggagatcttc | 300 |
| ctggagcatg | tggagcagtt | gatccggcag | caagtcacgg | agaacacccg | cgatactgct | 360 |
| ctggccaggc | tacagggcct | gggaaaactcc | tttcgggcat | accagcagtc | actggaggac | 420 |
| tggttggaga | cagggatga | cgcgcgaaca | cgctcggtac | tctacaccca | gtacatcgct | 480 |
| ctcgaactcg | acttcctgaa | cgctatgccg | ctgttcgcca | tcaggaacca | ggaagttcca | 540 |
| ctccttatgg | tgtacgccca | ggccgccaac | ttacatctgc | tcctgctgcg | ggacgccagc | 600 |
| ctgttcggct | ccgagttcgg | actcacatct | caagaaatcc | agcgttacta | cgagcgccaa | 660 |
| gtggagaaga | cccgtgagta | cagtgactac | tgcgctcgat | ggtacaacac | agggctcaac | 720 |
| aacctgcgcg | gcaccaacgc | tgagtcatgg | ctccgttaca | accagttccg | ccgcgacttg | 780 |
| actttgggtg | tcctagacct | ggtggcgcta | ttcccgtctt | acgacacacg | ggtgtaccca | 840 |
| atgaacacta | gcgcgcaact | cacgcgggag | atctacacag | acccaatcgg | ccggacgaac | 900 |
| gcaccctccg | gtttcgcatc | cacgaattgg | ttcaacaaca | acgcaccctc | cttctcggca | 960 |
| atcgaggccg | ccgtcatccg | ccctcctcac | ctgctcgact | ttcccgagca | gctcacgatc | 1020 |
| ttctccgtgc | tctcacgctg | gtccaacaca | cagtacatga | actactgggt | cgggcaccga | 1080 |
| ttggagagta | ggacgatccg | tggcagcttg | agcaccagta | cccacggcaa | caccaacacc | 1140 |
| tccatcaacc | cagttacgct | acagttcacg | agccgcgacg | tttaccggac | tgagtcgttc | 1200 |
| gcgggcatta | acatccttct | gacaacgccc | gtcaacggcg | tcccgtgggc | ccggttcaac | 1260 |
| tggcgtaacc | cgttgaactc | cctgcgcggg | tcattgctct | acaccatcgg | gtacacgggc | 1320 |
| gtcggcaccc | agctcttcga | cagtgaaact | gagctgccgc | ccgagaccac | ggaacgcccg | 1380 |
| aactacgagt | cctacagcca | ccgcctgtcc | aacatccggc | tcatctctgg | caacacgctg | 1440 |
| cgtgcgccgg | tgtactcctg | gacacaccgc | agcgccgacc | ggaccaacac | gatctcttcc | 1500 |
| gactccatta | accagatccc | gctcgtgaag | ggcttccgtg | tgtggggtgg | cacgagcgtc | 1560 |
| atcaccggtc | cgggcttcac | cggtggagac | atactgcggc | gcaacacttt | cggcgacttc | 1620 |
| gtttcgttgc | aagtgaacat | caactcgccg | atcacccagc | gttaccgtct | gaggttccgc | 1680 |
| tacgcttcaa | gccgcgacgc | gagggtcatt | gtcctgaccg | gagccgcgtc | cacaggcgtg | 1740 |
| ggaggccaag | tctcagtcaa | catgcctctc | cagaagacga | tggagatagg | cgagaacttg | 1800 |
| actagccgaa | ccttccggta | cactgatttc | tcgaacccctt | tctcattcag | agcgaaccct | 1860 |
| gacatcattg | ggatctccga | gcaaccgctg | ttcggtgctg | gctccatcag | ctctggcgaa | 1920 |

```
ctgtacatcg acaagattga gatcatcctg gcggatgcga cgacggcgac cttcgaggcg    1980
gagtatgact ggagcgggc tcaggaggcc gtcaacgcgc tgttcacaaa caccaatcct    2040
cgccgcctca agacgggtgt gactgattac cacattgacg aggtctccaa cttggtcgcg    2100
tgtctgtccg atgagttctg cctggacgag aagcgggaac tgctggagaa ggtcaagtac    2160
gccaagcgcc tctccgacga aggaacctc ctccaagatc ccaactttac ttccattaac    2220
aagcagccgg acttcatctc caccaacgag cagtccaact tcacctcaat ccacgagcag    2280
tcggagcacg ggtggtgggg cagcgagaac atcaccatcc aagagggcaa cgacgtcttc    2340
aaggagaact acgtgatcct gcccggcacc ttcaacgagt gttacccgac ctatctctac    2400
cagaagattg gcgaagcgga actcaaggct tacacccgtt accaactgag tggctacatt    2460
gaggactcac aagacctgga aatctacctg atccgctaca cgccaagca cgagaccctc    2520
gacgtgcctg gcacggagtc cgtctggccc ttgagcgtgg agtctcctat cggtcgttgc    2580
ggcgagccca tcgctgcgc tccgcacttt gagtggaatc ctgatttgga ttgctccctgc    2640
cgagacggtg agaaatgcgc ccaccactcg caccacttca gcctagacat cgacgtgggc    2700
tgcatcgacc tgcacgagaa cttgggcgtc tgggtcgtgt tcaagatcaa gacacaggag    2760
ggccatgctc ggcttgggaa cctggagttc atcgaggaga agccactgct gggtgaagcc    2820
ttgtcacggg tgaaacgcgc cgagaagaag tggcgggaca aacgggagaa gctccagttg    2880
gagacaaagc gtgtgtacac agaggccaag gaggccgtgg atgccttgtt cgtggacagt    2940
cagtacgaca ggctgcaagc ggacaccaac atcgggatga ccacgcggc tgataagctt    3000
gttcacagaa tccgcgaggc gtacctgtca gagcttagcg tgatcccagg cgtcaacgcc    3060
gaaatcttcg aggaactgga gggccgcatt atcacggcaa tctcacttta tgacgcgagg    3120
aatgtggtca gaacggtga cttcaacaac ggcttggcgt gttggaacgt taaagggcac    3180
gtggatgtac aacagtcaca ccacagaagt gtcttggtca tcccggagtg ggaggcggaa    3240
gtgagccagg ccgtccgggt ctgccctggg cgcggttaca tcctccgcgt gacagcgtac    3300
aaggagggct acggtgaggg ctgcgtgacg atccacgaga ttgagaacaa cacggacgag    3360
cttaagttca agaactgcga ggaggaggaa gtgtacccga cagacaccgg cacctgcaac    3420
gactacaccg cccaccaagg gaccgccgcc tgcaacagcc gcaacgcggg ctatgaagat    3480
gcgtacgagt tgataccac cgcctcagtg aactacaaac cgacttatga ggaggagaca    3540
tacacggacg tcaggcgcga caaccattgt gagtacgacc gtggctacgt gaactatccg    3600
ccggtgccag cgggctacat gacgaaggag ctagaatact ccctgagac ggacaaggtg    3660
tggattgaaa tcggcgagac cgagggcaag tttatcgtgg attctgtcga gctgctgcta    3720
atggaggagt ag                                                        3732
```

<210> SEQ ID NO 41
<211> LENGTH: 1243
<212> TYPE: PRT
<213> ORGANISM: Artificial
<220> FEATURE:
<223> OTHER INFORMATION: Amino acid sequence of the chimeric protein variant TIC868_13.

<400> SEQUENCE: 41

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30
```

```
Ala Arg Ile Glu Asp Ser Leu Cys Ile Ala Glu Gly Asn Asn Ile Asp
         35                  40                  45

Pro Phe Val Ser Ala Ser Thr Val Gln Thr Gly Ile Asn Ile Ala Gly
 50                  55                  60

Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                 85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
```

```
            450                 455                 460
Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
            515                 520                 525

Gly Asp Ile Leu Arg Arg Asn Thr Phe Gly Asp Phe Val Ser Leu Gln
            530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
            595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Thr Ala
                645                 650                 655

Thr Phe Glu Ala Glu Tyr Asp Leu Glu Arg Ala Gln Glu Ala Val Asn
            660                 665                 670

Ala Leu Phe Thr Asn Thr Asn Pro Arg Arg Leu Lys Thr Gly Val Thr
            675                 680                 685

Asp Tyr His Ile Asp Glu Val Ser Asn Leu Val Ala Cys Leu Ser Asp
            690                 695                 700

Glu Phe Cys Leu Asp Glu Lys Arg Glu Leu Leu Glu Lys Val Lys Tyr
705                 710                 715                 720

Ala Lys Arg Leu Ser Asp Glu Arg Asn Leu Leu Gln Asp Pro Asn Phe
                725                 730                 735

Thr Ser Ile Asn Lys Gln Pro Asp Phe Ile Ser Thr Asn Glu Gln Ser
            740                 745                 750

Asn Phe Thr Ser Ile His Glu Gln Ser Glu His Gly Trp Trp Gly Ser
            755                 760                 765

Glu Asn Ile Thr Ile Gln Glu Gly Asn Asp Val Phe Lys Glu Asn Tyr
            770                 775                 780

Val Ile Leu Pro Gly Thr Phe Asn Glu Cys Tyr Pro Thr Tyr Leu Tyr
785                 790                 795                 800

Gln Lys Ile Gly Glu Ala Glu Leu Lys Ala Tyr Thr Arg Tyr Gln Leu
                805                 810                 815

Ser Gly Tyr Ile Glu Asp Ser Gln Asp Leu Glu Ile Tyr Leu Ile Arg
            820                 825                 830

Tyr Asn Ala Lys His Glu Thr Leu Asp Val Pro Gly Thr Glu Ser Val
            835                 840                 845

Trp Pro Leu Ser Val Glu Ser Pro Ile Gly Arg Cys Gly Glu Pro Asn
            850                 855                 860

Arg Cys Ala Pro His Phe Glu Trp Asn Pro Asp Leu Asp Cys Ser Cys
865                 870                 875                 880
```

```
Arg Asp Gly Glu Lys Cys Ala His His Ser His His Phe Ser Leu Asp
            885                 890                 895
Ile Asp Val Gly Cys Ile Asp Leu His Glu Asn Leu Gly Val Trp Val
            900                 905                 910
Val Phe Lys Ile Lys Thr Gln Glu Gly His Ala Arg Leu Gly Asn Leu
            915                 920                 925
Glu Phe Ile Glu Glu Lys Pro Leu Leu Gly Glu Ala Leu Ser Arg Val
            930                 935                 940
Lys Arg Ala Glu Lys Lys Trp Arg Asp Lys Arg Glu Lys Leu Gln Leu
945                 950                 955                 960
Glu Thr Lys Arg Val Tyr Thr Glu Ala Lys Glu Ala Val Asp Ala Leu
            965                 970                 975
Phe Val Asp Ser Gln Tyr Asp Arg Leu Gln Ala Asp Thr Asn Ile Gly
            980                 985                 990
Met Ile His Ala Ala Asp Lys Leu Val His Arg Ile Arg Glu Ala Tyr
            995                 1000                1005
Leu Ser Glu Leu Ser Val Ile Pro Gly Val Asn Ala Glu Ile Phe
            1010                1015                1020
Glu Glu Leu Glu Gly Arg Ile Ile Thr Ala Ile Ser Leu Tyr Asp
            1025                1030                1035
Ala Arg Asn Val Val Lys Asn Gly Asp Phe Asn Asn Gly Leu Ala
            1040                1045                1050
Cys Trp Asn Val Lys Gly His Val Asp Val Gln Gln Ser His His
            1055                1060                1065
Arg Ser Val Leu Val Ile Pro Glu Trp Glu Ala Glu Val Ser Gln
            1070                1075                1080
Ala Val Arg Val Cys Pro Gly Arg Gly Tyr Ile Leu Arg Val Thr
            1085                1090                1095
Ala Tyr Lys Glu Gly Tyr Gly Glu Gly Cys Val Thr Ile His Glu
            1100                1105                1110
Ile Glu Asn Asn Thr Asp Glu Leu Lys Phe Lys Asn Cys Glu Glu
            1115                1120                1125
Glu Glu Val Tyr Pro Thr Asp Thr Gly Thr Cys Asn Asp Tyr Thr
            1130                1135                1140
Ala His Gln Gly Thr Ala Ala Cys Asn Ser Arg Asn Ala Gly Tyr
            1145                1150                1155
Glu Asp Ala Tyr Glu Val Asp Thr Thr Ala Ser Val Asn Tyr Lys
            1160                1165                1170
Pro Thr Tyr Glu Glu Glu Thr Tyr Thr Asp Val Arg Arg Asp Asn
            1175                1180                1185
His Cys Glu Tyr Asp Arg Gly Tyr Val Asn Tyr Pro Pro Val Pro
            1190                1195                1200
Ala Gly Tyr Met Thr Lys Glu Leu Glu Tyr Phe Pro Glu Thr Asp
            1205                1210                1215
Lys Val Trp Ile Glu Ile Gly Glu Thr Glu Gly Lys Phe Ile Val
            1220                1225                1230
Asp Ser Val Glu Leu Leu Leu Met Glu Glu
            1235                1240

<210> SEQ ID NO 42
<211> LENGTH: 3702
<212> TYPE: DNA
<213> ORGANISM: Artificial
<220> FEATURE:
```

<223> OTHER INFORMATION: Synthetic nucleotide sequence designed for
expression in a plant cell encoding TIC868_14.

<400> SEQUENCE: 42

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg caacaacat cgacccattc gtgtcggcca gcacggttca gaccggcatc      180
aacatcgcgg gccgtatcct cggcgtcctc ggtgtcccat cgccggtca gatcgcgtcc      240
ttctactcgt tccttgtggg cgagctgtgg cctcgcggtc gtgacccgtg ggagatcttc     300
ctggagcatg tggagcagtt gatccggcag caagtcacgg agaacacccg cgatactgct     360
ctggccaggc tacagggcct gggaaactcc tttcgggcat accagcagtc actggaggac     420
tggttggaga cagggatga cgcgcgaaca cgctcggtac tctacaccca gtacatcgct     480
ctcgaactcg acttcctgaa cgctatgccg ctgttcgcca tcaggaacca ggaagttcca     540
ctccttatgg tgtacgccca ggccgccaac ttacatctgc tcctgctgcg ggacgccagc     600
ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag acccaatcgg ccggacgaac     900
gcaccctccg gtttcgcatc cacgaattgg ttcaacaaca acgcaccctc cttctcggca     960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa cctccggta cactgatttc tcgaaccctt tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgaccgcgac gtttgaagct    1980
gaatccgacc tcgagcgtgc gcgcaaggcg gtgaacgctc tgttcacgag caccaaccct    2040
cgtggcttga agacggatgt gacggactac cacatcgacc aagtctcgaa cctcgtggag    2100
tgcctgagcg acgagttctg tcttgacaag aagcgcgagc tgctggagga ggtgaagtac    2160
gccaagcgcc tctccgatga gcgcaacctg ctccaagatc ctaccttcac gtcgatttcc    2220
```

```
ggccaaaccg accgtggatg gatcggctcg actggcatct ccatccaggg cggcgacgac    2280
atcttcaagg agaactatgt tcggctgccg ggcacggtgg acgagtgtta cccgacgtac    2340
ctctaccaga agatagacga gagtcaactc aagtcctaca cgcggtatca gttacgtggc    2400
tacattgaag actcccagga cttggaaatc tatctcatac ggtacaacgc caagcacgag    2460
accttaagcg tgccgggaac ggagtcgccc tggccaagct ctggcgtgta cccttccggt    2520
aggtgcggcg agcccaaccg ctgtgcacct cgaatcgaat ggaacccgga ccttgactgc    2580
tcttgccggt acggcgagaa gtgcgtccat cattctcacc acttcagctt ggacattgac    2640
gtcggctgca ccgacctcaa tgaagacctc ggagtgtggg tcatcttcaa gatcaagaca    2700
caggacgggc acgcgaaact aggaaacctg gagttcatcg aggagaagcc actcctcggc    2760
aaggcacttt ccagggtcaa gcgggccgag aagaaatgga gggacaagta cgagaaactc    2820
cagctcgaaa caaagcgggt gtacacggag gcaaaggaat ccgtggacgc cctgttcgtg    2880
gactctcagt acgacaagct ccaggcgaac acaaacattg gcatcatcca cggtgcggac    2940
aagcaagtgc acaggatacg ggagccttac ctctcggagc tgccggtgat tccctcgatc    3000
aacgcggcga tcttcgagga actggagggc cacatcttca aggcgtattc tctgtacgac    3060
gcgcgtaacg tcatcaagaa cggcgacttc aacaatgggc tgtcctgctg gaacgttaaa    3120
ggccacgtcg atgtccagca gaaccaccat aggtcagtcc tggtgctgag cgagtgggag    3180
gcggaggtgt cccagaaggt gcgcgtgtgc ccggatcgcg gctacatctt gagggtgaca    3240
gcctacaagg agggctacgg cgagggctgt gtcacgatcc atgagttcga ggacaacacg    3300
gatgtcctga aattccgtaa cttcgtcgag gaggaggtct atcccaacaa caccgtgacc    3360
tgcaacgact acacgaccaa tcagtcggct gagggcagta ccgatgcctg caacagctac    3420
aaccgtggtt acgaagatgg atacgagaac cgctacgagc ccaatccttc ggctcccgtg    3480
aattacactc ccacgtacga ggagggcatg tacactgaca ctcagggcta caaccattgc    3540
gtcagcgacc gtggctaccg caaccacacg ccgctcccag cgggctacgt gacgctggag    3600
ctggaatact ttcccgagac agaacaagtg tggatagaga tcggcgagac cgagggcaca    3660
ttcatcgtgg gctctgtgga attgctcctc atggaggagt aa                      3702
```

<210> SEQ ID NO 43
<211> LENGTH: 1200
<212> TYPE: PRT
<213> ORGANISM: Artificial
<220> FEATURE:
<223> OTHER INFORMATION: Amino acid sequence of the chimeric protein
      variant TIC868_14.

<400> SEQUENCE: 43

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95
```

-continued

```
Trp Glu Ile Phe Leu Glu His Val Glu Gln Leu Ile Arg Gln Gln Val
            100                 105                 110
Thr Glu Asn Thr Arg Asp Thr Ala Leu Ala Arg Leu Gln Gly Leu Gly
        115                 120                 125
Asn Ser Phe Arg Ala Tyr Gln Gln Ser Leu Glu Asp Trp Leu Glu Asn
    130                 135                 140
Arg Asp Asp Ala Arg Thr Arg Ser Val Leu Tyr Thr Gln Tyr Ile Ala
145                 150                 155                 160
Leu Glu Leu Asp Phe Leu Asn Ala Met Pro Leu Phe Ala Ile Arg Asn
                165                 170                 175
Gln Glu Val Pro Leu Leu Met Val Tyr Ala Gln Ala Ala Asn Leu His
            180                 185                 190
Leu Leu Leu Leu Arg Asp Ala Ser Leu Phe Gly Ser Glu Phe Gly Leu
        195                 200                 205
Thr Ser Gln Glu Ile Gln Arg Tyr Tyr Glu Arg Gln Val Glu Lys Thr
    210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
            260                 265                 270
Ser Tyr Asp Thr Arg Val Tyr Pro Met Asn Thr Ser Ala Gln Leu Thr
        275                 280                 285
Arg Glu Ile Tyr Thr Asp Pro Ile Gly Arg Thr Asn Ala Pro Ser Gly
    290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
        355                 360                 365
Ser Leu Ser Thr Ser Thr His Gly Asn Thr Asn Thr Ser Ile Asn Pro
    370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Asn Gln Ile Pro Leu Val Lys Gly Phe
            500                 505                 510
Arg Val Trp Gly Gly Thr Ser Val Ile Thr Gly Pro Gly Phe Thr Gly
```

```
            515                 520                 525
Gly Asp Ile Leu Arg Arg Asn Thr Phe Gly Asp Phe Val Ser Leu Gln
            530                 535                 540
Val Asn Ile Asn Ser Pro Ile Thr Gln Arg Tyr Arg Leu Arg Phe Arg
545                 550                 555                 560
Tyr Ala Ser Ser Arg Asp Ala Arg Val Ile Val Leu Thr Gly Ala Ala
                565                 570                 575
Ser Thr Gly Val Gly Gly Gln Val Ser Val Asn Met Pro Leu Gln Lys
            580                 585                 590
Thr Met Glu Ile Gly Glu Asn Leu Thr Ser Arg Thr Phe Arg Tyr Thr
            595                 600                 605
Asp Phe Ser Asn Pro Phe Ser Phe Arg Ala Asn Pro Asp Ile Ile Gly
            610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Thr Ala
                645                 650                 655
Thr Phe Glu Ala Glu Ser Asp Leu Glu Arg Ala Arg Lys Ala Val Asn
                660                 665                 670
Ala Leu Phe Thr Ser Thr Asn Pro Arg Gly Leu Lys Thr Asp Val Thr
            675                 680                 685
Asp Tyr His Ile Asp Gln Val Ser Asn Leu Val Glu Cys Leu Ser Asp
            690                 695                 700
Glu Phe Cys Leu Asp Lys Lys Arg Glu Leu Leu Glu Glu Val Lys Tyr
705                 710                 715                 720
Ala Lys Arg Leu Ser Asp Glu Arg Asn Leu Leu Gln Asp Pro Thr Phe
                725                 730                 735
Thr Ser Ile Ser Gly Gln Thr Asp Arg Gly Trp Ile Gly Ser Thr Gly
            740                 745                 750
Ile Ser Ile Gln Gly Gly Asp Asp Ile Phe Lys Glu Asn Tyr Val Arg
            755                 760                 765
Leu Pro Gly Thr Val Asp Glu Cys Tyr Pro Thr Tyr Leu Tyr Gln Lys
            770                 775                 780
Ile Asp Glu Ser Gln Leu Lys Ser Tyr Thr Arg Tyr Gln Leu Arg Gly
785                 790                 795                 800
Tyr Ile Glu Asp Ser Gln Asp Leu Glu Ile Tyr Leu Ile Arg Tyr Asn
                805                 810                 815
Ala Lys His Glu Thr Leu Ser Val Pro Gly Thr Glu Ser Pro Trp Pro
                820                 825                 830
Ser Ser Gly Val Tyr Pro Ser Gly Arg Cys Gly Glu Pro Asn Arg Cys
            835                 840                 845
Ala Pro Arg Ile Glu Trp Asn Pro Asp Leu Asp Cys Ser Cys Arg Tyr
            850                 855                 860
Gly Glu Lys Cys Val His His Ser His His Phe Ser Leu Asp Ile Asp
865                 870                 875                 880
Val Gly Cys Thr Asp Leu Asn Glu Asp Leu Gly Val Trp Val Ile Phe
                885                 890                 895
Lys Ile Lys Thr Gln Asp Gly His Ala Lys Leu Gly Asn Leu Glu Phe
                900                 905                 910
Ile Glu Glu Lys Pro Leu Leu Gly Lys Ala Leu Ser Arg Val Lys Arg
            915                 920                 925
Ala Glu Lys Lys Trp Arg Asp Lys Tyr Glu Lys Leu Gln Leu Glu Thr
            930                 935                 940
```

```
Lys Arg Val Tyr Thr Glu Ala Lys Glu Ser Val Asp Ala Leu Phe Val
945                 950                 955                 960

Asp Ser Gln Tyr Asp Lys Leu Gln Ala Asn Thr Asn Ile Gly Ile Ile
            965                 970                 975

His Gly Ala Asp Lys Gln Val His Arg Ile Arg Glu Pro Tyr Leu Ser
            980                 985                 990

Glu Leu Pro Val Ile Pro Ser Ile Asn Ala Ala Ile Phe Glu Glu Leu
            995                 1000                1005

Glu Gly His Ile Phe Lys Ala Tyr Ser Leu Tyr Asp Ala Arg Asn
    1010            1015                1020

Val Ile Lys Asn Gly Asp Phe Asn Asn Gly Leu Ser Cys Trp Asn
    1025            1030                1035

Val Lys Gly His Val Asp Val Gln Gln Asn His His Arg Ser Val
    1040            1045                1050

Leu Val Leu Ser Glu Trp Glu Ala Glu Val Ser Gln Lys Val Arg
    1055            1060                1065

Val Cys Pro Asp Arg Gly Tyr Ile Leu Arg Val Thr Ala Tyr Lys
    1070            1075                1080

Glu Gly Tyr Gly Glu Gly Cys Val Thr Ile His Glu Phe Glu Asp
    1085            1090                1095

Asn Thr Asp Val Leu Lys Phe Arg Asn Phe Val Glu Glu Val
    1100            1105                1110

Tyr Pro Asn Asn Thr Val Thr Cys Asn Asp Tyr Thr Thr Asn Gln
    1115            1120                1125

Ser Ala Glu Gly Ser Thr Asp Ala Cys Asn Ser Tyr Asn Arg Gly
    1130            1135                1140

Tyr Glu Asp Gly Tyr Glu Asn Arg Tyr Glu Pro Asn Pro Ser Ala
    1145            1150                1155

Pro Val Asn Tyr Thr Pro Thr Tyr Glu Glu Gly Met Tyr Thr Asp
    1160            1165                1170

Thr Gln Gly Tyr Asn His Cys Val Ser Asp Arg Gly Tyr Arg Asn
    1175            1180                1185

His Thr Pro Leu Pro Ala Gly Tyr Val Thr Leu Glu
    1190            1195                1200

<210> SEQ ID NO 44
<211> LENGTH: 3687
<212> TYPE: DNA
<213> ORGANISM: Artificial
<220> FEATURE:
<223> OTHER INFORMATION: Synthetic nucleotide sequence designed for
      expression in a plant cell encoding TIC868_15.

<400> SEQUENCE: 44
atgacgagca accggaagaa cgagaacgag atcatcaacg ccctctcgat ccctgctgtt     60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat cgccggtca gatcgcgtcc   240 ttctactcgt tccttgtggg cgagctgtgg cctcgcggtc gtgaccgtg ggagatcttc   300 ctggagcatg tggagcagtt gatccggcag caagtcacgg agaacacccg cgatactgct   360
ctggccaggc tacagggcct ggaaaactcc tttcgggcat accagcagtc actgaggac   420 tggttggaga acaggatga cgcgcgaaca cgctcggtac tctacaccca gtacatcgct   480
```

```
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cggatgctac cttgaagca   1980 gagtccgact ggaacgtgc acagaaggca gtgaacgcac tcttcacctc aagcaaccag   2040
atcggattga agacagatgt gacagattac cacatcgacc aagtgagcaa cttggtggat   2100
tgcttgtcag atgagttctg cttggatgag aagcgtgaac tctccgagaa ggtgaagcac   2160
gcaaagcgtc tctcagatga acgtaatctc cttcaagacc ctaactttcg tggtatcaat   2220
cgtcagccag atcgtggatg gcgtggatca acagacatca ccatccaggg aggcgatgat   2280
gtgttcaagg agaactacgt gaccctccca ggaaccgtgg atgaatgcta cccaacctac   2340
ctctaccaga agatcgacga gtcaaagctc aaggcttaca cccgttatga actccgtggc   2400
tacatcgaag atagccagga tctcgaaatc tatctcatcc gttacaatgc taagcacgaa   2460
atcgtgaatg tgccaggaac cggctcactc tggccactct cagcacagtc accaatcggc   2520
aagtgcggcg aacccaatcg ctgcgctcct catctcgaat ggaatcccga tctcgactgc   2580
tcctgccgag acgcgagaa gtgtgcacat cactcacacc acttcacccct cgacatcgac   2640 gtgggctgca ccgacctcaa tgaagacctg ggcgtgtggg tgatcttcaa gatcaagacc   2700
caggacggcc acgcacgact gggcaatctg gagtttctgg aggagaagcc actgcttggc   2760
gaggcactgg cacgagtgaa acgagccgag aagaaatggc gagacaaacg tgagaagctg   2820
caactggaga ccaacatcgt gtacaaagag gccaaagagt cagttgacgc cctgtttgtc   2880
```

```
aatagccagt atgaccgact gcaagttgac accaacatcg ccatgatcca cgctgcggac    2940
aagcgcgtcc accgcatccg cgaggcttat ctgcccgagc tgagcgtcat tcccggcgtc    3000
aatgccgcga tcttcgagga gttagagggc cgcatcttca ccgcctacag cctctatgac    3060
gcccgcaatg tcattaagaa tggcgacttc aacaatggct actatgctg gaatgtcaaa     3120 gggcacgttg acgtcgagga gcagaacaat caccgcagcg tcttagtcat acccgagtgg    3180
gaggccgaag tcagccagga agtccgcgtc tgtccagggc gcgggtacat cctgcgggtc    3240
accgcctaca agagggata cggcgagggt tgtgtcacca tacacgagat agaggacaat     3300
accgacgaac tcaagttcag caattgtgtc gaggaggaag tctatcccaa caataccgta    3360
acctgcaaca actacaccgg aacccaggag gagtatgaag ggacgtacac ctcgcggaac    3420
cagggctatg acgaagccta tgggaacaac ccgtcggtgc ctgctgacta tgcgtcggtc    3480
tatgaggaga atcgtacac ggacgggcgg cgggagaatc cgtgtgagtc gaatcgcggg     3540
tatggtgact acacgccgct accggcgggc tatgtaacga aagacctgga atacttcccg    3600
gagacggaca agtatggat agagataggc gagacggagg gaacgttcat cgtggactcg     3660
gtagagctgc tgctcatgga ggagtga                                        3687
```

<210> SEQ ID NO 45
<211> LENGTH: 1228
<212> TYPE: PRT
<213> ORGANISM: Artificial
<220> FEATURE:
<223> OTHER INFORMATION: Amino acid sequence of the chimeric protein
      variant TIC868_15.

<400> SEQUENCE: 45

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205
```

-continued

Thr Ser Gln Glu Ile Gln Arg Tyr Tyr Glu Arg Gln Val Glu Lys Thr
210             215                 220

Arg Glu Tyr Ser Asp Tyr Cys Ala Arg Trp Tyr Asn Thr Gly Leu Asn
225             230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu

```
            625                 630                 635                 640
Leu Tyr Ile Asp Lys Ile Glu Ile Ile Leu Ala Asp Ala Thr Asp Ala
                645                 650                 655

Thr Phe Glu Ala Glu Ser Asp Leu Glu Arg Ala Gln Lys Ala Val Asn
                660                 665                 670

Ala Leu Phe Thr Ser Ser Asn Gln Ile Gly Leu Lys Thr Asp Val Thr
                675                 680                 685

Asp Tyr His Ile Asp Gln Val Ser Asn Leu Val Asp Cys Leu Ser Asp
                690                 695                 700

Glu Phe Cys Leu Asp Glu Lys Arg Glu Leu Ser Glu Lys Val Lys His
705                 710                 715                 720

Ala Lys Arg Leu Ser Asp Glu Arg Asn Leu Leu Gln Asp Pro Asn Phe
                725                 730                 735

Arg Gly Ile Asn Arg Gln Pro Asp Arg Gly Trp Arg Gly Ser Thr Asp
                740                 745                 750

Ile Thr Ile Gln Gly Gly Asp Asp Val Phe Lys Glu Asn Tyr Val Thr
                755                 760                 765

Leu Pro Gly Thr Val Asp Glu Cys Tyr Pro Thr Tyr Leu Tyr Gln Lys
                770                 775                 780

Ile Asp Glu Ser Lys Leu Lys Ala Tyr Thr Arg Tyr Glu Leu Arg Gly
785                 790                 795                 800

Tyr Ile Glu Asp Ser Gln Asp Leu Glu Ile Tyr Leu Ile Arg Tyr Asn
                805                 810                 815

Ala Lys His Glu Ile Val Asn Val Pro Gly Thr Gly Ser Leu Trp Pro
                820                 825                 830

Leu Ser Ala Gln Ser Pro Ile Gly Lys Cys Gly Glu Pro Asn Arg Cys
                835                 840                 845

Ala Pro His Leu Glu Trp Asn Pro Asp Leu Asp Cys Ser Cys Arg Asp
                850                 855                 860

Gly Glu Lys Cys Ala His His Ser His His Phe Thr Leu Asp Ile Asp
865                 870                 875                 880

Val Gly Cys Thr Asp Leu Asn Glu Asp Leu Gly Val Trp Val Ile Phe
                885                 890                 895

Lys Ile Lys Thr Gln Asp Gly His Ala Arg Leu Gly Asn Leu Glu Phe
                900                 905                 910

Leu Glu Glu Lys Pro Leu Leu Gly Glu Ala Leu Ala Arg Val Lys Arg
                915                 920                 925

Ala Glu Lys Lys Trp Arg Asp Lys Arg Glu Lys Leu Gln Leu Glu Thr
930                 935                 940

Asn Ile Val Tyr Lys Glu Ala Lys Glu Ser Val Asp Ala Leu Phe Val
945                 950                 955                 960

Asn Ser Gln Tyr Asp Arg Leu Gln Val Asp Thr Asn Ile Ala Met Ile
                965                 970                 975

His Ala Ala Asp Lys Arg Val His Arg Ile Arg Glu Ala Tyr Leu Pro
                980                 985                 990

Glu Leu Ser Val Ile Pro Gly Val Asn Ala Ala Ile Phe Glu Glu Leu
                995                 1000                1005

Glu Gly Arg Ile Phe Thr Ala Tyr Ser Leu Tyr Asp Ala Arg Asn
                1010                1015                1020

Val Ile Lys Asn Gly Asp Phe Asn Asn Gly Leu Leu Cys Trp Asn
                1025                1030                1035

Val Lys Gly His Val Asp Val Glu Glu Gln Asn Asn His Arg Ser
                1040                1045                1050
```

```
Val Leu Val Ile Pro Glu Trp Glu Ala Glu Val Ser Gln Glu Val
    1055                1060                1065

Arg Val Cys Pro Gly Arg Gly Tyr Ile Leu Arg Val Thr Ala Tyr
    1070                1075                1080

Lys Glu Gly Tyr Gly Glu Gly Cys Val Thr Ile His Glu Ile Glu
    1085                1090                1095

Asp Asn Thr Asp Glu Leu Lys Phe Ser Asn Cys Val Glu Glu Glu
    1100                1105                1110

Val Tyr Pro Asn Asn Thr Val Thr Cys Asn Asn Tyr Thr Gly Thr
    1115                1120                1125

Gln Glu Glu Tyr Glu Gly Thr Tyr Thr Ser Arg Asn Gln Gly Tyr
    1130                1135                1140

Asp Glu Ala Tyr Gly Asn Asn Pro Ser Val Pro Ala Asp Tyr Ala
    1145                1150                1155

Ser Val Tyr Glu Glu Lys Ser Tyr Thr Asp Gly Arg Arg Glu Asn
    1160                1165                1170

Pro Cys Glu Ser Asn Arg Gly Tyr Gly Asp Tyr Thr Pro Leu Pro
    1175                1180                1185

Ala Gly Tyr Val Thr Lys Asp Leu Glu Tyr Phe Pro Glu Thr Asp
    1190                1195                1200

Lys Val Trp Ile Glu Ile Gly Glu Thr Glu Gly Thr Phe Ile Val
    1205                1210                1215

Asp Ser Val Glu Leu Leu Leu Met Glu Glu
    1220                1225

<210> SEQ ID NO 46
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_29.

<400> SEQUENCE: 46
atgacgagca accggaagaa cgagaacgag atcatcaacg ccctctcgat ccctgctgtt    60
tcaaaccact ccgcgcagat gaacctgtcc accgacgcgc gcatcgagga ctccctctgc   120
atagccgagg caacaacat cgacccattc gtgtcggcca gcacggttca gaccggcatc    180
aacatcgcgg gccgtatcct cggcgtcctc ggtgtcccat cgccggtca gatcgcgtcc    240 ttctactcgt tccttgtggg cgagctgtgg cctcgcggtc gtgaccccgtg ggagatcttc   300 ctggagcatg tggagcagtt gatccggcag caagtcacgg agaacacccg cgatactgct   360
ctggccaggc tacagggcct gggaaactcc tttcgggcat accagtactc actggaggac   420
tggttggaga acagggatga cgcgcgaaca cgctcggtac tctacaccca gtacatcgct   480
ctcgaactcg acttcctgaa cgctatgccg ctgttcgcca tcaggaacca ggaagttcca   540
ctccttatgg tgtacgccca ggccgccaac ttacatctgc tcctgctgcg ggacgccagc   600
ctgttcggct ccgagttcgg actcacatct caagaaatcc agcgttacta cgagcgccaa   660
gtggagaaga cccgtgagta cagtgactac tgcgctcgat ggtacaacac agggctcaac   720
aacctgcgcg gcaccaacgc tgagtcatgg ctccgttaca ccagttccg ccgcgacttg    780 actttgggtg tcctagacct ggtggcgcta ttcccgtctt acgacacacg ggtgtaccca   840
atgaacacta gcgcgcaact cacgcgggag atctacacag acccaatcgg ccggacgaac   900
gcaccctccg gtttcgcatc cacgaattgg ttcaacaaca acgcaccctc cttctcggca   960
```

```
atcgaggccg ccgtcatccg ccctcctcac ctgctcgact ttcccgagca gctcacgatc   1020
ttctcccagc tctcacgctg gtcccacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtctgac   1980
ctggagcggg ctcagaaggc tgtcaacgaa ctgttcacca gcagcaacca gattgggctc   2040
aagaccgacg tcacggacta tcacattgac caagtgtcca accttgtgga gtgcctgtcc   2100
gacgagttct gcctcgacga gaagaaggag ctgtccgaga aggtcaaaca cgcgaagcgt   2160
ctgagtgacg agcggaattt gctccaggac ccgaacttcc gtggcatcaa ccgccagctc   2220
gaccgtggtt ggcgcgggag tacagacatc accatccagg gaggcgacga tgtgttcaag   2280
gagaactatg tgacgctgct cgggactttc gacgaatgct acccgacgta tctctaccag   2340
aagatagacg agagtaaatt gaaggcgtac acccgctacc agcttcgcgg gtacatcgag   2400
gatagtcagg acctggaaat ctacctgatc cgatacaacg ccaagcacga gacagtgaac   2460
gtgccaggca cgggctcact ttggccattg agcgctccct ctccaatcgg aaagtgcgct   2520
caccactcgc accacttctc tctggacatc gacgtgggct gcaccgacct caacgaggac   2580
ctgggtgtct gggttatctt caagattaag acccaggacg gacatgcccg cctcggcaac   2640
ctggagttcc ttgaggagaa gcctctcgtg ggcgaggccc tcgctcgtgt gaagcgcgcc   2700
gagaagaaat ggcgagacaa gcgggagaag ctggagtggg agaccaacat cgtgtacaag   2760
gaggccaagg agtcagtgga cgcactcttc gtcaacagcc agtacgaccg cctccaggct   2820
gacaccaaca tcgccatgat ccacgcggct gacaagcggg tccacagcat ccgtgaggcg   2880
tacctgcccg agctgtcagt gatccctggt gtgaacgcgg cgatcttcga ggaactggag   2940
ggccgcatct tcacagcatt cagcctgtac gatgccagga atgttattaa gaacggtgac   3000
ttcaacaacg ggctgagttg ctggaacgtc aagggccatg tggacgtcga ggagcagaac   3060
aaccaccggt ccgtgctggt cgtgccggag tgggaggcag aggtgagcca ggaggtccgc   3120
gtctgccctg gtcgcggcta catcctccgt gtgactgcgt acaaggaagg ctacggtgaa   3180
ggctgcgtga ctatccacga gatcgagaac aacaccgacg agctcaagtt ctcgaactgt   3240
gtggaggagg aggtgtaccc gaacaacacc gttacttgca acgactacac tgccacgcaa   3300
```

```
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca acccttgcga gtccaaccgt ggctacggtg actacactcc gctgcccgcc    3480
gggtacgtca ccaaggagct ggagtacttc ccggagaccg acaaagtctg gatcgagatc    3540
ggcgagacgg agggcacttt catcgtggac tcggtcgagc tgctactgat ggaggagtga    3600
```

<210> SEQ ID NO 47
<211> LENGTH: 1199
<212> TYPE: PRT
<213> ORGANISM: Artificial
<220> FEATURE:
<223> OTHER INFORMATION: Amino acid sequence of the chimeric protein
      variant TIC868_29.

<400> SEQUENCE: 47

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Tyr Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
```

```
            305                 310                 315                 320
        Ile Glu Ala Ala Val Ile Arg Pro Pro His Leu Leu Asp Phe Pro Glu
                        325                 330                 335

Gln Leu Thr Ile Phe Ser Gln Leu Ser Arg Trp Ser His Thr Gln Tyr
                        340                 345                 350

Met Asn Tyr Trp Val Gly His Arg Leu Glu Ser Arg Thr Ile Arg Gly
                        355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
        385                 390                 395                 400

Ala Gly Ile Asn Ile Leu Leu Thr Thr Pro Val Asn Gly Val Pro Trp
                        405                 410                 415

Ala Arg Phe Asn Trp Arg Asn Pro Leu Asn Ser Leu Arg Gly Ser Leu
                        420                 425                 430

Leu Tyr Thr Ile Gly Tyr Thr Gly Val Gly Thr Gln Leu Phe Asp Ser
                        435                 440                 445

Glu Thr Glu Leu Pro Pro Glu Thr Thr Glu Arg Pro Asn Tyr Glu Ser
                450                 455                 460

Tyr Ser His Arg Leu Ser Asn Ile Arg Leu Ile Ser Gly Asn Thr Leu
        465                 470                 475                 480

Arg Ala Pro Val Tyr Ser Trp Thr His Arg Ser Ala Asp Arg Thr Asn
                        485                 490                 495

Thr Ile Ser Ser Asp Ser Ile Asn Gln Ile Pro Leu Val Lys Gly Phe
                        500                 505                 510

Arg Val Trp Gly Gly Thr Ser Val Ile Thr Gly Pro Gly Phe Thr Gly
                        515                 520                 525

Gly Asp Ile Leu Arg Arg Asn Thr Phe Gly Asp Phe Val Ser Leu Gln
                530                 535                 540

Val Asn Ile Asn Ser Pro Ile Thr Gln Arg Tyr Arg Leu Arg Phe Arg
        545                 550                 555                 560

Tyr Ala Ser Ser Arg Asp Ala Arg Val Ile Val Leu Thr Gly Ala Ala
                        565                 570                 575

Ser Thr Gly Val Gly Gly Gln Val Ser Val Asn Met Pro Leu Gln Lys
                        580                 585                 590

Thr Met Glu Ile Gly Glu Asn Leu Thr Ser Arg Thr Phe Arg Tyr Thr
                        595                 600                 605

Asp Phe Ser Asn Pro Phe Ser Phe Arg Ala Asn Pro Asp Ile Ile Gly
                        610                 615                 620

Ile Ser Glu Gln Pro Leu Phe Gly Ala Gly Ser Ile Ser Ser Gly Glu
        625                 630                 635                 640

Leu Tyr Ile Asp Lys Ile Glu Ile Ile Leu Ala Asp Ala Thr Phe Glu
                        645                 650                 655

Ala Glu Ser Asp Leu Glu Arg Ala Gln Lys Ala Val Asn Glu Leu Phe
                        660                 665                 670

Thr Ser Ser Asn Gln Ile Gly Leu Lys Thr Asp Val Thr Asp Tyr His
                        675                 680                 685

Ile Asp Gln Val Ser Asn Leu Val Glu Cys Leu Ser Asp Glu Phe Cys
                        690                 695                 700

Leu Asp Glu Lys Lys Glu Leu Ser Glu Lys Val Lys His Ala Lys Arg
        705                 710                 715                 720

Leu Ser Asp Glu Arg Asn Leu Leu Gln Asp Pro Asn Phe Arg Gly Ile
                        725                 730                 735
```

```
Asn Arg Gln Leu Asp Arg Gly Trp Arg Gly Ser Thr Asp Ile Thr Ile
             740                 745                 750

Gln Gly Gly Asp Asp Val Phe Lys Glu Asn Tyr Val Thr Leu Leu Gly
             755                 760                 765

Thr Phe Asp Glu Cys Tyr Pro Thr Tyr Leu Tyr Gln Lys Ile Asp Glu
             770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
             805                 810                 815

Glu Thr Val Asn Val Pro Gly Thr Gly Ser Leu Trp Pro Leu Ser Ala
             820                 825                 830

Pro Ser Pro Ile Gly Lys Cys Ala His His Ser His His Phe Ser Leu
             835                 840                 845

Asp Ile Asp Val Gly Cys Thr Asp Leu Asn Glu Asp Leu Gly Val Trp
             850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
             885                 890                 895

Val Lys Arg Ala Glu Lys Lys Trp Arg Asp Lys Arg Glu Lys Leu Glu
             900                 905                 910

Trp Glu Thr Asn Ile Val Tyr Lys Glu Ala Lys Glu Ser Val Asp Ala
             915                 920                 925

Leu Phe Val Asn Ser Gln Tyr Asp Arg Leu Gln Ala Asp Thr Asn Ile
             930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
             965                 970                 975

Glu Glu Leu Glu Gly Arg Ile Phe Thr Ala Phe Ser Leu Tyr Asp Ala
             980                 985                 990

Arg Asn Val Ile Lys Asn Gly Asp Phe Asn Asn Gly Leu Ser Cys Trp
             995                 1000                1005

Asn Val Lys Gly His Val Asp Val Glu Glu Gln Asn Asn His Arg
             1010                1015                1020

Ser Val Leu Val Val Pro Glu Trp Glu Ala Glu Val Ser Gln Glu
             1025                1030                1035

Val Arg Val Cys Pro Gly Arg Gly Tyr Ile Leu Arg Val Thr Ala
             1040                1045                1050

Tyr Lys Glu Gly Tyr Gly Gly Cys Val Thr Ile His Glu Ile
             1055                1060                1065

Glu Asn Asn Thr Asp Glu Leu Lys Phe Ser Asn Cys Val Glu Glu
             1070                1075                1080

Glu Val Tyr Pro Asn Asn Thr Val Thr Cys Asn Asp Tyr Thr Ala
             1085                1090                1095

Thr Gln Glu Glu Tyr Glu Gly Thr Tyr Thr Ser Arg Asn Arg Gly
             1100                1105                1110

Tyr Asp Gly Ala Tyr Glu Ser Asn Ser Ser Val Pro Ala Asp Tyr
             1115                1120                1125

Ala Ser Ala Tyr Glu Glu Lys Ala Tyr Thr Asp Gly Arg Arg Asp
             1130                1135                1140
```

| | | |
|---|---|---|
| Asn Pro Cys Glu Ser Asn Arg Gly Tyr Gly Asp Tyr Thr Pro Leu | | |
| 1145 | 1150 | 1155 |
| Pro Ala Gly Tyr Val Thr Lys Glu Leu Glu Tyr Phe Pro Glu Thr | | |
| 1160 | 1165 | 1170 |
| Asp Lys Val Trp Ile Glu Ile Gly Glu Thr Gly Thr Phe Ile | | |
| 1175 | 1180 | 1185 |
| Val Asp Ser Val Glu Leu Leu Leu Met Glu Glu | | |
| 1190 | 1195 | |

<210> SEQ ID NO 48
<211> LENGTH: 3432
<212> TYPE: DNA
<213> ORGANISM: Artificial
<220> FEATURE:
<223> OTHER INFORMATION: Recombinant nucleotide sequence used for
      expression in a bacterial cell encoding TIC869.

<400> SEQUENCE: 48

| | |
|---|---|
| atggagataa ataatcagaa gcaatgcata ccatataatt gcttaagtaa tcctgaggaa | 60 |
| gtacttttgg atggggagag gatattacct gatatcgatc cactcgaagt ttctttgtcg | 120 |
| cttttgcaat ttcttttgaa taactttgtt ccagggggag gctttatttc aggattagtt | 180 |
| gataaaatat gggggggcttt gagaccatct gaatgggact tatttcttgc acagattgaa | 240 |
| cggttgattg atcaaagaat agaagcaaca gtaagagcaa agcaatcac tgaattagaa | 300 |
| ggattaggga gaaattatca aatatacgct gaagcattta agaatgggaa atcagatcct | 360 |
| gataacgaag cggctaaaag tagagtaatt gatcgctttc gtatacttga tggtctaatt | 420 |
| gaagcaaata tcccttcatt tcggataatt ggatttgaag tgccacttttt atcggtttat | 480 |
| gttcaagcag ctaatctaca tctcgctcta ttgagagatt ctgttatttt tggagagaga | 540 |
| tggggattga cgacaaaaaa tgtcaatgat atctataata gacaaattag agaaattcat | 600 |
| gaatatagca atcattgcgt agatacgtat aacacagaac tagaacgtct agggtttaga | 660 |
| tctatagcgc agtggagaat atataatcag tttagaagag aactaacact aactgtatta | 720 |
| gatattgtcg ctcttttccc gaactatgac agtagactgt atccgatcca aacttttttct | 780 |
| caattgacaa gagaaattgt tacatcccca gtaagcgaat tttattatgg tgttattaat | 840 |
| agtggtaata taattggtac tcttactgaa cagcagataa ggcgaccaca tcttatggac | 900 |
| ttctttaact ccatgatcat gtatacatca gataatagac gggaacatta ttggtcagga | 960 |
| cttgaaatga cggcttattt tacaggattt gcaggagctc aagtgtcatt cccctttagtc | 1020 |
| gggactagag gggagtcagc tccaccatta actgttaaga gtgttaatga tggaattat | 1080 |
| agaatattat cggcaccgtt ttattcagcg cctttttctag gcaccattgt attgggaagt | 1140 |
| cgtggagaaa aatttgattt tgcgcttaat aatatttcac ctccgccatc tacaatatac | 1200 |
| agacatcctg gaacagtaga ttcactagtc agtataccgc cacaggataa tagcgtacca | 1260 |
| ccgcacaggg gatctagtca tcgattaagt catgttacaa tgcgcgcaag ttccctata | 1320 |
| ttccattgga cgcatcgcag cgcaaccact acaaatacaa ttaatccaaa tgctattatc | 1380 |
| caaataccac tagtaaaagc atttaacctt cattcaggtg ccactgttgt tagaggacca | 1440 |
| gggtttacag gtggagatct cttacgaaga acgaatactg tacatttgc agacataaga | 1500 |
| gtcaatgttc cttcatcact attttcccaa agatatcgcg taaggattcg ttatgcttct | 1560 |
| actaccgatt tacaattttt cacgagaatt aatggaactt ctgttaatca aggtaatttc | 1620 |
| tcaaaaacga tggatagagg ggataaactg aaatctgaaa actttagaac tgccggatttt | 1680 |

| | |
|---|---|
| agtactcctt ttagattttc aaattttcaa agtacattca cgttgggtac tcaggctttt | 1740 |
| tcaaatcagg aagtttatat agatagaatt gaatttgtcc cggcagaagt aacattcgag | 1800 |
| gcagaatctg atttagaaag agcacaaaag gcggtgaatg agctgtttac ttcttccaat | 1860 |
| caaatcgggt taaaaacaga tgtgacggat tatcatattg atcaagtatc caatttagtt | 1920 |
| gagtgtttat ctgatgaatt ttgtctggat gaaaaaaaag aattgtccga gaaagtcaaa | 1980 |
| catgcgaagc gacttagtga tgagcggaat ttacttcaag atccaaactt tagagggatc | 2040 |
| aatagacaac tagaccgtgg ctggagagga agtacggata ttaccatcca aggaggcgat | 2100 |
| gacgtattca agagaattca cgttacgcta ttgggtacct ttgatgagtg ctatccaacg | 2160 |
| tatttatatc aaaaaataga tgagtcgaaa ttaaaagcct atcccgttac ccaattaaga | 2220 |
| gggtatatcg aagatagtca agacttagaa atctatttaa ttcgctacaa tgccaaacac | 2280 |
| gaaacagtaa atgtgccagg tacgggttcc ttatggccgc tttcagcccc aagtccaatc | 2340 |
| ggaaaatgtg cccatcattc ccatcatttc tccttggaca ttgatgttgg atgtacagac | 2400 |
| ttaaatgagg acttaggtgt atgggtgata ttcaagatta gacgcaagat ggccatgca | 2460 |
| agactaggaa atctagaatt tctcgaagag aaaccattag taggagaagc actagctcgt | 2520 |
| gtgaaaagag cggagaaaaa atggagagac aaacgtgaaa aattggaatg ggaaacaaat | 2580 |
| attgtttata agaggcaaa agaatctgta gatgctttat ttgtaaactc tcaatatgat | 2640 |
| agattacaag cggataccaa catcgcgatg attcatgcgg cagataaacg cgttcatagc | 2700 |
| attcgagaag cttatctgcc tgagctgtct gtgattccgg gtgtcaatgc ggctattttt | 2760 |
| gaagaattag aagggcgtat tttcactgca ttctccctat atgatgcgag aaatgtcatt | 2820 |
| aaaaatggtg attttaataa tggcttatcc tgctggaacg tgaaagggca tgtagatgta | 2880 |
| gaagaacaaa acaaccaccg ttcggtcctt gttgttccgg aatgggaagc agaagtgtca | 2940 |
| caagaagttc gtgtctgtcc gggtcgtggc tatatccttc gtgtcacagc gtacaaggag | 3000 |
| ggatatggag aaggttgcgt aaccattcat gagatcgaga acaatacaga cgaactgaag | 3060 |
| tttagcaact gtgtagaaga ggaagtatat ccaaacaaca cggtaacgtg taatgattat | 3120 |
| actgcgactc aagaagaata tgagggtacg tacacttctc gtaatcgagg atatgacgga | 3180 |
| gcctatgaaa gcaattcttc tgtaccagct gattatgcat cagcctatga agaaaaagca | 3240 |
| tatacagatg gacgaagaga caatccttgt gaatctaaca gaggatatgg ggattacaca | 3300 |
| ccactaccag ctggctatgt gacaaaagaa ttagagtact tcccagaaac cgataaggta | 3360 |
| tggattgaga tcggagaaac ggaaggaaca ttcatcgtgg acagcgtgga attacttctt | 3420 |
| atggaggaat ag | 3432 |

<210> SEQ ID NO 49
<211> LENGTH: 3432
<212> TYPE: DNA
<213> ORGANISM: Artificial
<220> FEATURE:
<223> OTHER INFORMATION: Synthetic nucleotide sequence designed for
      expression in a plant cell encoding TIC869.

<400> SEQUENCE: 49

| | |
|---|---|
| atggagataa acaaccagaa gcagtgcatt ccgtacaact gcctcagcaa cccggaggag | 60 |
| gtgctgctgg acggcgagcg tatcctccca gacatcgacc cactggaggt cagcctgagc | 120 |
| ctcctccagt tcctcctcaa taacttcgtg ccaggcggcg gcttcatctc cggcctggtg | 180 |
| gacaagatct ggggcgcact ccggccaagt gagtgggatc tgttcctggc ccaaatcgag | 240 |

```
cgcctgatcg accagaggat cgaggcgacg gtccgcgcca aggcgataac cgagctggag    300
ggcctcggtc gcaactacca gatctacgca gaggcgttca aggagtggga gagcgacccg    360
gacaacgagg cggccaagtc tcgggtgatt gaccgcttcc gcatcctcga cggcctcatc    420
gaagccaaca tcccttcctt ccggatcata ggcttcgaag tcccgctcct cagcgtgtac    480
gtgcaagcgg ccaatctcca cctcgcgttg ctccgtgaca gcgtcatctt tggcgagaga    540
tggggcctga cgacgaagaa cgtgaacgac atctacaaca ggcagatccg agagattcac    600
gagtacagca accactgcgt ggacacatac aacacggagc tggagcggct cggcttccgc    660
tcaatcgctc agtggcggat ctacaaccag ttccgccgcg agctgaccct caccgtgctc    720
gacatcgtcg cattgtttcc caattacgac tcacgcctct acccaatcca gactttcagc    780
cagctcacac gcgagattgt gaccagcccg gtgtcagagt tctactacgg cgtcatcaac    840
tcaggcaaca tcatcgggac actgactgaa cagcagatca gacgtccgca cttgatggac    900
ttcttcaact ccatgattat gtacacatca gacaacagga gagagcacta ctggtccggg    960
ttggagatga ctgcttactt caccggcttc gccggtgccc aagtgagctt cccactggtc   1020
ggaactcgtg gcgagtcagc tcctccgcta actgtgcgat ctgtcaacga cgggatctac   1080
agaatactgt cggctccctt ctacagtgcg ccgttcctcg gcaccatcgt cctcggctca   1140
cgtggtgaga gttcgacttc gcactgaac aacattagcc cgccgcctag tacaatctac   1200
aggcaccctg gcaccgtgga ctcactggtt tcgatcccgc acaagacaa cagtgtgccg   1260 ccacatcgtg gttctagcca caggctctcc catgtgacca tgcgcgcctc ttcaccgatc   1320
tttcactgga cccatcggtc cgctacaacc acaaacacca tcaaccctaa cgccatcatc   1380
caaatcccgc tggtgaaggc gtttaacctc cacagcggcg caactgtcgt gcgcggccct   1440
ggattcaccg gtggtgacct gctccgtcgg accaatactg gcacgttcgc agacatccga   1500
gtgaacgtcc cgtcctcgct gttcagtcag cgctaccgtg tccgcattcg gtacgcttcc   1560
accacggatc tccagttctt tactcgcatc aatgggacga gcgtcaacca gggcaacttc   1620
agcaagacga tggaccgtgg agataagctc aagtccgaga acttccgcac ggctggcttc   1680
tcgacaccgt tcagattcag caacttccag agcactttca cgctgggcac acaggcgttc   1740
tccaaccagg aggtgtacat cgaccgcatc gagttcgtgc ctgctgaggt taccttcgag   1800
gcggaaagcg acctcgaaag ggcccagaag gccgtcaacg agctgttcac ctccagcaac   1860
cagatcggtc tcaagaccga cgtcactgac tatcacattg accaagtcag caacctggtg   1920
gagtgcctca gtgatgagtt ctgcctggat gagaagaagg agcttagcga gaaggtcaag   1980
cacgcaaagc gcttgagcga cgagcgcaac cttctccagg acccgaattt ccgtggtatc   2040
aatagacagc ttgaccgtgg gtggcgcggt agtaccgaca taaccatcca gggtggcgac   2100
gatgtgttca aggagaatta tgttacgctg ctcggtacgt tcgacgagtg ctatcccacg   2160
tacttgtacc agaagattga cgagagcaag ctcaaggcgt cacacccgtta ccagctccgt   2220 ggctacatcg aggacagcca ggatctggaa atctacctta tccgatacaa tgctaagcac   2280
gagacagtca acgtgcccgg aacagggtcg ctctggccgc tcagtgctcc gtcgcccatt   2340
ggcaagtgcg cgcaccattc gcatcacttc tcacttgaca ttgacgtggg ctgcaccgac   2400
ctgaacgagg atctgggtgt ctgggtcatc ttcaagatca agacccaaga cggccacgcg   2460
cgcctcggga acctggagtt cctggaggag aagcctttgg taggtgaagc cctggccccgc   2520 gtcaagcgcg cggagaagaa gtggcgcgac aagagggaga agctggaatg ggagaccaac   2580
atcgtgtaca aggaggcgaa ggagtcggtg gacgcactat tcgtgaactc ccagtacgac   2640
```

-continued

```
cgtctccagg ccgacaccaa catcgccatg atccacgccg ctgacaaacg agttcattcc   2700
attcgtgaag cctatcttcc cgagctgtct gtcataccgg cgtcaacgc ggccatcttc   2760 gaggagttag agggtcggat ctttacagct ttctcactgt acgatgcccg caacgtcatc   2820
aagaacggcg acttcaacaa cggtctctcc tgttggaacg tgaagggcca cgtggatgtc   2880
gaggagcaga acaaccaccg ctctgtgctt gtggtgcccg agtgggaggc cgaggtgagc   2940
caggaggtcc gcgtctgtcc gggtcgcggc tacatcctgc gggtcaccgc ctacaaggag   3000
ggctacggcg aaggctgcgt tactattcac gagattgaga acaataccga cgaactcaag   3060
ttctccaact gtgtcgagga ggaggtgtac ccgaacaaca ccgtgacgtg caacgactac   3120
accgcgacac aggaggaata cgagggcacc tacaccagcc gcaaccgagg ctacgacgga   3180
gcgtacgaga gcaactcgtc cgtgcccgct gattacgcga gtgcgtacga ggagaaggct   3240
tacaccgacg acggcgcga caatccctgc gagagtaacc gtggatacgg agattacacg   3300
ccgctacccg ctggctacgt cactaaggaa ctggagtact cccagagac ggacaaggtg   3360 tggatcgaaa tcggcgagac agagggcacg ttcatcgtgg actccgtgga gctgctgctg   3420
atggaggagt ga                                                      3432
```

<210> SEQ ID NO 50
<211> LENGTH: 1143
<212> TYPE: PRT
<213> ORGANISM: Artificial
<220> FEATURE:
<223> OTHER INFORMATION: Amino acid sequence of the chimeric protein TIC869.

<400> SEQUENCE: 50

```
Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Asp Pro Asp Asn Glu Ala Ala Lys Ser Arg
        115                 120                 125

Val Ile Asp Arg Phe Arg Ile Leu Asp Gly Leu Ile Glu Ala Asn Ile
    130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205
```

```
Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
                260                 265                 270

Glu Phe Tyr Tyr Gly Val Ile Asn Ser Gly Asn Ile Ile Gly Thr Leu
                275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Leu Thr Val
                340                 345                 350

Arg Ser Val Asn Asp Gly Ile Tyr Arg Ile Leu Ser Ala Pro Phe Tyr
                355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
                420                 425                 430

Thr Met Arg Ala Ser Ser Pro Ile Phe His Trp Thr His Arg Ser Ala
    435                 440                 445

Thr Thr Thr Asn Thr Ile Asn Pro Asn Ala Ile Ile Gln Ile Pro Leu
                450                 455                 460

Val Lys Ala Phe Asn Leu His Ser Gly Ala Thr Val Val Arg Gly Pro
465                 470                 475                 480

Gly Phe Thr Gly Gly Asp Leu Leu Arg Arg Thr Asn Thr Gly Thr Phe
                485                 490                 495

Ala Asp Ile Arg Val Asn Val Pro Ser Ser Leu Phe Ser Gln Arg Tyr
                500                 505                 510

Arg Val Arg Ile Arg Tyr Ala Ser Thr Thr Asp Leu Gln Phe Phe Thr
                515                 520                 525

Arg Ile Asn Gly Thr Ser Val Asn Gln Gly Asn Phe Ser Lys Thr Met
    530                 535                 540

Asp Arg Gly Asp Lys Leu Lys Ser Glu Asn Phe Arg Thr Ala Gly Phe
545                 550                 555                 560

Ser Thr Pro Phe Arg Phe Ser Asn Phe Gln Ser Thr Phe Thr Leu Gly
                565                 570                 575

Thr Gln Ala Phe Ser Asn Gln Glu Val Tyr Ile Asp Arg Ile Glu Phe
                580                 585                 590

Val Pro Ala Glu Val Thr Phe Glu Ala Glu Ser Asp Leu Glu Arg Ala
                595                 600                 605

Gln Lys Ala Val Asn Glu Leu Phe Thr Ser Ser Asn Gln Ile Gly Leu
    610                 615                 620

Lys Thr Asp Val Thr Asp Tyr His Ile Asp Gln Val Ser Asn Leu Val
```

```
                625                 630                 635                 640
            Glu Cys Leu Ser Asp Glu Phe Cys Leu Asp Glu Lys Lys Glu Leu Ser
                            645                 650                 655
            Glu Lys Val Lys His Ala Lys Arg Leu Ser Asp Glu Arg Asn Leu Leu
                            660                 665                 670
            Gln Asp Pro Asn Phe Arg Gly Ile Asn Arg Gln Leu Asp Arg Gly Trp
                            675                 680                 685
            Arg Gly Ser Thr Asp Ile Thr Ile Gln Gly Gly Asp Asp Val Phe Lys
                            690                 695                 700
            Glu Asn Tyr Val Thr Leu Leu Gly Thr Phe Asp Glu Cys Tyr Pro Thr
            705                 710                 715                 720
            Tyr Leu Tyr Gln Lys Ile Asp Glu Ser Lys Leu Lys Ala Tyr Thr Arg
                            725                 730                 735
            Tyr Gln Leu Arg Gly Tyr Ile Glu Asp Ser Gln Asp Leu Glu Ile Tyr
                            740                 745                 750
            Leu Ile Arg Tyr Asn Ala Lys His Glu Thr Val Asn Val Pro Gly Thr
                            755                 760                 765
            Gly Ser Leu Trp Pro Leu Ser Ala Pro Ser Pro Ile Gly Lys Cys Ala
                            770                 775                 780
            His His Ser His His Phe Ser Leu Asp Ile Asp Val Gly Cys Thr Asp
            785                 790                 795                 800
            Leu Asn Glu Asp Leu Gly Val Trp Val Ile Phe Lys Ile Lys Thr Gln
                            805                 810                 815
            Asp Gly His Ala Arg Leu Gly Asn Leu Glu Phe Leu Glu Glu Lys Pro
                            820                 825                 830
            Leu Val Gly Glu Ala Leu Ala Arg Val Lys Arg Ala Glu Lys Lys Trp
                            835                 840                 845
            Arg Asp Lys Arg Glu Lys Leu Glu Trp Glu Thr Asn Ile Val Tyr Lys
                            850                 855                 860
            Glu Ala Lys Glu Ser Val Asp Ala Leu Phe Val Asn Ser Gln Tyr Asp
            865                 870                 875                 880
            Arg Leu Gln Ala Asp Thr Asn Ile Ala Met Ile His Ala Ala Asp Lys
                            885                 890                 895
            Arg Val His Ser Ile Arg Glu Ala Tyr Leu Pro Glu Leu Ser Val Ile
                            900                 905                 910
            Pro Gly Val Asn Ala Ala Ile Phe Glu Glu Leu Glu Gly Arg Ile Phe
                            915                 920                 925
            Thr Ala Phe Ser Leu Tyr Asp Ala Arg Asn Val Ile Lys Asn Gly Asp
                            930                 935                 940
            Phe Asn Asn Gly Leu Ser Cys Trp Asn Val Lys Gly His Val Asp Val
            945                 950                 955                 960
            Glu Glu Gln Asn Asn His Arg Ser Val Leu Val Val Pro Glu Trp Glu
                            965                 970                 975
            Ala Glu Val Ser Gln Glu Val Arg Val Cys Pro Gly Arg Gly Tyr Ile
                            980                 985                 990
            Leu Arg Val Thr Ala Tyr Lys Glu Gly Tyr Gly Glu Gly Cys Val Thr
                            995                1000                1005
            Ile His Glu Ile Glu Asn Asn Thr Asp Glu Leu Lys Phe Ser Asn
                           1010                1015                1020
            Cys Val Glu Glu Glu Val Tyr Pro Asn Asn Thr Val Thr Cys Asn
                           1025                1030                1035
            Asp Tyr Thr Ala Thr Gln Glu Glu Tyr Glu Gly Thr Tyr Thr Ser
                           1040                1045                1050
```

```
Arg Asn Arg Gly Tyr Asp Gly Ala Tyr Glu Ser Asn Ser Ser Val
    1055            1060                1065

Pro Ala Asp Tyr Ala Ser Ala Tyr Glu Glu Lys Ala Tyr Thr Asp
    1070            1075                1080

Gly Arg Arg Asp Asn Pro Cys Glu Ser Asn Arg Gly Tyr Gly Asp
    1085            1090                1095

Tyr Thr Pro Leu Pro Ala Gly Tyr Val Thr Lys Glu Leu Glu Tyr
    1100            1105                1110

Phe Pro Glu Thr Asp Lys Val Trp Ile Glu Ile Gly Glu Thr Glu
    1115            1120                1125

Gly Thr Phe Ile Val Asp Ser Val Glu Leu Leu Leu Met Glu Glu
    1130            1135                1140

<210> SEQ ID NO 51
<211> LENGTH: 3513
<212> TYPE: DNA
<213> ORGANISM: Artificial
<220> FEATURE:
<223> OTHER INFORMATION: Recombinant nucleotide sequence used for
      expression in a bacterial cell encoding TIC836.

<400> SEQUENCE: 51
atggagaata atattcaaaa tcaatgcgta ccttacaatt gtttaaataa tcctgaagta     60
gaaatattaa atgaagaaag aagtactggc agattaccgt tagatatatc cttatcgctt    120
acacgtttcc ttttgagtga atttgttcca ggtgtgggag ttgcgtttgg attatttgat    180
ttaatatggg gttttataac tccttctgat tggagcttat ttcttttaca gattgaacaa    240
ttgattgagc aaagaatcaga acattggaa aggaaccggg caattactac attacgaggg    300
ttagcagata gctatgaaat ttatattgaa gcactaagag agtgggaagc aaatcctaat    360
aatgcacaat taagggaaga tgtgcgtatt cgatttgcta atacagacga cgctttaata    420
acagcaataa ataattttac acttacaagt tttgaaatcc ctcttttatc ggtctatgtt    480
caagcggcga atttacattt atcactatta agagacgctg tatcgtttgg gcagggttgg    540
ggactggata tagctactgt taataatcat tataatagat aataaatct tattcataga    600 tatacgaaac attgtttgga cacatacaat caaggattag aaaacttaag aggtactaat    660
actcgacaat gggcaagatt caatcagttt aggagagatt taacacttac tgtattagat    720
atcgttgctc ttttttccgaa ctacgatgtt agaacatatc caattcaaac gtcatcccaa    780
ttaacaaggg aaatttatac aagttcagta attgaggatt ctccagtttc tgctaatata    840
cctaatggtt ttaatagggc ggaatttgga gttagaccgc cccatcttat ggactttatg    900
aattctttgt ttgtaactgc agagactgtt agaagtcaaa ctgtgtgggg aggacactta    960
gttagttcac gaaatacggc tggtaaccgt ataaatttcc ctagttacgg ggtcttcaat   1020
cctggtggcg ccatttggat tgcagatgag gatccacgtc cttttttatcg gacattatca   1080 gatcctgttt ttgtccgagg aggatttggg aatcctcatt atgtactggg gcttagggga   1140
gtagcatttc aacaaactgg tacgaaccac acccgaacat ttagaaatag tgggaccata   1200
gattctctag atgaaatccc acctcaggat aatagtgggg caccttggaa tgattatagt   1260
catgtattaa atcatgttac atttgtacga tggccaggtg agatttcagg aagtgattca   1320
tggagagctc caatgttttc ttggacgcac cgtagtgcaa ccctacaaa tacaattgat   1380 ccggagagga ttcacaaat acctttaaca aatctctacta atcttggctc tggaacttct   1440
gtcgttaaag gaccaggatt tacaggagga gatattcttc gaagaacttc acctggccag   1500
```

```
atttcaacct taagagtaaa tattactgca ccattatcac aaagatatcg ggtaagaatt    1560
cgctacgctt ctaccacaaa tttacaattc catacatcaa ttgacggaag acctattaat    1620
caggggaatt tttcagcaac tatgagtagt gggagtaatt tacagtccgg aagctttagg    1680
actgtaggtt ttactactcc gtttaacttt tcaaatggat caagtgtatt tacgttaagt    1740
gctcatgtct tcaattcagg caatgaagtt tatatagatc gaattgaatt tgttccggca    1800
gaagtaacct tgaggcaga atatgattta gaaagagcgc agaaggcggt gaatgcgctg    1860
tttacgtcta caaaccaact agggctaaaa acaaatgtaa cggattatca tattgatcaa    1920
gtgtccaatt tagttacgta tttatcggat gaattttgtc tggatgaaaa gcgagaattg    1980
tccgagaaag tcaaacatgc gaagcgactc agtgatgaac gcaatttact ccaagattca    2040
aatttcaaag acattaatag gcaaccagaa cgtgggtggg gcggaagtac agggattacc    2100
atccaaggag gggatgacgt atttaaagaa aattacgtca cactatcagg tacctttgat    2160
gagtgctatc caacatattt gtatcaaaaa atcgatgaat caaaattaaa agcctttacc    2220
cgttatcaat taagagggta tatcgaagat agtcaagact tagaaatcta tttaattcgc    2280
tacaatgcaa aacatgaaac agtaaatgtg ccaggtacgg gttccttatg gccgctttca    2340
gcccaaagtc caatcggaaa gtgtggagag ccgaatcgat gcgcgccaca ccttgaatgg    2400
aatcctgact tagattgttc gtgtagggat ggagaaaagt gtgcccatca ttcgcatcat    2460
ttctccttag acattgatgt aggatgtaca gacttaaatg aggacctagg tgtatgggtg    2520
atctttaaga ttaagacgca agatgggcac gcaagactag gaatctaga gtttctcgaa    2580 gaaaaaccat tagtaggaga agcgctagct cgtgtgaaaa gagcggagaa aaaatggaga    2640
gacaaacgtg aaaaattgga atgggaaaca aatatcgttt ataaagaggc aaaagaatct    2700
gtagatgctt tatttgtaaa ctctcaatat gatcaattac aagcggatac gaatattgcc    2760
atgattcatg cggcagataa acgtgttcat agcattcgag aagcttatct gcctgagctg    2820
tctgtgattc cgggtgtcaa tgcggctatt tttgaagaat tagaagggcg tattttcact    2880
gcattctccc tatatgatgc gagaaatgtc attaaaaatg gtgattttaa taatggctta    2940
tcctgctgga acgtgaaagg gcatgtagat gtagaagaac aaaacaacca acgttcggtc    3000
cttgttgttc cggaatggga agcagaagtg tcacaagaag ttcgtgtctg tccgggtcgt    3060
ggctatatcc ttcgtgtcac agcgtacaag gagggatatg gagaaggttg cgtaaccatt    3120
catgagatcg agaacaatac agacgaactg aagtttagca actgcgtaga ggaggaaatc    3180
tatccaaata cacggtaac gtgtaatgat tatactgtaa atcaagaaga atacggaggt    3240
gcgtacactt ctcgtaatcg aggatataac gaagctcctt ccgtaccagc tgattatgcg    3300
tcagtctatg aagaaaaatc gtatacagat ggacgtagag agaatccttg tgaatttaac    3360
agagggtata gggattacac gccactacca gttggttatg tgacaaaaga attagaatac    3420
ttcccagaaa ccgataaggt atggattgag attggagaaa cggaaggaac atttatcgtg    3480
gacagcgtgg aattactcct tatggaggaa taa                                3513
```

<210> SEQ ID NO 52
<211> LENGTH: 3513
<212> TYPE: DNA
<213> ORGANISM: Artificial
<220> FEATURE:
<223> OTHER INFORMATION: Synthetic nucleotide sequence designed for
      expression in a plant cell encoding TIC836.

<400> SEQUENCE: 52

```
atggagaaca acatccagaa ccagtgcgtg ccctacaact gcctgaacaa ccctgaggtt      60
gagatcctga acgaggagcg tagcaccggt aggctcccgc tagacatctc cctgagcctg     120
acccgcttcc tccttagtga gttcgtgccc ggcgtgggcg tggccttcgg cctcttcgac     180
ctcatctggg gcttcatcac tccttccgac tggtccctct cctccttca gattgagcaa     240
ctgatcgagc agcgcatcga gacccttgag cgcaaccgcg ccatcaccac tctcagaggt     300
ctcgccgact cctacgaaat ctacatcgag gcactccgtg agtgggaggc caacccgaac     360
aatgcccagc tccgcgagga cgtgaggatc agattcgcca acaccgacga tgccctcatc     420
accgccatca acaatttcac cctcacctcc ttcgagatcc ctcttctgtc tgtgtacgtt     480
caagctgcta accttcacct ttccctcctg cgcgacgccg tgagcttcgg ccagggctgg     540
ggcctcgaca tcgccaccgt gaacaatcac tacaaccgcc tcatcaacct catccaccgc     600
tacaccaagc actgccttga cacctacaac cagggccttg agaacctccg tggcaccaac     660
acccgccagt gggcccgctt caaccagttc cgcagagacc tcaccctcac cgtgctcgac     720
atcgtggcac tcttcccaaa ctacgacgtg cgtacctacc ctatccagac ctccagccag     780
ctcaccaggg aaatctacac ctccagcgtg atcgaggact ctcctgtgtc cgccaacatc     840
cctaacggct tcaaccgcgc cgagttcggc gtgcgccctc ctcacctcat ggacttcatg     900
aactccctct tcgtcactgc cgagaccgtg cgctcccaga ccgtgtgggg cggtcacctc     960
gtgtccagcc gtaacaccgc tggcaacagg atcaacttcc cgtcctacgg cgtgttcaac    1020
ccaggcggtg ccatctggat cgccgatgaa gaccctcgtc ctttctaccg tacccgtgcc    1080
gaccctgtgt tcgtgcgtgg cggtttcggc aaccctcact acgtgctggg cctgcgtggc    1140
gtggccttcc agcaaaccgg caccaaccac accaggacgt tccgtaactc cggcaccatc    1200
gacagtcttg acgagatccc tccgcaagac aactccggtg caccttggaa cgactactcc    1260
cacgtgctga ccacgtgac cttcgtgagg tggcctggcg aaatctccgg ctccgactcc    1320
tggagggctc ctatgttcag ttggacccac aggagcgcta cgcctaccaa caccatcgac    1380
cctgagcgta tcactcagat ccctctgact aagagcacta acctgggcag cggcactagc    1440
gtggtcaagg gccctggctt cactggcggt gacatcctga ggcggactag ccctggccag    1500
atcagcactc tgagggtgaa catcactgct ccgctgagcc agcgttacag ggtcagaatc    1560
cgttacgctt ctactactaa ccttcagttc cacactagca tcgacggccg tccgatcaac    1620
cagggcaact tctctgctac tatgagttct ggcagtaacc tccagtctgg tagtttccgg    1680
actgtcggtt tcactacgcc gttcaacttc tccaacggta gttctgtctt cactctgtct    1740
gctcacgtgt tcaactctgg caacgaggtg tacatcgacc ggatcgagtt cgtccctgct    1800
gaggtgacgt tcgaggccga gtacgacctg agcgggctc agaaggctgt caacgctctg    1860
ttcacttcta ctaaccagct tggtttgaag actaacgtga ccgactacca cattgatcaa    1920
gtcagtaacc tggtcacgta cctgtctgac gagttctgtc ttgacgagaa gcgggagctg    1980
tctgagaagg tcaagcacgc taagcggctg tctgacgagc ggaacctgct tcaagacagt    2040
aacttcaagg acattaaccg ccagcctgag cgtggttggg gagggtccac gggtattacg    2100
attcaaggag gtgacgatgt ctttaaggag aactatgtga cgctttcggg tacgtttgat    2160
gagtgctatc caacgtacct ttaccagaag attgacgagt cgaagctgaa ggctttcact    2220
cgttaccagc ttcgtggtta cattgaggac tcgcaagacc tcgaaatcta cctcattcgt    2280
tacaacgcta agcacgagac tgtcaacgtc cctggtacgg gtagtctttg gccgctttct    2340
```

-continued

```
gctcagtcgc cgattggcaa gtgtggcgag ccgaaccgtt gcgctcctca cttggagtgg    2400
aacccggatc tcgattgctc gtgccgtgac ggtgagaagt gcgcgcacca tagtcatcac    2460
tttagccttg acattgatgt cggttgcacg gatcttaacg aggatcttgg agtctgggtg    2520
attttcaaga tcaaaactca ggatgggcac gcgcgtcttg gaatcttga gttcctggag     2580 gagaagccac ttgtcggtga ggcgcttgcg cgtgtcaagc gtgcggagaa gaaatggcgt    2640
gataagcgtg agaagttgga gtgggagacg aacatcgtgt acaaggaggc gaaggagtcg    2700
gtcgatgcgt tgtttgtcaa tagtcaatac gatcaattgc aagcggatac gaacatcgca    2760
atgattcatg cggcagataa gcgtgtccat tcgattcgtg aggcgtactt gccagagttg    2820
tcggtcatcc caggagttaa tgcggcaatc tttgaggaat ggagggcag aatcttcacg     2880 gcgttctcgt tgtacgatgc aagaaatgtt attaagaatg agatttcaa caatgggttg     2940 tcatgctgga atgttaaggg tcacgttgat gttgaagaac agaacaacca gagatcagtg    3000
ttggttgtac cagagtggga ggcagaggtt tcacaagagg tgagagtttg cccaggcaga    3060
ggctacatct tgagagttac agcatacaaa gagggatacg cgcgagggatg tgttacaatc   3120 cacgaaatcg agaacaatac cgatgagcta aagttctcaa attgtgttga ggaggagatc    3180
tacccgaaca cacgttac ttgtaatgat tacacagtga accaggagga gtatggtggt     3240
gcatacacat caagaaatag aggctacaat gaagcaccat cagttccagc agattatgcc    3300
tcagtttatg aggagaagtc atacacagat ggacgacgtg agaatccatg tgagttcaat    3360
cgaggatacc gagattacac accactacca gttggatacg ttacaaagga actagaatac    3420
ttcccagaaa cagataaagt atggatagag atcggagaaa cagaaggaac attcatcgtt    3480
gattcagtag aactactact tatggaagaa tga                                 3513
```

<210> SEQ ID NO 53
<211> LENGTH: 1170
<212> TYPE: PRT
<213> ORGANISM: Artificial
<220> FEATURE:
<223> OTHER INFORMATION: Amino acid sequence of the chimeric protein TIC836.

<400> SEQUENCE: 53

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
```

```
                145                 150                 155                 160
         Gln Ala Ala Asn Leu His Leu Ser Leu Leu Arg Asp Ala Val Ser Phe
                         165                 170                 175
         Gly Gln Gly Trp Gly Leu Asp Ile Ala Thr Val Asn Asn His Tyr Asn
                         180                 185                 190
         Arg Leu Ile Asn Leu Ile His Arg Tyr Thr Lys His Cys Leu Asp Thr
                         195                 200                 205
         Tyr Asn Gln Gly Leu Glu Asn Leu Arg Gly Thr Asn Thr Arg Gln Trp
                         210                 215                 220
         Ala Arg Phe Asn Gln Phe Arg Arg Asp Leu Thr Leu Thr Val Leu Asp
         225                 230                 235                 240
         Ile Val Ala Leu Phe Pro Asn Tyr Asp Val Arg Thr Tyr Pro Ile Gln
                         245                 250                 255
         Thr Ser Ser Gln Leu Thr Arg Glu Ile Tyr Thr Ser Ser Val Ile Glu
                         260                 265                 270
         Asp Ser Pro Val Ser Ala Asn Ile Pro Asn Gly Phe Asn Arg Ala Glu
                         275                 280                 285
         Phe Gly Val Arg Pro Pro His Leu Met Asp Phe Met Asn Ser Leu Phe
                         290                 295                 300
         Val Thr Ala Glu Thr Val Arg Ser Gln Thr Val Trp Gly Gly His Leu
         305                 310                 315                 320
         Val Ser Ser Arg Asn Thr Ala Gly Asn Arg Ile Asn Phe Pro Ser Tyr
                         325                 330                 335
         Gly Val Phe Asn Pro Gly Gly Ala Ile Trp Ile Ala Asp Glu Asp Pro
                         340                 345                 350
         Arg Pro Phe Tyr Arg Thr Leu Ser Asp Pro Val Phe Val Arg Gly Gly
                         355                 360                 365
         Phe Gly Asn Pro His Tyr Val Leu Gly Leu Arg Gly Val Ala Phe Gln
                         370                 375                 380
         Gln Thr Gly Thr Asn His Thr Arg Thr Phe Arg Asn Ser Gly Thr Ile
         385                 390                 395                 400
         Asp Ser Leu Asp Glu Ile Pro Pro Gln Asp Asn Ser Gly Ala Pro Trp
                         405                 410                 415
         Asn Asp Tyr Ser His Val Leu Asn His Val Thr Phe Val Arg Trp Pro
                         420                 425                 430
         Gly Glu Ile Ser Gly Ser Asp Ser Trp Arg Ala Pro Met Phe Ser Trp
                         435                 440                 445
         Thr His Arg Ser Ala Thr Pro Thr Asn Thr Ile Asp Pro Glu Arg Ile
         450                 455                 460
         Thr Gln Ile Pro Leu Thr Lys Ser Thr Asn Leu Gly Ser Gly Thr Ser
         465                 470                 475                 480
         Val Val Lys Gly Pro Gly Phe Thr Gly Gly Asp Ile Leu Arg Arg Thr
                         485                 490                 495
         Ser Pro Gly Gln Ile Ser Thr Leu Arg Val Asn Ile Thr Ala Pro Leu
                         500                 505                 510
         Ser Gln Arg Tyr Arg Val Arg Ile Arg Tyr Ala Ser Thr Thr Asn Leu
                         515                 520                 525
         Gln Phe His Thr Ser Ile Asp Gly Arg Pro Ile Asn Gln Gly Asn Phe
                         530                 535                 540
         Ser Ala Thr Met Ser Ser Gly Ser Asn Leu Gln Ser Gly Ser Phe Arg
         545                 550                 555                 560
         Thr Val Gly Phe Thr Thr Pro Phe Asn Phe Ser Asn Gly Ser Ser Val
                         565                 570                 575
```

```
Phe Thr Leu Ser Ala His Val Phe Asn Ser Gly Asn Glu Val Tyr Ile
            580                 585                 590

Asp Arg Ile Glu Phe Val Pro Ala Glu Val Thr Phe Glu Ala Glu Tyr
            595                 600                 605

Asp Leu Glu Arg Ala Gln Lys Ala Val Asn Ala Leu Phe Thr Ser Thr
            610                 615                 620

Asn Gln Leu Gly Leu Lys Thr Asn Val Thr Asp Tyr His Ile Asp Gln
625                 630                 635                 640

Val Ser Asn Leu Val Thr Tyr Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Ser Asn Phe Lys Asp Ile Asn Arg Gln
            675                 680                 685

Pro Glu Arg Gly Trp Gly Gly Ser Thr Gly Ile Thr Ile Gln Gly Gly
            690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Phe Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
            755                 760                 765

Asn Val Pro Gly Thr Gly Ser Leu Trp Pro Leu Ser Ala Gln Ser Pro
            770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
            820                 825                 830

Asn Glu Asp Leu Gly Val Trp Val Ile Phe Lys Ile Lys Thr Gln Asp
            835                 840                 845

Gly His Ala Arg Leu Gly Asn Leu Glu Phe Leu Glu Glu Lys Pro Leu
            850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
                885                 890                 895

Ala Lys Glu Ser Val Asp Ala Leu Phe Val Asn Ser Gln Tyr Asp Gln
            900                 905                 910

Leu Gln Ala Asp Thr Asn Ile Ala Met Ile His Ala Ala Asp Lys Arg
            915                 920                 925

Val His Ser Ile Arg Glu Ala Tyr Leu Pro Glu Leu Ser Val Ile Pro
            930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
            980                 985                 990
```

-continued

| | | | | | | | | | | | | | | |
|---|---|---|---|---|---|---|---|---|---|---|---|---|---|---|
| Glu | Gln | Asn | Asn | Gln | Arg | Ser | Val | Leu | Val | Val | Pro | Glu | Trp | Glu | Ala |
| | | 995 | | | | | 1000 | | | | | 1005 | | | |
| Glu | Val | Ser | Gln | Glu | Val | Arg | Val | Cys | Pro | Gly | Arg | Gly | Tyr | Ile |
| | 1010 | | | | | 1015 | | | | | 1020 | | | |
| Leu | Arg | Val | Thr | Ala | Tyr | Lys | Glu | Gly | Tyr | Gly | Glu | Gly | Cys | Val |
| | 1025 | | | | | 1030 | | | | | 1035 | | | |
| Thr | Ile | His | Glu | Ile | Glu | Asn | Asn | Thr | Asp | Glu | Leu | Lys | Phe | Ser |
| | 1040 | | | | | 1045 | | | | | 1050 | | | |
| Asn | Cys | Val | Glu | Glu | Glu | Ile | Tyr | Pro | Asn | Asn | Thr | Val | Thr | Cys |
| | 1055 | | | | | 1060 | | | | | 1065 | | | |
| Asn | Asp | Tyr | Thr | Val | Asn | Gln | Glu | Glu | Tyr | Gly | Gly | Ala | Tyr | Thr |
| | 1070 | | | | | 1075 | | | | | 1080 | | | |
| Ser | Arg | Asn | Arg | Gly | Tyr | Asn | Glu | Ala | Pro | Ser | Val | Pro | Ala | Asp |
| | 1085 | | | | | 1090 | | | | | 1095 | | | |
| Tyr | Ala | Ser | Val | Tyr | Glu | Glu | Lys | Ser | Tyr | Thr | Asp | Gly | Arg | Arg |
| | 1100 | | | | | 1105 | | | | | 1110 | | | |
| Glu | Asn | Pro | Cys | Glu | Phe | Asn | Arg | Gly | Tyr | Arg | Asp | Tyr | Thr | Pro |
| | 1115 | | | | | 1120 | | | | | 1125 | | | |
| Leu | Pro | Val | Gly | Tyr | Val | Thr | Lys | Glu | Leu | Glu | Tyr | Phe | Pro | Glu |
| | 1130 | | | | | 1135 | | | | | 1140 | | | |
| Thr | Asp | Lys | Val | Trp | Ile | Glu | Ile | Gly | Glu | Thr | Glu | Gly | Thr | Phe |
| | 1145 | | | | | 1150 | | | | | 1155 | | | |
| Ile | Val | Asp | Ser | Val | Glu | Leu | Leu | Leu | Met | Glu | Glu |
| | 1160 | | | | | 1165 | | | | | 1170 | |

US 10,669,317 B2

CHIMERIC INSECTICIDAL PROTEINS TOXIC OR INHIBITORY TO LEPIDOPTERAN PESTS

REFERENCE TO RELATED APPLICATION

This application is a continuation of U.S. patent application Ser. No. 14/884,469, filed Oct. 15, 2015, which claims the benefit of U.S. provisional application No. 62/064,989, filed Oct. 16, 2014, each of which are herein incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Dec. 11, 2017, having the file name P34230US04_SEQ.txt, and which is 371,792 bytes in size (as measured in the MS-Windows® operating system).

FIELD OF THE INVENTION

The invention generally relates to the field of insect inhibitory proteins. A novel class of chimeric insecticidal proteins exhibiting insect inhibitory activity against agriculturally-relevant pests of crop plants and seeds is disclosed in this application. In particular, the disclosed class of proteins exhibits insecticidal activity against the Lepidopteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields in infested areas. Lepidopteran pest species which negatively impact agriculture include, but are not limited to, fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (*Suleima helianthana*), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teerrellus*), southwestern corn borer (*Diatraea grandiosella*)), sugarcane borer (*Diatraea saccharalis*), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of other bacterial species, such as *Brevibacillus laterosporus*, *Lysinibacillus sphaericus* ("Ls" formerly known as *Bacillus sphaericus*) and *Paenibacillus popilliae*.

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

The development of resistance in target pests to insecticidal proteins creates the continuing need for discovery and development of new forms of insecticidal proteins that are useful for managing the increase in insect resistance to transgenic crops expressing insecticidal proteins. New insecticidal proteins with improved efficacy and which exhibit control over a broader spectrum of susceptible insect species will reduce the number of surviving insects which can develop resistance alleles. In addition, the use in one plant of two or more transgenic insecticidal proteins toxic to the same insect pest and displaying different modes of action reduces the probability of resistance in any single target insect species.

Consequently, there is a critical need to identify additional insecticidal proteins with improved insecticidal properties such as increased efficacy against a broader spectrum of target insect pests species and different modes of action compared to the toxins currently used in agricultural practices. To meet this need, the present invention discloses novel Cry1 chimeric insecticidal proteins that exhibit activity against significant target Lepidopteran pest species.

Members of the family of Cry1 crystal proteins are known in the art to exhibit bioactivity against Lepidopteran pests. The precursor form of Cry1 crystal proteins consists of two approximately equal-sized segments. The carboxy-terminal portion of the precursor protein, known as the protoxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains, domain I, domain II, and domain III. Domain I comprises about the first third of the active toxin segment and has been shown to be essential for channel formation. Domains II and III have both been implicated in receptor binding and insect species specificity, depending on the insect and insecticidal protein being examined.

The likelihood of arbitrarily creating a chimeric protein with enhanced properties from the assortment of the domain structures of the numerous native insecticidal proteins known in the art is remote. This is a result of the complex nature of protein structure, oligomerization, and activation (including correct proteolytic processing of the chimeric precursor, if expressed in such a form) required to release an insecticidal protein segment. Only by careful selection of protoxins and specific targets within each parental protein for the creation of a chimeric structure can functional chimeric insecticidal toxins be constructed that exhibit improved insecticidal activity in comparison to the parental proteins from which the chimeras are derived. It is known in the art that reassembly of the protoxin and toxin domains I, II and III of any two or more toxins that are different from each other often results in the construction of proteins that exhibit faulty crystal formation or the complete lack of any detectable insecticidal activity directed to a preferred target insect pest species. Only by trial and error are effective insecticidal chimeras designed, and even then, the skilled artisan is not certain to end up with a chimera that exhibits insecticidal activity that is equivalent to or improved in comparison to any single parental toxin protein from which the constituent protoxin or toxin domains of the chimera may have been derived. For example, the literature reports numerous examples of the construction or assembly of chimeric proteins from two or more crystal protein precursors. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813; Bosch, et al. (U.S. Pat. No. 6,204,246); Malvar and Gilmer (U.S. Pat. No. 6,017,534). In each of these examples, many of the resultant chimeras failed to exhibit insecticidal or crystal forming properties that were equivalent to or improved in comparison to the precursor proteins from which the components of the chimeras were derived.

SUMMARY OF THE INVENTION

Recombinant nucleic acid molecules are provided that encode chimeric insecticidal proteins toxic to Lepidopteran species of plant pests. Each of the chimeric insecticidal proteins can be used alone or in combination with each other and with other insecticidal proteins and insect inhibitory agents in formulations and in planta; thus providing alternatives to insecticidal proteins and insecticidal chemistries currently in use in agricultural systems.

In certain embodiments disclosed herein is a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. This chimeric insecticidal protein exhibits inhibitory activity against an insect species of the order Lepidoptera such as, but not limited to, *Anticarsia gemmatalis, Diatraea saccharalis, Elasmopalpus lignosellus, Helicoverpa zea, Heliothis virescens, Chrysodeixis includens, Spodoptera cosmioides, Spodoptera eridania, Spodoptera frugiperda, Spodoptera exigua, Helicoverpa armigera, Spodoptera litura, Pectinophora gossypiella, Diatraea grandiosella, Earias vitella, Helicoverpa gelotopeon,* and *Rachiplusia nu.*

In another embodiment, a polynucleotide encoding a chimeric insecticidal protein, wherein the polynucleotide is operably linked to a heterologous promoter and the chimeric insecticidal protein comprises the amino acid sequence as set forth in any of SEQ ID NOs: 21, 10, 28, 7, 4, 13, 16, 19, 23, 25, 30, 33, 36, 39, 41, 43, 45, 47, 50 or 53 is disclosed. A polynucleotide encoding a chimeric insecticidal protein, wherein the polynucleotide comprises a nucleotide sequence that optionally: hybridizes under stringent conditions to the reverse complement of the polynucleotide sequence as set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; or encodes the chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53 is also contemplated.

In other embodiments disclosed herein is a host cell comprising the polynucleotide set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52, wherein the host cell is selected from the group consisting of a bacterial host cell or a plant host cell. Contemplated bacterial host include *Agrobacterium, Rhizobium, Bacillus, Brevibacillus, Escherichia, Pseudomonas, Klebsiella,* and *Erwinia*; and wherein the *Bacillus* species is a *Bacillus*

*cereus* or a *Bacillus thuringiensis*, said *Brevibacillus* is a *Brevibacillus laterosperous*, and said *Escherichia* is an *Escherichia coli*. Contemplated plant cells include monocots and dicots.

Other embodiments disclosed herein include insect inhibitory compositions comprising a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. In certain embodiments, the insect inhibitory composition further comprises at least one insect inhibitory agent different from the chimeric insecticidal protein. Contemplated insect inhibitory agents different from the chimeric insecticidal protein include an insect inhibitory protein, an insect inhibitory dsRNA molecule, and an insect inhibitory chemistry. These insect inhibitory agents different from the chimeric insecticidal protein can exhibit activity against one or more pest species of the orders Lepidoptera, Coleoptera, Hemiptera, Homoptera, or Thysanoptera.

In yet another embodiment, disclosed herein is a seed comprising an insect inhibitory effective amount of: a chimeric insecticidal protein comprising the amino acid sequence as set forth in any of SEQ ID NOs: 21, 10, 28, 7, 4, 13, 16, 19, 23, 25, 30, 33, 36, 39, 41, 43, 45, 47, 50 or 53; or a polynucleotide set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Methods of controlling a Lepidopteran pest comprising contacting the Lepidopteran pest with an inhibitory amount of a chimeric insecticidal protein of the invention are also contemplated.

In another embodiment, disclosed herein is a transgenic plant cell, plant or plant part comprising a chimeric insecticidal protein, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28 at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53. Methods of controlling a Lepidopteran pest which comprise exposing the pest to this transgenic plant cell, plant or plant part, wherein said plant cell, plant or plant part expresses a Lepidopteran inhibitory amount of the chimeric insecticidal protein are also contemplated.

In other embodiments herein, commodity products derived from the plant cell, plant, or plant part wherein the product comprises a detectable amount of the chimeric insecticidal protein are provided. Contemplated commodity products include plant biomass, oil, meal, animal feed, flour, flakes, bran, lint, hulls, and processed seed.

Yet another method disclosed herein is a method of producing a seed comprising a chimeric insecticidal protein, the method comprising: planting at least one seed comprising a chimeric insecticidal protein; growing plants from said seed; and harvesting seed from said plants, wherein said harvested seed comprises the chimeric insecticidal protein.

Recombinant polynucleotide molecules encoding a chimeric insecticidal protein, comprising a nucleotide sequence selected from the group consisting of 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; and optionally a polynucleotide sequence encoding an insect inhibitory agent different from the chimeric insecticidal protein are also contemplated herein.

Another recombinant nucleic acid molecule contemplated herein comprises a heterologous promoter operably linked to a polynucleotide segment encoding a chimeric insecticidal proteins, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53; or the polynucleotide segment hybridizes to a polynucleotide having a nucleotide sequence as set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Other embodiments, features, and advantages of the invention will be apparent from the following detailed description, examples, and claims.

BRIEF DESCRIPTION OF THE SEQUENCES

SEQ ID SEQ ID NO: 1 is a recombinant DNA sequence encoding TIC1100 used for expression in a bacterial cell.

SEQ ID NO: 2 is a synthetic DNA sequence encoding TIC1100 for expression in a plant cell.

SEQ ID NO: 3 is a synthetic DNA sequence encoding TIC1100 for expression in a plant cell.

SEQ ID NO: 4 is the amino acid sequence of TIC1100.

SEQ ID NO: 5 is a recombinant DNA sequence encoding TIC860 used for expression in a bacterial cell.

SEQ ID NO: 6 is a synthetic DNA sequence encoding TIC860 for expression in a plant cell.

SEQ ID NO: 7 is the amino acid sequence of TIC860.

SEQ ID NO: 8 is a recombinant DNA sequence encoding TIC867 used for expression in a bacterial cell.

SEQ ID NO: 9 is a synthetic DNA sequence encoding TIC867 for expression in a plant cell.

SEQ ID NO: 10 is the amino acid sequence of TIC867.

SEQ ID NO: 11 is a recombinant DNA sequence encoding TIC867_20 used for expression in a bacterial cell.

SEQ ID NO: 12 is a synthetic DNA sequence encoding TIC867_20 for expression in a plant cell.

SEQ ID NO: 13 is the amino acid sequence of TIC867_20.

SEQ ID NO: 14 is a recombinant DNA sequence encoding TIC867_21 used for expression in a bacterial cell.

SEQ ID NO: 15 is a synthetic DNA sequence encoding TIC867_21 for expression in a plant cell.

SEQ ID NO: 16 is the amino acid sequence of TIC867_21.

SEQ ID NO: 17 is a recombinant DNA sequence encoding TIC867_22 used for expression in a bacterial cell.

SEQ ID NO: 18 is a synthetic DNA sequence encoding TIC867_22 for expression in a plant cell.

SEQ ID NO: 19 is the amino acid sequence of TIC867_22.

SEQ ID NO: 20 is a synthetic DNA sequence encoding TIC867_23 for expression in the plant cell.

SEQ ID NO: 21 is the amino acid sequence of TIC867_23.

SEQ ID NO: 22 is a synthetic DNA sequence encoding TIC867_24 for expression in a plant cell.

SEQ ID NO: 23 is the amino acid sequence of TIC867_24.

SEQ ID NO: 24 is a synthetic DNA sequence encoding TIC867_24 for expression in a plant cell.

SEQ ID NO: 25 is the amino acid sequence of TIC867_25.

SEQ ID NO: 26 is a recombinant DNA sequence encoding TIC868 used for expression in a bacterial cell.

SEQ ID NO: 27 is a synthetic DNA sequence encoding TIC868 for expression in a plant cell.

SEQ ID NO: 28 is the amino acid sequence of TIC868.

SEQ ID NO: 29 is a synthetic DNA sequence encoding TIC868_9 for expression in a plant cell.

SEQ ID NO: 30 is the amino acid sequence of TIC868_9.

SEQ ID NO: 31 is a recombinant DNA sequence encoding TIC868_10 used for expression in a bacterial cell.

SEQ ID NO: 32 is a synthetic DNA sequence for expression in the plant cell encoding the TIC868 variant, TIC868_10.

SEQ ID NO: 33 is the amino acid sequence of TIC868_10.

SEQ ID NO: 34 is a recombinant DNA sequence encoding TIC868_11 used for expression in a bacterial cell.

SEQ ID NO: 35 is a synthetic DNA sequence encoding TIC868_11 for expression in a plant cell.

SEQ ID NO: 36 is the amino acid sequence of TIC868_11.

SEQ ID NO: 37 is a recombinant DNA sequence encoding TIC868_12 used for expression in a bacterial cell.

SEQ ID NO: 38 is a synthetic DNA sequence encoding TIC868_12 for expression in the plant cell.

SEQ ID NO: 39 is the amino acid sequence of TIC868_12.

SEQ ID NO: 40 is a synthetic DNA sequence encoding TIC868_13 for expression in the plant cell.

SEQ ID NO: 41 is the amino acid sequence of TIC868_13.

SEQ ID NO: 42 is a synthetic DNA sequence encoding TIC868_14 for expression in a plant cell.

SEQ ID NO: 43 is the amino acid sequence of TIC868_14.

SEQ ID NO: 44 is a synthetic DNA sequence encoding TIC868_15 for expression in a plant cell.

SEQ ID NO: 45 is the amino acid sequence of TIC868_15.

SEQ ID NO: 46 is a synthetic DNA sequence encoding TIC868_29 for expression in a plant cell.

SEQ ID NO: 47 is the amino acid sequence of TIC868_29.

SEQ ID NO: 48 is a recombinant DNA sequence encoding TIC869 used for expression in a bacterial cell.

SEQ ID NO: 49 is a synthetic DNA sequence encoding TIC869 for expression in a plant cell.

SEQ ID NO: 50 is the amino acid sequence of TIC869.

SEQ ID NO: 51 is a recombinant DNA sequence encoding TIC836 used for expression in a bacterial cell.

SEQ ID NO: 52 is a synthetic DNA sequence encoding TIC836 for expression in a plant cell.

SEQ ID NO: 53 is the amino acid sequence of TIC836.

DETAILED DESCRIPTION OF THE INVENTION

The problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel chimeric insecticidal proteins are disclosed herein, and address each of these needs, particularly against a broad spectrum of Lepidopteran insect pests.

In order to avoid the development of, or circumvent insect resistance against currently used insecticidal proteins, new insecticidal proteins with different modes-of-action (MOA), as well as a broad spectrum and efficacy, are needed for Lepidoptera control. One way to address this need is to discover new insecticidal proteins from different biological sources, preferably from bacteria, fungi or plants. Another approach is to interchange segments between various Bt proteins that exhibit structural similarities to create new chimeric Bt proteins having insect inhibitory properties. The likelihood of creating a chimeric protein with enhanced properties from the re-assortment of the domain structures of numerous native insecticidal crystal proteins known in the art is known in the art to be remote. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813.

Disclosed herein are recombinant nucleic acid molecule sequences that encode novel chimeric insecticidal proteins. These insecticidal proteins address the ongoing need in the art to engineer additional toxic insecticidal proteins with improved insecticidal properties such as increased efficacy against a broader spectrum of target insect pests species and different modes of action. Members of this group of proteins, including the exemplary proteins disclosed herein, exhibit insecticidal activity against Lepidopteran insect pest species.

The term "segment" or "fragment" is used in this application to describe consecutive amino acid or nucleic acid sequences that are shorter than the complete amino acid or nucleic acid sequence describing a disclosed chimeric insecticidal protein. A segment or fragment exhibiting insect inhibitory activity is also disclosed in this application if alignment of such segment or fragment, with the corresponding section of the chimeric insecticidal protein, results in amino acid sequence identity of any fraction percentage from about 65 to about 100 percent between the segment or fragment and the corresponding section of the chimeric insecticidal protein.

Reference in this application to the terms "active" or "activity", "pesticidal activity" or "pesticidal", or "insecticidal activity", "insect inhibitory" or "insecticidal" refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The insecticidal protein can be produced by the plant or can be applied to the plant or to the environment within the location where the plant is located. The terms "bioactivity", "effective", "efficacious" or variations thereof are also terms interchangeably utilized in this application to describe the effects of the chimeric insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the chimeric insecticidal proteins set forth in this application, as well as other proteinaceous toxic agents including those that target Lepidopteran pest species, as well as protein toxins that are used to control other plant pests such as Cry proteins available in the art for use in controlling Coleopteran, Thysanopteranm, Hemipteran and Homopteran species.

It is intended that reference to a pest, particularly a pest of a crop plant, means insect pests of crop plants, particularly those Lepidopteran insect pests that are controlled by the disclosed chimeric insecticidal proteins. However, reference to a pest can also include Coleopteran, Hemipteran and Homopteran insect pests of plants, as well as nematodes and fungi when toxic agents targeting these pests are co-localized or present together with the chimeric insecticidal protein, or a protein that is 65 to about 100 percent identical to the chimeric insecticidal protein.

The chimeric insecticidal proteins disclosed herein exhibit insecticidal activity towards insect pests from the Lepidopteran insect species, including adults, pupae, larvae, and neonates, as well as Hemipteran insect species, including adults and nymphs. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other Archips species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, through a chimeragenesis effort about eight hundred and forty four (844) nucleotide sequences that encode chimeric insecticidal proteins were constructed from the protoxin and toxin domains of known insecticidal toxins (referred to herein as the "parent proteins"), and expressed and tested in bioassay for Lepidopteran activity. A small number of the constructed chimeric insecticidal proteins exhibited improved Lepidopteran activity or an enhanced Lepidopteran spectrum compared to the parent proteins from which its toxin components were derived.

These novel chimeric insecticidal proteins with improved Lepidopteran activity or an enhanced Lepidopteran spectrum were constructed from the following insecticidal parent protein protoxin and toxin domains: Cry1Ah (Domain I), Cry1Bb1 (Domains I and II), Cry1Be2 (Domains I and II), Cry1Ja1 (Domains I and II), Cry1Fa1 (Domains I and II), Cry1Ac (Domain II and protoxin), Cry1Ca (Domain III and protoxin), Cry1Ka (Domain III and protoxin), Cry1Jx (Domain III), Cry1Ab (Domain III), Cry1Ab3 (protoxin), Cry1Da1 (protoxin), Cry4 (protoxin), Cry9 (protoxin), Cry1Be (protoxin), and Cry1Ka (protoxin).

Specifically, the novel chimeric insecticidal proteins of this invention with improved Lepidopteran activity or an enhanced Lepidopteran spectrum comprise the following protoxin and domain combinations: TIC1100/SEQ ID NO:4 (Domain I-Cry1Ah, Domain II-Cry1Ac, Domain III-Cry1Ca, Protoxin-Cry1Ac), TIC860/SEQ ID NO:7 (Domain I-Cry1Bb1, Domain II-Cry1BB1, Domain III-Cry1Ca, Protoxin-Cry1Ac), TIC867/SEQ ID NO:10 (Domain I-Cry1Be2, Domain II-Cry1Be2, Domain III-Cry1Ka, Protoxin-Cry1Ab3), TIC868/SEQ ID NO:28 (Domain I-Cry1Be2, Domain II-Cry1Be2, and Domain III-Cry1Ca, Protoxin-Cry1Ab3), TIC869/SEQ ID NO:50 (Domain I-Cry1Ja1, Domain II-Cry1Ja1, Domain III-Cry1Jx, Protoxin-Cry1Ab3) and TIC836/SEQ ID NO:53 (Domain I-Cry1Fa1, Domain II-Cry1Fa1, Domain III-Cry1Ab, Protoxin-Cry1Ac).

Variants in which amino acid substitutions or alternate protoxin domains were introduced were also constructed for the chimeric insecticidal proteins TIC867 and TIC868. Specifically, these variants of TIC867 and TIC868 comprise the following amino acid substitutions or alternate protoxin domains: TIC867_20/SEQ ID NO:13 (alternate protoxin domain Cry1Da1), TIC867_21/SEQ ID NO:16 (alternate protoxin domain Cry4), TIC867_22/SEQ ID NO:19 (alternate protoxin domain Cry9), TIC867_23/SEQ ID NO:21 (alternate protoxin domain Cry1Be), TIC867_24/SEQ ID NO:23 (alternate protoxin domain Cry1Ka), TIC867_25/SEQ ID NO: 25 (alternate protoxin domain Cry1Ka), TIC868_9/SEQ ID NO:30 (amino acid modification N240S_Y343Q_N349T), TIC868_10/SEQ ID NO:33 (alternate protoxin domain Cry1Da1), TIC868_11/SEQ ID NO:36 (alternate protoxin domain Cry4), TIC868_12/SEQ ID NO:39 (alternate protoxin domain Cry9), TIC868_13/SEQ ID NO:41 (alternate protoxin domain Cry1Be), TIC868_14/SEQ ID NO:43 (alternate protoxin domain Cry1Ka), TIC868_15/SEQ ID NO:45 (alternate protoxin domain Cry1Ca), and TIC868_29/SEQ ID NO:47 (amino acid modification Q136Y_Y343Q_N349T).

As demonstrated in the Examples, each of these TIC867 and TIC868 variants altered the Lepidopteran activity and/or reduced the Lepidopteran activity spectrum of the parent chimeric insecticidal protein, thus indicating that the alternate protoxin domain and the amino acid substitutions had a direct consequence on the insecticidal activity and spectrum of the chimeric insecticidal proteins TIC867 and TIC868.

Many of the chimeric insecticidal proteins demonstrate insecticidal activity against multiple Lepidopteran insect pest species. Specifically, the novel chimeric insecticidal proteins disclosed in this application exhibited activity against one or more of the following Lepidopteran insect pests, Velvet bean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Soybean pod worm (SPW, *Helicoverpa zea*), Cotton bollworm (CBW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Southwestern Corn Borer (SWCB, *Diatraea grandiosella*), Spotted bollworm (SBW, *Earias vitella*), American bollworm (SABW, *Helicoverpa gelotopeon*), and Sunflower looper (SFL, *Rachiplusia nu*). Thus, the exemplary proteins described in this application are related by common function and exhibit insecticidal activity towards insect pests from the Lepidoptera insect species including adults, larvae and pupae.

Proteins that resemble the chimeric insecticidal proteins can be identified by comparison to each other using various computer based algorithms known in the art. For example, amino acid sequence identities of proteins related to the chimeric insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity is disclosed in this application if alignment of such query protein with the subject chimeric insecticidal proteins set forth in SEQ ID NOs: 4, 7, 10, 13, 16, 19, 21, 23, 25, 28, 30, 33, 36, 39, 41, 43, 45, 47, 50 and 53 and results in at least about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein.

As described further in the Examples of this application, synthetic or artificial sequences encoding the chimeric insecticidal proteins were designed for use in plants. Exemplary synthetic nucleotide sequences that were designed for use in plants are set forth in SEQ ID NOs: 2 and 3 (TIC1100), SEQ ID NO:6 (TIC860), SEQ ID NO:9 (TIC867), SEQ ID NO:12 (TIC867_20), SEQ ID NO:15 (TIC867_21), SEQ ID NO:18 (TIC867_22), SEQ ID NO:20 (TIC867_23), SEQ ID NO:22 (TIC867_24), SEQ ID NO: 24 (TIC867_25), SEQ ID NO:27

(TIC868), SEQ ID NO:29 (TIC868_9), SEQ ID NO:32 (TIC868_10), SEQ ID NO:35 (TIC868_11), SEQ ID NO:38 (TIC868_12), SEQ ID NO:40 (TIC868_13), SEQ ID NO:42 (TIC868_14), SEQ ID NO:44 (TIC868_15), SEQ ID NO:46 (TIC868_29), SEQ ID NO:49 (TIC869) and SEQ ID NO:52 (TIC836).

For expression in plant cells, the chimeric insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et at., *Mol. Gen. Genet.* 210:437-442, 1987) or the *Petunia hybrida* EPSPS CTP (CTP4) (see, della-Cioppa et at., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the chimeric insecticidal proteins to the chloroplast, a sequence encoding a chloroplast transit peptide is placed 5' in operable linkage and in frame to a synthetic coding sequence encoding the chimeric insecticidal protein that has been designed for optimal expression in plant cells.

Expression cassettes and vectors containing these synthetic or artificial nucleotide sequences were constructed and introduced into corn, cotton, and soybean plant cells in accordance with transformation methods and techniques which are known in the art. Transformed cells were regenerated into transformed plants that were observed to be expressing the chimeric insecticidal protein. To test pesticidal activity, bioassays were performed in the presence of Lepidopteran pest larvae using plant leaf disks obtained from the transformed plants. Recombinant nucleic acid molecule compositions that encode the chimeric insecticidal proteins are contemplated. For example, the chimeric insecticidal proteins can be expressed with recombinant DNA constructs in which a polynucleotide molecule with an ORF encoding a chimeric insecticidal protein is operably linked to genetic expression elements such as a promoter and any other regulatory element necessary for expression in the system for which the construct is intended. Non-limiting examples include a plant-functional promoter operably linked to the synthetic chimeric insecticidal protein encoding sequences for expression of the chimeric insecticidal protein in plants or a Bt-functional promoter operably linked to a chimeric insecticidal protein encoding sequence for expression of the protein in a Bt bacterium or other *Bacillus* species. Other elements can be operably linked to the chimeric insecticidal proteins encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herein include, but are not limited to, a heterologous promoter operably linked to a polynucleotide such as SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, and 52, that encodes the polypeptide or protein having the amino acid sequence as set forth in SEQ ID NOs: 4 (TIC1100), 7 (TIC860), 10 (TIC867), 13 (TIC867_20), 16 (TIC867_21), 19 (TIC867_22), 21 (TIC867_23), 23 (TIC867_24), 25 (TIC867_25), 28 (TIC868), 30 (TIC868_9), 33 (TIC868_10), 36 (TIC868_11), 39 (TIC867_12), 41 (TIC867_13), 43 (TIC867_14), 45 (TIC867_15), 47 (TIC867_29), 50 (TIC869) and 53 (TIC836). A heterologous promoter can also be operably linked to synthetic DNA coding sequences encoding a plastid targeted chimeric insecticidal protein and untargeted chimeric insecticidal protein. It is contemplated that the codons of a recombinant nucleic acid molecule encoding for a chimeric insecticidal protein disclosed herein can be substituted by synonymous codons (known in the art as a silent substitution).

A recombinant DNA molecule or construct comprising a chimeric insecticidal protein encoding sequence can further comprise a region of DNA that encodes for one or more toxic agents which can be configured to concomitantly express or co-express with a DNA sequence encoding a chimeric insecticidal protein, a protein different from a chimeric insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof The proteins of this invention can be expressed from a multi-gene expression system in which a chimeric insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising chimeric insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a chimeric insecticidal protein encoding sequence in a host cell, or subsequent expression of the encoded polypeptide. An exogenous recombinant polynucleotide or recombinant DNA construct that comprises chimeric insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the chimeric insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of a chimeric insecticidal proteins are provided. Such plants can be made by introducing a polynucleotide that encodes the chimeric insecticidal proteins provided in this application into a plant cell, and selecting a plant derived from said plant cell that expresses an insect or Lepidoptera-inhibitory amount of the chimeric insecticidal protein. Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), and 2008/0256667 (cotton).

Plants expressing the chimeric insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of a chimeric insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a chimeric insecticidal protein.

Methods of controlling insects, in particular Lepidoptera infestations of crop plants, with the chimeric insecticidal proteins are also disclosed in this application. Such methods can comprise growing a plant comprising an insect- or Lepidoptera-inhibitory amount of the chimeric insecticidal protein. In certain embodiments, such methods can further comprise any one or more of: (i) applying any composition comprising or encoding a chimeric insecticidal protein to a plant or a seed that gives rise to a plant; and (ii) transforming a plant or a plant cell that gives rise to a plant with a polynucleotide encoding a chimeric insecticidal protein. In general, it is contemplated that chimeric insecticidal protein can be provided in a composition, provided in a microorganism, or provided in a transgenic plant to confer insect inhibitory activity against Lepidopteran insects.

In certain embodiments, the chimeric insecticidal protein is the insecticidally active ingredient of an insect inhibitory composition prepared by culturing recombinant *Bacillus* or any other recombinant bacterial cell transformed to express a chimeric insecticidal protein under conditions suitable for expression. Such a composition can be prepared by desiccation, lyophilization, homogenization, extraction, filtration, centrifugation, sedimentation, or concentration of a culture of such recombinant cells expressing/producing the chimeric insecticidal protein. Such a process can result in a *Bacillus* or other entomopathogenic bacterial cell extract, cell suspension, cell homogenate, cell lysate, cell supernatant, cell filtrate, or cell pellet. By obtaining the chimeric insecticidal protein so produced, a composition that includes the chimeric insecticidal protein can include bacterial cells, bacterial spores, and parasporal inclusion bodies and can be formulated for various uses, including as agricultural insect inhibitory spray products or as insect inhibitory formulations in diet bioassays.

The aforementioned compound or formulation can further comprise an agriculturally-acceptable carrier, such as a bait, a powder, dust, pellet, granule, spray, emulsion, a colloidal suspension, an aqueous solution, a *Bacillus* spore or crystal preparation or a seed treatment. The compound or formulation can also further comprise a recombinant plant cell, plant tissue, seed or plant transformed to express one or more of the proteins; or bacterium transformed to express one or more of the proteins. Depending on the level of insect inhibitory or insecticidal inhibition inherent in the recombinant polypeptide and the level of compound or formulation to be applied to a plant or diet assay, the compound or formulation can include various by weight amounts of the recombinant polypeptide, e.g. from 0.0001% to 0.001% to 0.01% to 1% to 99% by weight of the recombinant polypeptide.

In an embodiment, in order to reduce the likelihood of resistance development, an insect inhibitory composition or transgenic plant comprising a chimeric insecticidal protein can further comprise at least one additional toxic agent that exhibits insect inhibitory activity against the same Lepidopteran insect species, but which is different from the chimeric insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide(s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713, 063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AflP-1A and derivatives thereof (U.S. Patent Publication 2014-0033361 A1), AflP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the chimeric insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and ω-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature web site maintained by Neil Crickmore (on the world wide web at btnomenclature.info).

Chimeric insecticidal protein-encoding sequences and sequences having a substantial percentage identity to the chimeric insecticidal proteins can be identified using methods known to those of ordinary skill in the art such as polymerase chain reaction (PCR), thermal amplification and hybridization. For example, the chimeric insecticidal proteins can be used to produce antibodies that bind specifically to related proteins, and can be used to screen for and to find other proteins that are closely related.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:2 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:2 can be used to detect the respective chimeric insecticidal protein in commodity products derived from pooled sources where only a fraction of the commodity product is derived from a transgenic plant containing any of SEQ ID NO:2.

EXAMPLES

In view of the foregoing, those of skill in the art will appreciate that the following disclosed embodiments are merely representative of the invention, which may be Example 1

Creation and Cloning of Lepidopteran-Active Novel Chimeric Insecticidal Protein Coding Sequences This Example illustrates the creation of the novel chimeric insecticidal proteins and the cloning and expressing of the chimeric insecticidal proteins.

Recombinant nucleic acid sequences were constructed from known Cry protein genes to produce polynucleotide sequences encoding novel chimeric insecticidal proteins. The resulting polynucleotide sequences were cloned into a *Bacillus thuringiensis* (Bt) expression plasmid vector. After confirmation of the polynucleotide sequence, the expression plasmid was transformed into Bt and expressed. Preparations of the expressed novel chimeric proteins were assayed for activity against various Lepidopteran pests.

Many polynucleotide sequences encoding chimeric insecticidal proteins were produced and tested in bioassay. Not all of the chimeric insecticidal proteins demonstrated activity. Only a few of the chimeric insecticidal proteins were selected based upon their activity to specific Lepidoptera demonstrated in bioassay. Amino acid variants in which amino acid substitutions, or alternate protoxin domains, were introduced were also produced based upon the original chimeric insecticidal proteins TIC867 and TIC868. The components of the chimeric insecticidal proteins (domains I, II and III and the protoxin) of the present invention are presented in Table 1. The amino acid substitutions in the TIC868 variants relative to the original TIC868 protein sequence are also presented.

Example 2

The Novel Chimeric Insecticidal Proteins Demonstrate Activity Against Lepidopteran Pests This Example illustrates the testing of the chimeric insecticidal proteins described in Example 1 and the Lepidopteran activity observed for the chimeric insecticidal proteins.

Polynucleotide sequences encoding chimeric insecticidal proteins were expressed in Bt. The expressed chimeric insecticidal proteins were then assayed against a variety of Lepidoptera known to be pests of corn, sugarcane, soybean and cotton, as well as other crop plants. Specifically, the insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frupperda*), Beet armyworm (BAW, *Spodoptera exigua*), Old World bollworm (OBW, *Hehcoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*), Spotted bollworm (SBW, *Earias vitella*), and European corn borer (ECB, *Ostrinia nubilalis*). Corn earworm (CEW, *Hehcoverpa zea*) is also referred to as Soybean pod worm (SPW) and Cotton bollworm (CBW). Activity was determined through a combination of mortality and stunting scores as well as MIC50 scores. MIC50 refers to a molt inhibition concentration wherein both the dead larvae and L1 larvae (larvae that failed to molt to second instars) are factored into the score. Table 2 shows the activity of each chimeric insecticidal protein. A '+' sign indicates activity observed to the specific insect pest.

TABLE 1

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC1100 | 4 | Cry1Ah | Cry1Ac | Cry1Ca | Cry1Ac | |
| TIC860 | 7 | Cry1Bb1 | Cry1Bb1 | Cry1Ca | Cry1Ac | |
| TIC867 | 10 | Cry1Be2 | Cry1Be2 | Cry1Ka | Cry1Ab3 | |
| TIC867_20 | 13 | Cry1Be2 | Cry1Be2 | Cry1Ka | Cry1Da1 | |
| TIC867_21 | 16 | Cry1Be2 | Cry1Be2 | Cry1Ka | Cry4 | |
| TIC867_22 | 19 | Cry1Be2 | Cry1Be2 | Cry1Ka | Cry9 | |
| TIC867_23 | 21 | Cry1Be2 | Cry1Be2 | Cry1Ka | Cry1Be | |
| TIC867_24 | 23 | Cry1Be2 | Cry1Be2 | Cry1Ka | Cry1Ka | |
| TIC867_25 | 25 | Cry1Be2 | Cry1Be2 | Cry1Ka | Cry1Ca | |
| TIC868 | 28 | Cry1Be2 | Cry1Be2 | Cry1Ca | Cry1Ab3 | |
| TIC868_9 | 30 | Cry1Be2 | Cry1Be2 | Cry1Ca | Cry1Ab3 | N240S_Y343Q_N349T |
| TIC868_10 | 33 | Cry1Be2 | Cry1Be2 | Cry1Ca | Cry1Da1 | |
| TIC868_11 | 36 | Cry1Be2 | Cry1Be2 | Cry1Ca | Cry4 | |
| TIC868_12 | 39 | Cry1Be2 | Cry1Be2 | Cry1Ca | Cry9 | |
| TIC868_13 | 41 | Cry1Be2 | Cry1Be2 | Cry1Ca | Cry1Be | |
| TIC868_14 | 43 | Cry1Be2 | Cry1Be2 | Cry1Ca | Cry1Ka | |
| TIC868_15 | 45 | Cry1Be2 | Cry1Be2 | Cry1Ca | Cry1Ca | |
| TIC868_29 | 47 | Cry1Be2 | Cry1Be2 | Cry1Ca | Cry1Ab3 | Q136Y_Y343Q_N349T |
| TIC869 | 50 | Cry1Ja1 | Cry1Ja1 | Cry1Jx | Cry1Ab3 | |
| TIC836 | 53 | Cry1Fa1 | Cry1Fa1 | Cry1Ab | Cry1Ac | |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138: 9-37 (1984). The first amino acid sequence abbreviation indicates the original amino acid in the given scaffold protein, the number represents the position of the amino acid, and the second amino acid sequence abbreviation indicates the amino acid placed in that position in the improved variant protein.

TABLE 2

Bioassay activity against selected Lepidoptera.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | | + | | + | | + | + | | | | |
| TIC860 | 7 | + | + | + | | + | + | + | + | + | + | | + | + | | + | | + |
| TIC867 | 10 | + | + | | | + | | + | | + | + | + | + | | | + | | |
| TIC867_20 | 13 | | | | | | | | | | | | | | | | | |
| TIC867_21 | 16 | | | | + | | | | | | | | | | | | | |
| TIC867_22 | 19 | | | | + | | | | | + | | | | | | | | |
| TIC868 | 28 | + | + | | | + | | + | | + | + | | + | + | | + | | + |
| TIC868_10 | 33 | | | | | | | | | + | | | | | | | | |
| TIC868_11 | 36 | | | | | | | | | + | | | | | | | | |
| TIC868_12 | 39 | | | | | | | | | + | | | | | | | | |
| TIC869 | 50 | + | + | | | | | | + | | + | | | | + | | | |
| TIC836 | 53 | + | | | | + | | | + | + | + | | | | | | | |

As can be seen in Table 2 above, most of the chimeric insecticidal proteins exhibited activity against one or more Lepidopteran pest species.

Example 3

Synthesis of Genes Encoding Chimeric Insecticidal Proteins and for Expression in Plants This Example illustrates the synthesis of polynucleotides encoding the chimeric insecticidal proteins for expression in plants.

Synthetic coding sequences were constructed for use in expression of the chimeric insecticidal proteins in plants. The synthetic sequences were designed and synthesized according to methods generally described in U.S. Pat. No. 5,500,365, avoiding certain inimical problem sequences such as ATTTA and A/T rich plant polyadenylation sequences while preserving the amino acid sequence of the chimeric insecticidal protein. The nucleotide sequences for these genes encoding the chimeric insecticidal proteins for expression in plants are listed in Table 3.

TABLE 3

Polynucleotide Sequences Encoding Chimeric Insecticidal Proteins Designed for Use in Plants.

| Insecticidal Protein | DNA SEQ ID NO: | PRT SEQ ID NO: |
|---|---|---|
| TIC1100 | 2 | 4 |
| TIC1100 | 3 | 4 |
| TIC860 | 6 | 7 |
| TIC867 | 9 | 10 |
| TIC867_20 | 12 | 13 |
| TIC867_21 | 15 | 16 |
| TIC867_22 | 18 | 19 |
| TIC867_23 | 20 | 21 |
| TIC867_24 | 22 | 23 |
| TIC867_25 | 24 | 25 |
| TIC868 | 27 | 28 |
| TIC868_9 | 29 | 30 |
| TIC868_10 | 32 | 33 |
| TIC868_11 | 35 | 36 |
| TIC868_12 | 38 | 39 |
| TIC868_13 | 40 | 41 |
| TIC868_14 | 42 | 43 |
| TIC868_15 | 44 | 45 |
| TIC868_29 | 46 | 47 |
| TIC869 | 49 | 50 |
| TIC836 | 52 | 53 |

Example 4

Expression Cassettes for the Expression of Chimeric Insecticidal Proteins in Plants This Example illustrates the construction of expression cassettes comprising polynucleotide sequences designed for use in plants which encode chimeric insecticidal proteins.

A variety of plant expression cassettes were constructed with the polynucleotide sequences encoding the chimeric insecticidal proteins designed for plant expression provided in Table 3. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

Example 5

Lepidopteran Activity of the Chimeric Insecticidal Proteins in Stably Transformed Corn This Example illustrates the inhibitory activity exhibited by the chimeric insecticidal proteins against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frugiperda*), Black cutworm (BCW, *Agrotis ipsilon*) and Southwestern Corn Borer (SWCB, *Diatraea grandiosella*).

Leaf disc bioassay was performed on $R_0$ and $F_1$ generation transgenic plants. In addition, leaf damage ratings were assessed for whole transgenic $F_1$ plants expressing certain chimeric insecticidal proteins infested with the Lepidopteran insect pests. $F_1$ transgenic events expressing TIC860 and TIC868 were also assessed for activity in the field against FAW, CEW, and SWCB. The assay results are shown in Table 4. A '+' sign indicates activity observed to the specific insect pest. As can be seen in Table 4, most of the chimeric insecticidal proteins and many of the chimeric insecticidal protein variants demonstrated activity against one or more Lepidopteran pest species.

pests when expressed in soybean plants and provided as a diet to the respective insect pest.

The coding sequences for selected chimeric insecticidal proteins were redesigned for plant expression, cloned into a binary plant transformation vector, and used to transform soybean plant cells. The plant transformation vectors comprised a first transgene cassette for expression of the chimeric insecticidal protein as described in Example 4 and a second transgene cassette for the selection of transformed plant cells using spectinomycin selection. In some instances, such as in the case of TIC1100, TIC860 and TIC836, a chloroplast transit peptide coding sequence was operably linked to the chimeric insecticidal coding sequence. Assays were performed with plastid targeted and untargeted TIC1100, TIC860 and TIC836. Table 5 below shows the chimeric insecticidal and TIC867 variant chimeric insecticidal protein and associated coding sequences used for expression in stably transformed soybean.

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 5 or alternatively, lyophilized tissue was used in the insect diet for bioassay. Bioassay was performed against FAW, Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera cosmioides*), Lesser cornstalk borer (LSCB, *Elasmopalpus lignosellus*) and Old World bollworm (OBW, *Hehcoverpa armigera*).

Table 5 shows the activity against selected species of Lepidoptera for each insecticidal protein in $R_0$ generation

TABLE 4

Bioassay activity of chimeric insecticidal proteins from stably transformed corn leaf tissue.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + |  |  | + |  | + |  | + | + |  | + | + |  |  |  |  |
| TIC860 | 7 | + | + | + |  | + | + | + | + | + | + |  | + | + |  | + |  | + |
| TIC867 | 10 | + | + |  |  | + |  | + |  | + | + | + | + |  |  | + |  |  |
| TIC867_20 | 13 | NT | NT | NT |  | NT | NT | NT | NT |  | NT | NT | NT | NT | NT | NT | NT | NT |
| TIC867_21 | 16 | NT | NT | NT | + | NT | NT | NT | NT |  | NT | NT | NT | NT | NT | NT | NT | NT |
| TIC867_22 | 19 | NT | NT | NT | + | NT | NT | NT | NT | + | NT | NT | NT | NT | NT | NT | NT | NT |
| TIC868 | 28 | + | + |  |  | + |  | + | + | + |  | + | + |  | + |  |  | + |
| TIC868_10 | 33 | NT | NT | NT | + | NT | NT | NT | NT | + | NT | NT | NT | NT | NT | NT | NT | NT |
| TIC868_11 | 36 | NT | NT | NT | + | NT | NT | NT | NT | + | NT | NT | NT | NT | NT | NT | NT | NT |
| TIC868_12 | 39 | NT | NT | NT | + | NT | NT | NT | NT | + | NT | NT | NT | NT | NT | NT | NT | NT |
| TIC869 | 50 | + | + |  |  |  |  | + | + | + |  |  |  |  | + |  |  |  |
| TIC836 | 53 | + |  |  |  | + |  | + | + | + |  |  |  |  |  |  |  |  |

Example 6

Lepidopteran Activity of the Chimeric Insecticidal Proteins in Stably Transformed Soybean This Example illustrates the inhibitory activity exhibited by the chimeric insecticidal proteins against Lepidopteran plants, wherein '+' indicates activity. As can be seen in Table 5, each of the chimeric insecticidal proteins expressed in stably transformed soybean demonstrated activity against multiple Lepidopteran species. Of particular note is that the TIC867 variant, TIC867_23 demonstrated activity against SPW.

TABLE 5

Bioassay activity of chimeric insecticidal proteins from stably transformed $R_0$ soybean leaf tissue.

| Insecticidal Protein | FAW | SAW | SBL | SPW | VBC | TBW | BLAW | LSCB | OBW |
|---|---|---|---|---|---|---|---|---|---|
| TIC1100 | + | + | + |   | + |   | + | + | + |
| TIC860 | + | + | + |   | + |   | + |   |   |
| TIC867 | + | + | + |   | + | + | + |   |   |
| TIC867_20 |   | + | + |   |   |   |   |   |   |
| TIC867_21 |   | + | + |   |   |   |   |   |   |
| TIC867_22 |   | + | + |   |   |   |   |   |   |
| TIC867_23 | + | + | + | + |   |   |   |   |   |
| TIC867_24 |   | + | + |   |   |   |   |   |   |
| TIC867_25 |   | + | + |   |   |   |   |   |   |
| TIC868 | + |   | + |   | + |   | + | + |   |
| TIC869 |   | + |   |   | + | + | + |   |   |
| TIC836 | + | + | + |   | + | + | + |   | + |

Selected transformed events were allowed to self-pollinate and the resulting seed was grown. Leaf tissue was harvested from the R1 generation plants and used in a feeding bioassay. $R_1$ plants expressing TIC1100, TIC860, TIC867, TIC868, TIC869 and TIC836 were assayed for activity against SAW, SBL, SPW and VBC. Table 6 shows the activity observed in these tests. A '+' sign indicates activity observed to the specific insect pest. As demonstrated in Table 6, most of the expressed chimeric insecticidal proteins from $R_1$ generation plants demonstrated activity to one or more Lepidopteran species.

TABLE 6

Bioassay activity of chimeric insecticidal proteins from stably transformed $R_1$ soybean leaf tissue.

| Toxin | SAW | SBL | SPW | VBC |
|---|---|---|---|---|
| TIC1100 | + | + |   | + |
| TIC860 | + | + |   | + |
| TIC867 | + |   |   |   |
| TIC868 | + | + |   | + |
| TIC869 | + | + |   | + |
| TIC836 | + | + |   | + |

Table 7 demonstrates the results of field tests conducted in screen houses with stably transformed $R_1$ generation soybean plants expressing TIC1100, TIC860, and TIC836. Species used to infest plants in the screen houses include SAW, SBL and SPW. Resistance was defined as being less than or equal to fifteen percent defoliation in the soybean plants. The resistance observed in these cage trials is consistent with the resistance observed in the $R_1$ generation soybean leaf tissue assay presented in Table 6. A '+' sign indicates activity observed to the specific insect pest.

TABLE 7

Activity Profile of TIC1100, TIC860 and TIC836 Expressed in $R_1$ Generation Soybean Tested in Screen House Field Tests.

| Toxin | SAW | SBL | SPW |
|---|---|---|---|
| TIC1100 | + | + |   |
| TIC860 | + | + |   |
| TIC836 | + | + |   |

Field tests in screen houses with stably transformed $R_1$ generation soybean plants expressing TIC867 and TIC869 were also conducted at two different locations in Argentina, Acevedo and Fontezuela. Species used to infest plants in the screen houses include South American bollworm (SABW, Helicoverpa gelotopeon), VBC, BLAW, and Sunflower looper (SFL, Rachiplusia nu). Resistance was defined as being less than or equal to fifteen percent defoliation in the soybean plants. Table 8 below shows the resistance observed. A '+' sign indicates activity observed to the specific insect pest. As demonstrated in Table 8, transgenic soybean plants expressing TIC867 demonstrated resistance to BLAW and VBC. Transgenic soybean plants expressing TIC869 demonstrated resistance to SABW, SFL, BLAW, and VBC.

TABLE 8

Activity Profile of TIC867 and TIC869 Expressed in $R_1$ Generation Soybean Tested in Screen House Field Tests.

| | Acevedo | | | Fontezuela | | |
|---|---|---|---|---|---|---|
| Toxin | SABW | SFL | VBC | SABW | BLAW | VBC |
| TIC867 |   | + |   |   | + | + |
| TIC869 | + | + | + | + | + | + |

Example 7

Lepidopteran Activity of the Chimeric Insecticidal Proteins in Stably Transformed Cotton This Example illustrates the inhibitory activity exhibited by the chimeric insecticidal proteins against Lepidopteran pests when expressed in cotton plants and provided as a diet to the respective insect pest.

The coding sequences for selected chimeric insecticidal proteins were redesigned for plant expression, cloned into a binary plant transformation vector, and used to transform cotton plant cells. The resulting binary vectors were similar to those described in Example 4 and were used to express plastid targeted and untargeted TIC860 (coding sequence: SEQ ID NO: 6; protein sequence: SEQ ID NO: 7), TIC867 (coding sequence: SEQ ID NO: 9; protein sequence: SEQ ID NO: 10), TIC868 (coding sequence: SEQ ID NO: 27; protein sequence: SEQ ID NO: 28) and TIC867_23 (coding sequence: SEQ ID NO: 20; protein sequence: SEQ ID NO: 23).

Cotton plant cells were transformed by an Agrobacterium-mediated transformation method. Transformed cotton cells were induced to form whole plants. Cotton leaf tissue was used in bioassay as described in Example 5 against Cotton Boll Worm (CBW, *Helicoverpa zea*), FAW, TBW and SBL. Table 9 shows the activity observed against these Lepidopteran species for TIC860, TIC867, and TIC868 in stably transformed $R_0$ generation cotton, wherein '+' indicate activity. As can be seen in Table 9, TIC860, TIC867, and TIC868 demonstrated activity against two or more Lepidopteran pest species in stably transformed $R_0$ generation cotton.

TABLE 9

Bioassay activity of TIC860, TIC867 and TIC868 from stably transformed $R_0$ cotton leaf tissue.

| Toxin | CBW | FAW | TBW | SBL |
|---|---|---|---|---|
| TIC860 | | + | | + |
| TIC867 | + | + | + | NT |
| TIC868 | | + | | + |

Selected transformation events were used to produce $R_1$ seed. $R_1$ Plants expressing TIC860, TIC867, and TIC868 were assayed for resistance to CBW, FAW, TBW, and SBL. Leaf, square and boll tissues were used in assay. Table 10 shows the activity observed in these tests. A '+' sign indicates activity observed to the specific insect pest. As demonstrated in Table 10, TIC860 demonstrated activity against FAW in the leaf tissue. Further, the chimeric insecticidal protein TIC867 demonstrated activity against CBW and FAW in the leaf, square and boll tissues, as well as TBW and SBL in the leaf The chimeric insecticidal protein TIC868 demonstrated activity against FAW in the leaf, square and boll tissues, as well as TBW and SBL in the leaf.

TABLE 10

Bioassay activity of chimeric insecticidal proteins from stably transformed $R_1$ cotton leaf tissue.

| Toxin | CBW | | | FAW | | | TBW | SBL |
| | Leaf | Square | Boll | Leaf | Square | Boll | Leaf | Leaf |
|---|---|---|---|---|---|---|---|---|
| TIC860 | | | | + | | | | |
| TIC867 | + | + | + | + | + | + | + | + |
| TIC868 | | | | + | + | + | + | + |

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A chimeric insecticidal protein comprising SEQ ID NO:10, wherein the chimeric insecticidal protein exhibits inhibitory activity against an insect species of the order Lepidoptera.

2. A polynucleotide encoding the chimeric insecticidal protein of claim 1, wherein the polynucleotide is operably linked to a heterologous promoter.

3. A polynucleotide encoding a chimeric insecticidal protein, wherein the polynucleotide:

a) comprises SEQ ID NO:9; or b) encodes the chimeric insecticidal protein of claim 1.

4. A host cell comprising the polynucleotide of claim 3, wherein said polynucleotide comprises SEQ ID NO: 9, wherein the host cell is selected from the group consisting of a bacterial host cell and a plant host cell.

5. The host cell of claim 4, wherein the bacterial host cell is selected from the group consisting of *Agrobacterium, Rhizobium, Bacillus, Brevibacillus, Escherichia, Pseudomonas, Klebsiella*, and *Erwinia*.

6. The host cell of claim 4, wherein said plant host cell is selected from the group of plants consisting of monocots and dicots.

7. An insect inhibitory composition comprising the chimeric insecticidal protein of claim 1.

8. The insect inhibitory composition of claim 7, further comprising at least one insect inhibitory agent different from the chimeric insecticidal protein.

9. The insect inhibitory composition of claim 8, wherein said at least one insect inhibitory agent is selected from the group consisting of an insect inhibitory protein and an insect inhibitory dsRNA molecule.

10. The insect inhibitory composition of claim 8, wherein said at least one other insect inhibitory agent exhibits activity against one or more pest species of the orders Lepidoptera, Coleoptera, Hemiptera, Homoptera, or Thysanoptera.

11. A seed comprising an insect inhibitory effective amount of:

a) the chimeric insecticidal protein of claim 1; or b) the polynucleotide set forth in SEQ ID NO:9.

12. A method of controlling a Lepidopteran pest, the method comprising contacting the Lepidopteran pest with an inhibitory amount of the chimeric insecticidal protein of claim 1.

13. A transgenic plant cell, plant or plant part comprising a chimeric insecticidal protein, wherein the chimeric insecticidal protein comprises SEQ ID NO:10.

14. A method of controlling a Lepidopteran pest, comprising exposing the pest to the transgenic plant or plant part of claim 13, wherein said plant or plant part expresses a Lepidopteran inhibitory amount of the chimeric insecticidal protein.

15. A commodity product derived from said plant or plant part of claim 13, wherein the product comprises a detectable amount of the chimeric insecticidal protein.

16. The commodity product of claim 15, wherein the product is selected from the group consisting of plant biomass, oil, meal, animal feed, flour, flakes, bran, lint, hulls, and processed seed.

17. A method of producing a seed comprising the chimeric insecticidal protein of claim 1, the method comprising:

a) planting at least one seed comprising the chimeric insecticidal protein of claim 1;

b) growing at least one plant from said seed; and c) harvesting seeds from said at least one plant, wherein the harvested seeds comprise the chimeric insecticidal protein of claim 1.

18. A recombinant polynucleotide molecule encoding the chimeric insecticidal protein of claim 1, said molecule comprising SEQ ID NO:9 and a polynucleotide sequence encoding an insect inhibitory agent different from the chimeric insecticidal protein.

19. A recombinant nucleic acid molecule comprising a heterologous promoter operably linked to a polynucleotide segment encoding a chimeric insecticidal protein, wherein:
   a) the chimeric insecticidal protein comprises SEQ ID NO: 10; or
   b) the polynucleotide segment comprises SEQ ID NO: 9;
   wherein said chimeric insecticidal protein exhibits inhibitory activity against an insect species of the order Lepidoptera.

* * * * *